United States Patent [19]

Bläckberg et al.

[11] Patent Number: 5,763,739
[45] Date of Patent: Jun. 9, 1998

[54] TRANSGENIC NON-HUMAN MAMMALS PRODUCING BSSL VARIANTS

[75] Inventors: Lars Gustav Bläckberg; Michael Edlund; Stig Lennart Hansson; Olle Carl Edward Hernell, all of Umeå; Lennart Gustav Lundberg, Billdal; Mats Olof Strömqvist, Umeå; Jan Birger Fredrik Törnell, Västra Frölunda, all of Sweden

[73] Assignee: Astra Aktiebolag, Sodertalje, Sweden

[21] Appl. No.: 445,050

[22] Filed: May 19, 1995

Related U.S. Application Data

[62] Division of Ser. No. 204,691, Mar. 1, 1994.

[30] Foreign Application Priority Data

Mar. 1, 1993 [SE] Sweden .................................. 9300686
Mar. 4, 1993 [SE] Sweden .................................. 9300722

[51] Int. Cl.$^6$ .............................. C12N 15/00; C07K 1/00
[52] U.S. Cl. .................. 800/2; 800/DIG. 1; 800/DIG. 2; 800/DIG. 4; 435/172.3; 435/69.1
[58] Field of Search .................... 435/172.3, 69.1, 435/198, 320.1, 240.2; 935/9, 10, 11, 14, 22, 24; 800/2, DIG. 1, DIG. 4; 514/2; 424/94.6, 535; 426/35

[56] References Cited

U.S. PATENT DOCUMENTS 4,944,944 7/1990 Tang et al. .................... 424/94.6

FOREIGN PATENT DOCUMENTS 9115234 10/1991 WIPO ........................... A61K 37/54

OTHER PUBLICATIONS

J. Nilsson et al. Eur J. Biochem 192:543–550 ('90).
I. Wilmut et al. Experientia 47: 905–912 ('91).
K. Ebert et al. Bio/Technology 9: 835–838 ('91).
H. Bialy Bio/Technology 9:786–788 ('91).
R. Rieger et al., Glossary of Genetis & Cyzogenetics, 4$^{th}$ Ed., Springer–Verlag, Berlin NY, 1976, p. 282.
J. Han et al. Biochem. 26: 1617–1625 ('87).
C. Pittus et al. PNAS 85: 5874–5878 ('88).

*Primary Examiner*—Charles C. P. Rories
*Attorney, Agent, or Firm*—White & Case L.L.P.

[57] ABSTRACT

The present invention relates to novel polypeptides which are variants of Bile Salt-Stimulated Lipase (BSSL; EC 3.1.1.1). It also relates to DNA molecules encoding the said polypeptides, and to subproducts comprising the said DNA molecules. The invention further relates to processes for producing the said BSSL variants and for producing transgenic non-human mammals capable of expressing the BSSL variants.

Furthermore the invention relates to such transgenic animals as well as to infant formulas comprising milk from such transgenic animals. The invention also relates to pharmaceutical compositions comprising the said polypeptides; and the use of the said polypeptides and DNA molecules for the manufacture of medicaments.

7 Claims, 18 Drawing Sheets

| PRIMER | SEQUENCE (5'-3') |
|---|---|
| 5'-PRIMER | CTGTGTGGCAAGAAGGAAGTGTTGT |
| 3'-PRIMER | CAACTCCTGACCTCAAGTGATC |

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 2428 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Homo sapiens
        ( F ) TISSUE TYPE: mammary gland ( i x ) FEATURE:
        ( A ) NAME/KEY: CDS
        ( B ) LOCATION: 82..2319
        ( D ) OTHER INFORMATION: /product="bile-salt-stimulated lipase"

( i x ) FEATURE:
        ( A ) NAME/KEY: exon
        ( B ) LOCATION: 985..1173

( i x ) FEATURE:
        ( A ) NAME/KEY: exon ( B ) LOCATION: 1174..1377

( i x ) FEATURE:
    ( A ) NAME/KEY: exon
    ( B ) LOCATION: 1378..1575

( i x ) FEATURE:
    ( A ) NAME/KEY: exon
    ( B ) LOCATION: 1576..2415

( i x ) FEATURE:
    ( A ) NAME/KEY: mat_peptide
    ( B ) LOCATION: 151..2316

( i x ) FEATURE:
    ( A ) NAME/KEY: polyA_signal
    ( B ) LOCATION: 2397..2402

( i x ) FEATURE:
    ( A ) NAME/KEY: repeat_region
    ( B ) LOCATION: 1756..2283

( i x ) FEATURE:
    ( A ) NAME/KEY: 5'UTR
    ( B ) LOCATION: 1..81

( i x ) FEATURE:
    ( A ) NAME/KEY: repeat_unit
    ( B ) LOCATION: 1756..1788

( i x ) FEATURE:
    ( A ) NAME/KEY: repeat_unit
    ( B ) LOCATION: 1789..1821

( i x ) FEATURE:
    ( A ) NAME/KEY: repeat_unit
    ( B ) LOCATION: 1822..1854

( i x ) FEATURE:
    ( A ) NAME/KEY: repeat_unit
    ( B ) LOCATION: 1855..1887

( i x ) FEATURE:
    ( A ) NAME/KEY: repeat_unit
    ( B ) LOCATION: 1888..1920

( i x ) FEATURE:
    ( A ) NAME/KEY: repeat_unit
    ( B ) LOCATION: 1921..1953

( i x ) FEATURE:
    ( A ) NAME/KEY: repeat_unit
    ( B ) LOCATION: 1954..1986

( i x ) FEATURE:
    ( A ) NAME/KEY: repeat_unit
    ( B ) LOCATION: 1987..2019

( i x ) FEATURE:
    ( A ) NAME/KEY: repeat_unit
    ( B ) LOCATION: 2020..2052

( i x ) FEATURE:
    ( A ) NAME/KEY: repeat_unit
    ( B ) LOCATION: 2053..2085

( i x ) FEATURE:
    ( A ) NAME/KEY: repeat_unit
    ( B ) LOCATION: 2086..2118

( i x ) FEATURE:
    ( A ) NAME/KEY: repeat_unit
    ( B ) LOCATION: 2119..2151

( i x ) FEATURE:
    ( A ) NAME/KEY: repeat_unit
    ( B ) LOCATION: 2152..2184

( i x ) FEATURE:
    ( A ) NAME/KEY: repeat_unit

-continued ( B ) LOCATION: 2185..2217

( i x ) FEATURE:
  ( A ) NAME/KEY: repeat_unit
  ( B ) LOCATION: 2218..2250

( i x ) FEATURE:
  ( A ) NAME/KEY: repeat_unit
  ( B ) LOCATION: 2251..2283

( x i ) SEQUENCE DESCRIPTION: SEQ ID NO:1:

```
ACCTTCTGTA TCAGTTAAGT GTCAAGATGG AAGGAACAGC AGTCTCAAGA TAATGCAAAG                 60

AGTTTATTCA TCCAGAGGCT G ATG CTC ACC ATG GGG CGC CTG CAA CTG GTT                  111
                       Met Leu Thr Met Gly Arg Leu Gln Leu Val
                       -23          -20                    -15

GTG TTG GGC CTC ACC TGC TGC TGG GCA GTG GCG AGT GCC GCG AAG CTG                  159
Val Leu Gly Leu Thr Cys Cys Trp Ala Val Ala Ser Ala Ala Lys Leu
            -10              -5                          1

GGC GCC GTG TAC ACA GAA GGT GGG TTC GTG GAA GGC GTC AAT AAG AAG                  207
Gly Ala Val Tyr Thr Glu Gly Gly Phe Val Glu Gly Val Asn Lys Lys
    5                10                  15

CTC GGC CTC CTG GGT GAC TCT GTG GAC ATC TTC AAG GGC ATC CCC TTC                  255
Leu Gly Leu Leu Gly Asp Ser Val Asp Ile Phe Lys Gly Ile Pro Phe
20                  25                  30                  35

GCA GCT CCC ACC AAG GCC CTG GAA AAT CCT CAG CCA CAT CCT GGC TGG                  303
Ala Ala Pro Thr Lys Ala Leu Glu Asn Pro Gln Pro His Pro Gly Trp
                40                  45                  50

CAA GGG ACC CTG AAG GCC AAG AAC TTC AAG AAG AGA TGC CTG CAG GCC                  351
Gln Gly Thr Leu Lys Ala Lys Asn Phe Lys Lys Arg Cys Leu Gln Ala
            55                  60                  65

ACC ATC ACC CAG GAC AGC ACC TAC GGG GAT GAA GAC TGC CTG TAC CTC                  399
Thr Ile Thr Gln Asp Ser Thr Tyr Gly Asp Glu Asp Cys Leu Tyr Leu
        70                  75                  80

AAC ATT TGG GTG CCC CAG GGC AGG AAG CAA GTC TCC CGG GAC CTG CCC                  447
Asn Ile Trp Val Pro Gln Gly Arg Lys Gln Val Ser Arg Asp Leu Pro
    85                  90                  95

GTT ATG ATC TGG ATC TAT GGA GGC GCC TTC CTC ATG GGG TCC GGC CAT                  495
Val Met Ile Trp Ile Tyr Gly Gly Ala Phe Leu Met Gly Ser Gly His
100             105                 110                 115

GGG GCC AAC TTC CTC AAC AAC TAC CTG TAT GAC GGC GAG GAG ATC GCC                  543
Gly Ala Asn Phe Leu Asn Asn Tyr Leu Tyr Asp Gly Glu Glu Ile Ala
                120                 125                 130

ACA CGC GGA AAC GTC ATC GTG GTC ACC TTC AAC TAC CGT GTC GGC CCC                  591
Thr Arg Gly Asn Val Ile Val Val Thr Phe Asn Tyr Arg Val Gly Pro
        135                 140                 145

CTT GGG TTC CTC AGC ACT GGG GAC GCC AAT CTG CCA GGT AAC TAT GGC                  639
Leu Gly Phe Leu Ser Thr Gly Asp Ala Asn Leu Pro Gly Asn Tyr Gly
    150                 155                 160

CTT CGG GAT CAG CAC ATG GCC ATT GCT TGG GTG AAG AGG AAT ATC GCG                  687
Leu Arg Asp Gln His Met Ala Ile Ala Trp Val Lys Arg Asn Ile Ala
165                 170                 175

GCC TTC GGG GGG GAC CCC AAC AAC ATC ACG CTC TTC GGG GAG TCT GCT                  735
Ala Phe Gly Gly Asp Pro Asn Asn Ile Thr Leu Phe Gly Glu Ser Ala
180                 185                 190                 195

GGA GGT GCC AGC GTC TCT CTG CAG ACC CTC TCC CCC TAC AAC AAG GGC                  783
Gly Gly Ala Ser Val Ser Leu Gln Thr Leu Ser Pro Tyr Asn Lys Gly
                200                 205                 210

CTC ATC CGG CGA GCC ATC AGC CAG AGC GGC GTG GCC CTG AGT CCC TGG                  831
Leu Ile Arg Arg Ala Ile Ser Gln Ser Gly Val Ala Leu Ser Pro Trp
        215                 220                 225

GTC ATC CAG AAA AAC CCA CTC TTC TGG GCC AAA AAG GTG GCT GAG AAG                  879
Val Ile Gln Lys Asn Pro Leu Phe Trp Ala Lys Lys Val Ala Glu Lys
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 230 |     |     |     |     | 235 |     |     |     |     | 240 |     |      |
| GTG | GGT | TGC | CCT | GTG | GGT | GAT | GCC | GCC | AGG | ATG | GCC | CAG | TGT | CTG | AAG | 927  |
| Val | Gly | Cys | Pro | Val | Gly | Asp | Ala | Ala | Arg | Met | Ala | Gln | Cys | Leu | Lys |      |
|     | 245 |     |     |     | 250 |     |     |     |     | 255 |     |     |     |     |     |      |
| GTT | ACT | GAT | CCC | CGA | GCC | CTG | ACG | CTG | GCC | TAT | AAG | GTG | CCG | CTG | GCA | 975  |
| Val | Thr | Asp | Pro | Arg | Ala | Leu | Thr | Leu | Ala | Tyr | Lys | Val | Pro | Leu | Ala |      |
| 260 |     |     |     |     | 265 |     |     |     |     | 270 |     |     |     |     | 275 |      |
| GGC | CTG | GAG | TAC | CCC | ATG | CTG | CAC | TAT | GTG | GGC | TTC | GTC | CCT | GTC | ATT | 1023 |
| Gly | Leu | Glu | Tyr | Pro | Met | Leu | His | Tyr | Val | Gly | Phe | Val | Pro | Val | Ile |      |
|     |     |     |     | 280 |     |     |     |     | 285 |     |     |     |     | 290 |     |      |
| GAT | GGA | GAC | TTC | ATC | CCC | GCT | GAC | CCG | ATC | AAC | CTG | TAC | GCC | AAC | GCC | 1071 |
| Asp | Gly | Asp | Phe | Ile | Pro | Ala | Asp | Pro | Ile | Asn | Leu | Tyr | Ala | Asn | Ala |      |
|     |     |     | 295 |     |     |     |     | 300 |     |     |     |     | 305 |     |     |      |
| GCC | GAC | ATC | GAC | TAT | ATA | GCA | GGC | ACC | AAC | AAC | ATG | GAC | GGC | CAC | ATC | 1119 |
| Ala | Asp | Ile | Asp | Tyr | Ile | Ala | Gly | Thr | Asn | Asn | Met | Asp | Gly | His | Ile |      |
|     |     | 310 |     |     |     |     | 315 |     |     |     |     | 320 |     |     |     |      |
| TTC | GCC | AGC | ATC | GAC | ATG | CCT | GCC | ATC | AAC | AAG | GGC | AAC | AAG | AAA | GTC | 1167 |
| Phe | Ala | Ser | Ile | Asp | Met | Pro | Ala | Ile | Asn | Lys | Gly | Asn | Lys | Lys | Val |      |
|     | 325 |     |     |     |     | 330 |     |     |     |     | 335 |     |     |     |     |      |
| ACG | GAG | GAG | GAC | TTC | TAC | AAG | CTG | GTC | AGT | GAG | TTC | ACA | ATC | ACC | AAG | 1215 |
| Thr | Glu | Glu | Asp | Phe | Tyr | Lys | Leu | Val | Ser | Glu | Phe | Thr | Ile | Thr | Lys |      |
| 340 |     |     |     |     | 345 |     |     |     |     | 350 |     |     |     |     | 355 |      |
| GGG | CTC | AGA | GGC | GCC | AAG | ACG | ACC | TTT | GAT | GTC | TAC | ACC | GAG | TCC | TGG | 1263 |
| Gly | Leu | Arg | Gly | Ala | Lys | Thr | Thr | Phe | Asp | Val | Tyr | Thr | Glu | Ser | Trp |      |
|     |     |     |     | 360 |     |     |     |     | 365 |     |     |     |     | 370 |     |      |
| GCC | CAG | GAC | CCA | TCC | CAG | GAG | AAT | AAG | AAG | AAG | ACT | GTG | GTG | GAC | TTT | 1311 |
| Ala | Gln | Asp | Pro | Ser | Gln | Glu | Asn | Lys | Lys | Lys | Thr | Val | Val | Asp | Phe |      |
|     |     |     | 375 |     |     |     |     | 380 |     |     |     |     | 385 |     |     |      |
| GAG | ACC | GAT | GTC | CTC | TTC | CTG | GTG | CCC | ACC | GAG | ATT | GCC | CTA | GCC | CAG | 1359 |
| Glu | Thr | Asp | Val | Leu | Phe | Leu | Val | Pro | Thr | Glu | Ile | Ala | Leu | Ala | Gln |      |
|     |     | 390 |     |     |     |     | 395 |     |     |     |     | 400 |     |     |     |      |
| CAC | AGA | GCC | AAT | GCC | AAG | AGT | GCC | AAG | ACC | TAC | GCC | TAC | CTG | TTT | TCC | 1407 |
| His | Arg | Ala | Asn | Ala | Lys | Ser | Ala | Lys | Thr | Tyr | Ala | Tyr | Leu | Phe | Ser |      |
|     | 405 |     |     |     |     | 410 |     |     |     |     | 415 |     |     |     |     |      |
| CAT | CCC | TCT | CGG | ATG | CCC | GTC | TAC | CCC | AAA | TGG | GTG | GGG | GCC | GAC | CAT | 1455 |
| His | Pro | Ser | Arg | Met | Pro | Val | Tyr | Pro | Lys | Trp | Val | Gly | Ala | Asp | His |      |
| 420 |     |     |     |     | 425 |     |     |     |     | 430 |     |     |     |     | 435 |      |
| GCA | GAT | GAC | ATT | CAG | TAC | GTT | TTC | GGG | AAG | CCC | TTC | GCC | ACC | CCC | ACG | 1503 |
| Ala | Asp | Asp | Ile | Gln | Tyr | Val | Phe | Gly | Lys | Pro | Phe | Ala | Thr | Pro | Thr |      |
|     |     |     | 440 |     |     |     |     | 445 |     |     |     |     | 450 |     |     |      |
| GGC | TAC | CGG | CCC | CAA | GAC | AGG | ACA | GTC | TCT | AAG | GCC | ATG | ATC | GCC | TAC | 1551 |
| Gly | Tyr | Arg | Pro | Gln | Asp | Arg | Thr | Val | Ser | Lys | Ala | Met | Ile | Ala | Tyr |      |
|     |     | 455 |     |     |     |     | 460 |     |     |     |     | 465 |     |     |     |      |
| TGG | ACC | AAC | TTT | GCC | AAA | ACA | GGG | GAC | CCC | AAC | ATG | GGC | GAC | TCG | GCT | 1599 |
| Trp | Thr | Asn | Phe | Ala | Lys | Thr | Gly | Asp | Pro | Asn | Met | Gly | Asp | Ser | Ala |      |
|     | 470 |     |     |     |     | 475 |     |     |     |     | 480 |     |     |     |     |      |
| GTG | CCC | ACA | CAC | TGG | GAA | CCC | TAC | ACT | ACG | GAA | AAC | AGC | GGC | TAC | CTG | 1647 |
| Val | Pro | Thr | His | Trp | Glu | Pro | Tyr | Thr | Thr | Glu | Asn | Ser | Gly | Tyr | Leu |      |
| 485 |     |     |     |     | 490 |     |     |     |     | 495 |     |     |     |     |     |      |
| GAG | ATC | ACC | AAG | AAG | ATG | GGC | AGC | AGC | TCC | ATG | AAG | CGG | AGC | CTG | AGA | 1695 |
| Glu | Ile | Thr | Lys | Lys | Met | Gly | Ser | Ser | Ser | Met | Lys | Arg | Ser | Leu | Arg |      |
| 500 |     |     |     |     | 505 |     |     |     |     | 510 |     |     |     |     | 515 |      |
| ACC | AAC | TTC | CTG | CGC | TAC | TGG | ACC | CTC | ACC | TAT | CTG | GCG | CTG | CCC | ACA | 1743 |
| Thr | Asn | Phe | Leu | Arg | Tyr | Trp | Thr | Leu | Thr | Tyr | Leu | Ala | Leu | Pro | Thr |      |
|     |     |     |     | 520 |     |     |     |     | 525 |     |     |     |     | 530 |     |      |
| GTG | ACC | GAC | CAG | GAG | GCC | ACC | CCT | GTG | CCC | CCC | ACA | GGG | GAC | TCC | GAG | 1791 |
| Val | Thr | Asp | Gln | Glu | Ala | Thr | Pro | Val | Pro | Pro | Thr | Gly | Asp | Ser | Glu |      |
|     |     |     | 535 |     |     |     |     | 540 |     |     |     |     | 545 |     |     |      |
| GCC | ACT | CCC | GTG | CCC | CCC | ACG | GGT | GAC | TCC | GAG | ACC | GCC | CCC | GTG | CCG | 1839 |
| Ala | Thr | Pro | Val | Pro | Pro | Thr | Gly | Asp | Ser | Glu | Thr | Ala | Pro | Val | Pro |      |

| | | | | | | | | | | | | | | | | |
|---|---|---|---|---|---|---|---|---|---|---|---|---|---|---|---|---|
| | | | 550 | | | | | 555 | | | | | 560 | | | |
| CCC | ACG | GGT | GAC | TCC | GGG | GCC | CCC | CCC | GTG | CCG | CCC | ACG | GGT | GAC | TCC | 1887 |
| Pro | Thr | Gly | Asp | Ser | Gly | Ala | Pro | Pro | Val | Pro | Pro | Thr | Gly | Asp | Ser | |
| | 565 | | | | | 570 | | | | | 575 | | | | | |
| GGG | GCC | CCC | CCC | GTG | CCG | CCC | ACG | GGT | GAC | TCC | GGG | GCC | CCC | CCC | GTG | 1935 |
| Gly | Ala | Pro | Pro | Val | Pro | Pro | Thr | Gly | Asp | Ser | Gly | Ala | Pro | Pro | Val | |
| 580 | | | | | 585 | | | | | 590 | | | | | 595 | |
| CCG | CCC | ACG | GGT | GAC | TCC | GGG | GCC | CCC | CCC | GTG | CCG | CCC | ACG | GGT | GAC | 1983 |
| Pro | Pro | Thr | Gly | Asp | Ser | Gly | Ala | Pro | Pro | Val | Pro | Pro | Thr | Gly | Asp | |
| | | | | 600 | | | | | 605 | | | | | 610 | | |
| TCC | GGG | GCC | CCC | CCC | GTG | CCG | CCC | ACG | GGT | GAC | TCC | GGG | GCC | CCC | CCC | 2031 |
| Ser | Gly | Ala | Pro | Pro | Val | Pro | Pro | Thr | Gly | Asp | Ser | Gly | Ala | Pro | Pro | |
| | | | 615 | | | | | 620 | | | | | 625 | | | |
| GTG | CCG | CCC | ACG | GGT | GAC | TCC | GGC | GCC | CCC | CCC | GTG | CCG | CCC | ACG | GGT | 2079 |
| Val | Pro | Pro | Thr | Gly | Asp | Ser | Gly | Ala | Pro | Pro | Val | Pro | Pro | Thr | Gly | |
| | | 630 | | | | | 635 | | | | | 640 | | | | |
| GAC | GCC | GGG | CCC | CCC | CCC | GTG | CCG | CCC | ACG | GGT | GAC | TCC | GGC | GCC | CCC | 2127 |
| Asp | Ala | Gly | Pro | Pro | Pro | Val | Pro | Pro | Thr | Gly | Asp | Ser | Gly | Ala | Pro | |
| | 645 | | | | | 650 | | | | | 655 | | | | | |
| CCC | GTG | CCG | CCC | ACG | GGT | GAC | TCC | GGG | GCC | CCC | CCC | GTG | ACC | CCC | ACG | 2175 |
| Pro | Val | Pro | Pro | Thr | Gly | Asp | Ser | Gly | Ala | Pro | Pro | Val | Thr | Pro | Thr | |
| 660 | | | | | 665 | | | | | 670 | | | | | 675 | |
| GGT | GAC | TCC | GAG | ACC | GCC | CCC | GTG | CCG | CCC | ACG | GGT | GAC | TCC | GGG | GCC | 2223 |
| Gly | Asp | Ser | Glu | Thr | Ala | Pro | Val | Pro | Pro | Thr | Gly | Asp | Ser | Gly | Ala | |
| | | | | 680 | | | | | 685 | | | | | 690 | | |
| CCC | CCT | GTG | CCC | CCC | ACG | GGT | GAC | TCT | GAG | GCT | GCC | CCT | GTG | CCC | CCC | 2271 |
| Pro | Pro | Val | Pro | Pro | Thr | Gly | Asp | Ser | Glu | Ala | Ala | Pro | Val | Pro | Pro | |
| | | | 695 | | | | | 700 | | | | | 705 | | | |
| ACA | GAT | GAC | TCC | AAG | GAA | GCT | CAG | ATG | CCT | GCA | GTC | ATT | AGG | TTT | | |
| Thr | Asp | Asp | Ser | Lys | Glu | Ala | Gln | Met | Pro | Ala | Val | Ile | Arg | Phe | | |
| | | 710 | | | | | 715 | | | | | 720 | | | | |
| | | | | | | | | | | | | | | TAGCGTCCA | | 2326 |

TGAGCCTTGG TATCAAGAGG CCACAAGAGT GGGACCCCAG GGGCTCCCCT CCCATCTTGA      2386

GCTCTTCCTG AATAAAGCCT CATACCCCTA AAAAAAAAA AA                         2428

( 2 ) INFORMATION FOR SEQ ID NO:2:

( i ) SEQUENCE CHARACTERISTICS:
        ( A ) LENGTH: 745 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Leu | Thr | Met | Gly | Arg | Leu | Gln | Leu | Val | Val | Leu | Gly | Leu | Thr | Cys |
|---|---|---|---|---|---|---|---|---|---|---|---|---|---|---|---|
| -23 | | -20 | | | | | -15 | | | | | -10 | | | |
| Cys | Trp | Ala | Val | Ala | Ser | Ala | Ala | Lys | Leu | Gly | Ala | Val | Tyr | Thr | Glu |
| | -5 | | | | | 1 | | | | 5 | | | | | |
| Gly | Gly | Phe | Val | Glu | Gly | Val | Asn | Lys | Lys | Leu | Gly | Leu | Leu | Gly | Asp |
| 10 | | | | 15 | | | | 20 | | | | | | | 25 |
| Ser | Val | Asp | Ile | Phe | Lys | Gly | Ile | Pro | Phe | Ala | Ala | Pro | Thr | Lys | Ala |
| | | | 30 | | | | 35 | | | | | | | 40 | |
| Leu | Glu | Asn | Pro | Gln | Pro | His | Pro | Gly | Trp | Gln | Gly | Thr | Leu | Lys | Ala |
| | | | 45 | | | 50 | | | | 55 | | | | | |
| Lys | Asn | Phe | Lys | Lys | Arg | Cys | Leu | Gln | Ala | Thr | Ile | Thr | Gln | Asp | Ser |
| | | 60 | | | | 65 | | | | 70 | | | | | |
| Thr | Tyr | Gly | Asp | Glu | Asp | Cys | Leu | Tyr | Leu | Asn | Ile | Trp | Val | Pro | Gln |
| 75 | | | | 80 | | | | | 85 | | | | | | |

```
Gly Arg Lys Gln Val Ser Arg Asp Leu Pro Val Met Ile Trp Ile Tyr
 90              95                 100                 105
Gly Gly Ala Phe Leu Met Gly Ser Gly His Gly Ala Asn Phe Leu Asn
                110                 115                 120
Asn Tyr Leu Tyr Asp Gly Glu Glu Ile Ala Thr Arg Gly Asn Val Ile
                125                 130                 135
Val Val Thr Phe Asn Tyr Arg Val Gly Pro Leu Gly Phe Leu Ser Thr
        140                 145                 150
Gly Asp Ala Asn Leu Pro Gly Asn Tyr Gly Leu Arg Asp Gln His Met
        155                 160                 165
Ala Ile Ala Trp Val Lys Arg Asn Ile Ala Ala Phe Gly Gly Asp Pro
170                 175                 180                 185
Asn Asn Ile Thr Leu Phe Gly Glu Ser Ala Gly Gly Ala Ser Val Ser
                190                 195                 200
Leu Gln Thr Leu Ser Pro Tyr Asn Lys Gly Leu Ile Arg Arg Ala Ile
                205                 210                 215
Ser Gln Ser Gly Val Ala Leu Ser Pro Trp Val Ile Gln Lys Asn Pro
        220                 225                 230
Leu Phe Trp Ala Lys Lys Val Ala Glu Lys Val Gly Cys Pro Val Gly
        235                 240                 245
Asp Ala Ala Arg Met Ala Gln Cys Leu Lys Val Thr Asp Pro Arg Ala
250                 255                 260                 265
Leu Thr Leu Ala Tyr Lys Val Pro Leu Ala Gly Leu Glu Tyr Pro Met
                270                 275                 280
Leu His Tyr Val Gly Phe Val Pro Val Ile Asp Gly Asp Phe Ile Pro
        285                 290                 295
Ala Asp Pro Ile Asn Leu Tyr Ala Asn Ala Ala Asp Ile Asp Tyr Ile
        300                 305                 310
Ala Gly Thr Asn Asn Met Asp Gly His Ile Phe Ala Ser Ile Asp Met
        315                 320                 325
Pro Ala Ile Asn Lys Gly Asn Lys Lys Val Thr Glu Glu Asp Phe Tyr
330                 335                 340                 345
Lys Leu Val Ser Glu Phe Thr Ile Thr Lys Gly Leu Arg Gly Ala Lys
                350                 355                 360
Thr Thr Phe Asp Val Tyr Thr Glu Ser Trp Ala Gln Asp Pro Ser Gln
                365                 370                 375
Glu Asn Lys Lys Lys Thr Val Val Asp Phe Glu Thr Asp Val Leu Phe
        380                 385                 390
Leu Val Pro Thr Glu Ile Ala Leu Ala Gln His Arg Ala Asn Ala Lys
        395                 400                 405
Ser Ala Lys Thr Tyr Ala Tyr Leu Phe Ser His Pro Ser Arg Met Pro
410                 415                 420                 425
Val Tyr Pro Lys Trp Val Gly Ala Asp His Ala Asp Asp Ile Gln Tyr
                430                 435                 440
Val Phe Gly Lys Pro Phe Ala Thr Pro Thr Gly Tyr Arg Pro Gln Asp
                445                 450                 455
Arg Thr Val Ser Lys Ala Met Ile Ala Tyr Trp Thr Asn Phe Ala Lys
        460                 465                 470
Thr Gly Asp Pro Asn Met Gly Asp Ser Ala Val Pro Thr His Trp Glu
        475                 480                 485
Pro Tyr Thr Thr Glu Asn Ser Gly Tyr Leu Glu Ile Thr Lys Lys Met
490                 495                 500                 505
Gly Ser Ser Ser Met Lys Arg Ser Leu Arg Thr Asn Phe Leu Arg Tyr
                510                 515                 520
```

```
Trp Thr Leu Thr Tyr Leu Ala Leu Pro Thr Val Thr Asp Gln Glu Ala
            525             530                 535

Thr Pro Val Pro Pro Thr Gly Asp Ser Glu Ala Thr Pro Val Pro Pro
        540             545                 550

Thr Gly Asp Ser Glu Thr Ala Pro Val Pro Pro Thr Gly Asp Ser Gly
    555                 560                 565

Ala Pro Pro Val Pro Pro Thr Gly Asp Ser Gly Ala Pro Pro Val Pro
570             575                 580                     585

Pro Thr Gly Asp Ser Gly Ala Pro Pro Pro Pro Thr Gly Asp Ser
        590                     595                     600

Gly Ala Pro Pro Val Pro Pro Thr Gly Asp Ser Gly Ala Pro Pro Val
            605                 610                 615

Pro Pro Thr Gly Asp Ser Gly Ala Pro Pro Val Pro Pro Thr Gly Asp
        620                 625                 630

Ser Gly Ala Pro Pro Val Pro Thr Gly Asp Ala Gly Pro Pro Pro
    635                 640                 645

Val Pro Pro Thr Gly Asp Ser Gly Ala Pro Pro Val Pro Pro Thr Gly
650                 655                 660                 665

Asp Ser Gly Ala Pro Pro Val Thr Pro Thr Gly Asp Ser Glu Thr Ala
                670                 675                 680

Pro Val Pro Pro Thr Gly Asp Ser Gly Ala Pro Pro Val Pro Pro Thr
            685                 690                 695

Gly Asp Ser Glu Ala Ala Pro Val Pro Pro Thr Asp Asp Ser Lys Glu
        700                 705                 710

Ala Gln Met Pro Ala Val Ile Arg Phe
        715                 720
```

( 2 ) INFORMATION FOR SEQ ID NO:3:

( i ) SEQUENCE CHARACTERISTICS:
        ( A ) LENGTH: 722 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Homo sapiens
        ( F ) TISSUE TYPE: Mammary gland ( x i ) SEQUENCE DESCRIPTION: SEQ ID NO:3:

```
Ala Lys Leu Gly Ala Val Tyr Thr Glu Gly Gly Phe Val Glu Gly Val
1               5               10                  15

Asn Lys Lys Leu Gly Leu Leu Gly Asp Ser Val Asp Ile Phe Lys Gly
            20              25                  30

Ile Pro Phe Ala Ala Pro Thr Lys Ala Leu Glu Asn Pro Gln Pro His
        35              40                  45

Pro Gly Trp Gln Gly Thr Leu Lys Ala Lys Asn Phe Lys Lys Arg Cys
    50              55                  60

Leu Gln Ala Thr Ile Thr Gln Asp Ser Thr Tyr Gly Asp Glu Asp Cys
65              70              75                  80

Leu Tyr Leu Asn Ile Trp Val Pro Gln Gly Arg Lys Gln Val Ser Arg
                85              90                  95

Asp Leu Pro Val Met Ile Trp Ile Tyr Gly Gly Ala Phe Leu Met Gly
            100             105                 110

Ser Gly His Gly Ala Asn Phe Leu Asn Asn Tyr Leu Tyr Asp Gly Glu
```

-continued

```
            115                        120                              125
 Glu  Ile  Ala  Thr  Arg  Gly  Asn  Val  Ile  Val  Val  Thr  Phe  Asn  Tyr  Arg
            130                        135                     140
 Val  Gly  Pro  Leu  Gly  Phe  Leu  Ser  Thr  Gly  Asp  Ala  Asn  Leu  Pro  Gly
 145                        150                        155                     160
 Asn  Tyr  Gly  Leu  Arg  Asp  Gln  His  Met  Ala  Ile  Ala  Trp  Val  Lys  Arg
                      165                       170                       175
 Asn  Ile  Ala  Ala  Phe  Gly  Gly  Asp  Pro  Asn  Asn  Ile  Thr  Leu  Phe  Gly
                 180                       185                      190
 Glu  Ser  Ala  Gly  Gly  Ala  Ser  Val  Ser  Leu  Gln  Thr  Leu  Ser  Pro  Tyr
            195                      200                      205
 Asn  Lys  Gly  Leu  Ile  Arg  Arg  Ala  Ile  Ser  Gln  Ser  Gly  Val  Ala  Leu
       210                      215                      220
 Ser  Pro  Trp  Val  Ile  Gln  Lys  Asn  Pro  Leu  Phe  Trp  Ala  Lys  Lys  Val
 225                      230                      235                         240
 Ala  Glu  Lys  Val  Gly  Cys  Pro  Val  Gly  Asp  Ala  Ala  Arg  Met  Ala  Gln
                      245                      250                           255
 Cys  Leu  Lys  Val  Thr  Asp  Pro  Arg  Ala  Leu  Thr  Leu  Ala  Tyr  Lys  Val
                 260                      265                        270
 Pro  Leu  Ala  Gly  Leu  Glu  Tyr  Pro  Met  Leu  His  Tyr  Val  Gly  Phe  Val
            275                      280                       285
 Pro  Val  Ile  Asp  Gly  Asp  Phe  Ile  Pro  Ala  Asp  Pro  Ile  Asn  Leu  Tyr
       290                      295                      300
 Ala  Asn  Ala  Ala  Asp  Ile  Asp  Tyr  Ile  Ala  Gly  Thr  Asn  Asn  Met  Asp
 305                      310                      315                         320
 Gly  His  Ile  Phe  Ala  Ser  Ile  Asp  Met  Pro  Ala  Ile  Asn  Lys  Gly  Asn
                      325                      330                           335
 Lys  Lys  Val  Thr  Glu  Glu  Asp  Phe  Tyr  Lys  Leu  Val  Ser  Glu  Phe  Thr
                 340                      345                        350
 Ile  Thr  Lys  Gly  Leu  Arg  Gly  Ala  Lys  Thr  Thr  Phe  Asp  Val  Tyr  Thr
            355                      360                       365
 Glu  Ser  Trp  Ala  Gln  Asp  Pro  Ser  Gln  Glu  Asn  Lys  Lys  Lys  Thr  Val
       370                      375                      380
 Val  Asp  Phe  Glu  Thr  Asp  Val  Leu  Phe  Leu  Val  Pro  Thr  Glu  Ile  Ala
 385                      390                      395                         400
 Leu  Ala  Gln  His  Arg  Ala  Asn  Ala  Lys  Ser  Ala  Lys  Thr  Tyr  Ala  Tyr
                      405                      410                           415
 Leu  Phe  Ser  His  Pro  Ser  Arg  Met  Pro  Val  Tyr  Pro  Lys  Trp  Val  Gly
                 420                      425                        430
 Ala  Asp  His  Ala  Asp  Asp  Ile  Gln  Tyr  Val  Phe  Gly  Lys  Pro  Phe  Ala
            435                      440                       445
 Thr  Pro  Thr  Gly  Tyr  Arg  Pro  Gln  Asp  Arg  Thr  Val  Ser  Lys  Ala  Met
       450                      455                      460
 Ile  Ala  Tyr  Trp  Thr  Asn  Phe  Ala  Lys  Thr  Gly  Asp  Pro  Asn  Met  Gly
 465                      470                      475                         480
 Asp  Ser  Ala  Val  Pro  Thr  His  Trp  Glu  Pro  Tyr  Thr  Thr  Glu  Asn  Ser
                      485                      490                           495
 Gly  Tyr  Leu  Glu  Ile  Thr  Lys  Lys  Met  Gly  Ser  Ser  Ser  Met  Lys  Arg
                 500                      505                        510
 Ser  Leu  Arg  Thr  Asn  Phe  Leu  Arg  Tyr  Trp  Thr  Leu  Thr  Tyr  Leu  Ala
            515                      520                       525
 Leu  Pro  Thr  Val  Thr  Asp  Gln  Glu  Ala  Thr  Pro  Val  Pro  Pro  Thr  Gly
       530                      535                      540
```

-continued

```
Asp  Ser  Glu  Ala  Thr  Pro  Val  Pro  Pro  Thr  Gly  Asp  Ser  Glu  Thr  Ala
545                      550                     555                         560

Pro  Val  Pro  Pro  Thr  Gly  Asp  Ser  Gly  Ala  Pro  Pro  Val  Pro  Pro  Thr
                    565                     570                          575

Gly  Asp  Ser  Gly  Ala  Pro  Pro  Val  Pro  Pro  Thr  Gly  Asp  Ser  Gly  Ala
               580                     585                         590

Pro  Pro  Val  Pro  Pro  Thr  Gly  Asp  Ser  Gly  Ala  Pro  Pro  Val  Pro  Pro
          595                     600                     605

Thr  Gly  Asp  Ser  Gly  Ala  Pro  Pro  Val  Pro  Pro  Thr  Gly  Asp  Ser  Gly
     610                     615                     620

Ala  Pro  Pro  Val  Pro  Pro  Thr  Gly  Asp  Ser  Gly  Ala  Pro  Pro  Val  Pro
625                      630                     635                         640

Pro  Thr  Gly  Asp  Ala  Gly  Pro  Pro  Pro  Val  Pro  Pro  Thr  Gly  Asp  Ser
               645                          650                          655

Gly  Ala  Pro  Pro  Val  Pro  Pro  Thr  Gly  Asp  Ser  Gly  Ala  Pro  Pro  Val
               660                     665                     670

Thr  Pro  Thr  Gly  Asp  Ser  Glu  Thr  Ala  Pro  Val  Pro  Pro  Thr  Gly  Asp
          675                     680                     685

Ser  Gly  Ala  Pro  Pro  Val  Pro  Pro  Thr  Gly  Asp  Ser  Glu  Ala  Ala  Pro
690                      695                     700

Val  Pro  Pro  Thr  Asp  Asp  Ser  Lys  Glu  Ala  Gln  Met  Pro  Ala  Val  Ile
705                 710                     715                              720

Arg  Phe
```

( 2 ) INFORMATION FOR SEQ ID NO:4:

( i ) SEQUENCE CHARACTERISTICS:
        ( A ) LENGTH: 535 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Homo sapiens
        ( F ) TISSUE TYPE: Mammary gland ( i x ) FEATURE:
        ( A ) NAME/KEY: Peptide
        ( B ) LOCATION: 1..535
        ( D ) OTHER INFORMATION: /label= Variant_A ( x i ) SEQUENCE DESCRIPTION: SEQ ID NO:4:

```
Ala  Lys  Leu  Gly  Ala  Val  Tyr  Thr  Glu  Gly  Gly  Phe  Val  Glu  Gly  Val
1                   5                   10                      15

Asn  Lys  Lys  Leu  Gly  Leu  Leu  Gly  Asp  Ser  Val  Asp  Ile  Phe  Lys  Gly
               20                      25                      30

Ile  Pro  Phe  Ala  Ala  Pro  Thr  Lys  Ala  Leu  Glu  Asn  Pro  Gln  Pro  His
          35                      40                      45

Pro  Gly  Trp  Gln  Gly  Thr  Leu  Lys  Ala  Lys  Asn  Phe  Lys  Lys  Arg  Cys
     50                      55                      60

Leu  Gln  Ala  Thr  Ile  Thr  Gln  Asp  Ser  Thr  Tyr  Gly  Asp  Glu  Asp  Cys
65                       70                     75                          80

Leu  Tyr  Leu  Asn  Ile  Trp  Val  Pro  Gln  Gly  Arg  Lys  Gln  Val  Ser  Arg
               85                      90                      95

Asp  Leu  Pro  Val  Met  Ile  Trp  Ile  Tyr  Gly  Gly  Ala  Phe  Leu  Met  Gly
               100                     105                     110

Ser  Gly  His  Gly  Ala  Asn  Phe  Leu  Asn  Asn  Tyr  Leu  Tyr  Asp  Gly  Glu
```

```
                 115                           120                           125
      Glu  Ile  Ala  Thr  Arg  Gly  Asn  Val  Ile  Val  Val  Thr  Phe  Asn  Tyr  Arg
                 130                           135                           140
      Val  Gly  Pro  Leu  Gly  Phe  Leu  Ser  Thr  Gly  Asp  Ala  Asn  Leu  Pro  Gly
      145                           150                           155                 160
      Asn  Tyr  Gly  Leu  Arg  Asp  Gln  His  Met  Ala  Ile  Ala  Trp  Val  Lys  Arg
                      165                           170                           175
      Asn  Ile  Ala  Ala  Phe  Gly  Gly  Asp  Pro  Asn  Asn  Ile  Thr  Leu  Phe  Gly
                      180                           185                           190
      Glu  Ser  Ala  Gly  Gly  Ala  Ser  Val  Ser  Leu  Gln  Thr  Leu  Ser  Pro  Tyr
                 195                           200                           205
      Asn  Lys  Gly  Leu  Ile  Arg  Arg  Ala  Ile  Ser  Gln  Ser  Gly  Val  Ala  Leu
                 210                           215                           220
      Ser  Pro  Trp  Val  Ile  Gln  Lys  Asn  Pro  Leu  Phe  Trp  Ala  Lys  Lys  Val
      225                           230                           235                 240
      Ala  Glu  Lys  Val  Gly  Cys  Pro  Val  Gly  Asp  Ala  Ala  Arg  Met  Ala  Gln
                           245                           250                           255
      Cys  Leu  Lys  Val  Thr  Asp  Pro  Arg  Ala  Leu  Thr  Leu  Ala  Tyr  Lys  Val
                           260                           265                           270
      Pro  Leu  Ala  Gly  Leu  Glu  Tyr  Pro  Met  Leu  His  Tyr  Val  Gly  Phe  Val
                 275                           280                           285
      Pro  Val  Ile  Asp  Gly  Asp  Phe  Ile  Pro  Ala  Asp  Pro  Ile  Asn  Leu  Tyr
           290                           295                           300
      Ala  Asn  Ala  Ala  Asp  Ile  Asp  Tyr  Ile  Ala  Gly  Thr  Asn  Asn  Met  Asp
      305                           310                           315                 320
      Gly  His  Ile  Phe  Ala  Ser  Ile  Asp  Met  Pro  Ala  Ile  Asn  Lys  Gly  Asn
                           325                           330                           335
      Lys  Lys  Val  Thr  Glu  Glu  Asp  Phe  Tyr  Lys  Leu  Val  Ser  Glu  Phe  Thr
                      340                           345                           350
      Ile  Thr  Lys  Gly  Leu  Arg  Gly  Ala  Lys  Thr  Thr  Phe  Asp  Val  Tyr  Thr
                 355                           360                           365
      Glu  Ser  Trp  Ala  Gln  Asp  Pro  Ser  Gln  Glu  Asn  Lys  Lys  Lys  Thr  Val
           370                           375                           380
      Val  Asp  Phe  Glu  Thr  Asp  Val  Leu  Phe  Leu  Val  Pro  Thr  Glu  Ile  Ala
      385                           390                           395                 400
      Leu  Ala  Gln  His  Arg  Ala  Asn  Ala  Lys  Ser  Ala  Lys  Thr  Tyr  Ala  Tyr
                           405                           410                           415
      Leu  Phe  Ser  His  Pro  Ser  Arg  Met  Pro  Val  Tyr  Pro  Lys  Trp  Val  Gly
                      420                           425                           430
      Ala  Asp  His  Ala  Asp  Asp  Ile  Gln  Tyr  Val  Phe  Gly  Lys  Pro  Phe  Ala
                      435                           440                           445
      Thr  Pro  Thr  Gly  Tyr  Arg  Pro  Gln  Asp  Arg  Thr  Val  Ser  Lys  Ala  Met
           450                           455                           460
      Ile  Ala  Tyr  Trp  Thr  Asn  Phe  Ala  Lys  Thr  Gly  Asp  Pro  Asn  Met  Gly
      465                           470                           475                 480
      Asp  Ser  Ala  Val  Pro  Thr  His  Trp  Glu  Pro  Tyr  Thr  Thr  Glu  Asn  Ser
                           485                           490                           495
      Gly  Tyr  Leu  Glu  Ile  Thr  Lys  Lys  Met  Gly  Ser  Ser  Ser  Met  Lys  Arg
                      500                           505                           510
      Ser  Leu  Arg  Thr  Asn  Phe  Leu  Arg  Tyr  Trp  Thr  Leu  Thr  Tyr  Leu  Ala
                 515                           520                           525
      Leu  Pro  Thr  Val  Thr  Asp  Gln
           530                      535
```

( 2 ) INFORMATION FOR SEQ ID NO:5:

( i ) SEQUENCE CHARACTERISTICS:
        ( A ) LENGTH: 546 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Homo sapiens
        ( F ) TISSUE TYPE: Mammary gland ( i x ) FEATURE:
        ( A ) NAME/KEY: Peptide
        ( B ) LOCATION: 1..546
        ( D ) OTHER INFORMATION: /label= Variant_B ( x i ) SEQUENCE DESCRIPTION: SEQ ID NO:5:

```
Ala Lys Leu Gly Ala Val Tyr Thr Glu Gly Gly Phe Val Glu Gly Val
 1               5                  10                  15

Asn Lys Lys Leu Gly Leu Leu Gly Asp Ser Val Asp Ile Phe Lys Gly
            20                  25                  30

Ile Pro Phe Ala Ala Pro Thr Lys Ala Leu Glu Asn Pro Gln Pro His
        35                  40                  45

Pro Gly Trp Gln Gly Thr Leu Lys Ala Lys Asn Phe Lys Lys Arg Cys
    50                  55                  60

Leu Gln Ala Thr Ile Thr Gln Asp Ser Thr Tyr Gly Asp Glu Asp Cys
65                  70                  75                  80

Leu Tyr Leu Asn Ile Trp Val Pro Gln Gly Arg Lys Gln Val Ser Arg
                85                  90                  95

Asp Leu Pro Val Met Ile Trp Ile Tyr Gly Gly Ala Phe Leu Met Gly
            100                 105                 110

Ser Gly His Gly Ala Asn Phe Leu Asn Asn Tyr Leu Tyr Asp Gly Glu
        115                 120                 125

Glu Ile Ala Thr Arg Gly Asn Val Ile Val Val Thr Phe Asn Tyr Arg
    130                 135                 140

Val Gly Pro Leu Gly Phe Leu Ser Thr Gly Asp Ala Asn Leu Pro Gly
145                 150                 155                 160

Asn Tyr Gly Leu Arg Asp Gln His Met Ala Ile Ala Trp Val Lys Arg
                165                 170                 175

Asn Ile Ala Ala Phe Gly Gly Asp Pro Asn Asn Ile Thr Leu Phe Gly
            180                 185                 190

Glu Ser Ala Gly Gly Ala Ser Val Ser Leu Gln Thr Leu Ser Pro Tyr
        195                 200                 205

Asn Lys Gly Leu Ile Arg Arg Ala Ile Ser Gln Ser Gly Val Ala Leu
    210                 215                 220

Ser Pro Trp Val Ile Gln Lys Asn Pro Leu Phe Trp Ala Lys Lys Val
225                 230                 235                 240

Ala Glu Lys Val Gly Cys Pro Val Gly Asp Ala Ala Arg Met Ala Gln
                245                 250                 255

Cys Leu Lys Val Thr Asp Pro Arg Ala Leu Thr Leu Ala Tyr Lys Val
            260                 265                 270

Pro Leu Ala Gly Leu Glu Tyr Pro Met Leu His Tyr Val Gly Phe Val
        275                 280                 285

Pro Val Ile Asp Gly Asp Phe Ile Pro Ala Asp Pro Ile Asn Leu Tyr
    290                 295                 300
```

-continued

```
Ala  Asn  Ala  Ala  Asp  Ile  Asp  Tyr  Ile  Ala  Gly  Thr  Asn  Asn  Met  Asp
305                 310                      315                          320

Gly  His  Ile  Phe  Ala  Ser  Ile  Asp  Met  Pro  Ala  Ile  Asn  Lys  Gly  Asn
               325                      330                      335

Lys  Lys  Val  Thr  Glu  Glu  Asp  Phe  Tyr  Lys  Leu  Val  Ser  Glu  Phe  Thr
                340                      345                      350

Ile  Thr  Lys  Gly  Leu  Arg  Gly  Ala  Lys  Thr  Thr  Phe  Asp  Val  Tyr  Thr
          355                      360                      365

Glu  Ser  Trp  Ala  Gln  Asp  Pro  Ser  Gln  Glu  Asn  Lys  Lys  Lys  Thr  Val
     370                      375                      380

Val  Asp  Phe  Glu  Thr  Asp  Val  Leu  Phe  Leu  Val  Pro  Thr  Glu  Ile  Ala
385                 390                      395                          400

Leu  Ala  Gln  His  Arg  Ala  Asn  Ala  Lys  Ser  Ala  Lys  Thr  Tyr  Ala  Tyr
               405                      410                      415

Leu  Phe  Ser  His  Pro  Ser  Arg  Met  Pro  Val  Tyr  Pro  Lys  Trp  Val  Gly
               420                      425                      430

Ala  Asp  His  Ala  Asp  Asp  Ile  Gln  Tyr  Val  Phe  Gly  Lys  Pro  Phe  Ala
          435                      440                      445

Thr  Pro  Thr  Gly  Tyr  Arg  Pro  Gln  Asp  Arg  Thr  Val  Ser  Lys  Ala  Met
     450                      455                      460

Ile  Ala  Tyr  Trp  Thr  Asn  Phe  Ala  Lys  Thr  Gly  Asp  Pro  Asn  Met  Gly
465                 470                      475                          480

Asp  Ser  Ala  Val  Pro  Thr  His  Trp  Glu  Pro  Tyr  Thr  Thr  Glu  Asn  Ser
                485                      490                      495

Gly  Tyr  Leu  Glu  Ile  Thr  Lys  Lys  Met  Gly  Ser  Ser  Met  Lys  Arg
               500                      505                      510

Ser  Leu  Arg  Thr  Asn  Phe  Leu  Arg  Tyr  Trp  Thr  Leu  Thr  Tyr  Leu  Ala
          515                      520                      525

Leu  Pro  Thr  Val  Thr  Asp  Gln  Lys  Glu  Ala  Gln  Met  Pro  Ala  Val  Ile
     530                      535                      540

Arg  Phe
545
```

( 2 ) INFORMATION FOR SEQ ID NO:6:

( i ) SEQUENCE CHARACTERISTICS:
        ( A ) LENGTH: 568 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Homo sapiens
        ( F ) TISSUE TYPE: Mammary gland ( i x ) FEATURE:
        ( A ) NAME/KEY: Peptide
        ( B ) LOCATION: 1..568
        ( D ) OTHER INFORMATION: /label= Variant_C ( x i ) SEQUENCE DESCRIPTION: SEQ ID NO:6:

```
Ala  Lys  Leu  Gly  Ala  Val  Tyr  Thr  Glu  Gly  Gly  Phe  Val  Glu  Gly  Val
1               5                        10                       15

Asn  Lys  Lys  Leu  Gly  Leu  Leu  Gly  Asp  Ser  Val  Asp  Ile  Phe  Lys  Gly
               20                       25                       30

Ile  Pro  Phe  Ala  Ala  Pro  Thr  Lys  Ala  Leu  Glu  Asn  Pro  Gln  Pro  His
          35                       40                       45
```

```
Pro  Gly  Trp  Gln  Gly  Thr  Leu  Lys  Ala  Lys  Asn  Phe  Lys  Lys  Arg  Cys
     50                  55                       60

Leu  Gln  Ala  Thr  Ile  Thr  Gln  Asp  Ser  Thr  Tyr  Gly  Asp  Glu  Asp  Cys
65                  70                       75                            80

Leu  Tyr  Leu  Asn  Ile  Trp  Val  Pro  Gln  Gly  Arg  Lys  Gln  Val  Ser  Arg
                    85                  90                       95

Asp  Leu  Pro  Val  Met  Ile  Trp  Ile  Tyr  Gly  Gly  Ala  Phe  Leu  Met  Gly
                    100                 105                      110

Ser  Gly  His  Gly  Ala  Asn  Phe  Leu  Asn  Asn  Tyr  Leu  Tyr  Asp  Gly  Glu
          115                      120                      125

Glu  Ile  Ala  Thr  Arg  Gly  Asn  Val  Ile  Val  Thr  Phe  Asn  Tyr  Arg
          130                 135                 140

Val  Gly  Pro  Leu  Gly  Phe  Leu  Ser  Thr  Gly  Asp  Ala  Asn  Leu  Pro  Gly
145                      150                      155                      160

Asn  Tyr  Gly  Leu  Arg  Asp  Gln  His  Met  Ala  Ile  Ala  Trp  Val  Lys  Arg
                    165                 170                           175

Asn  Ile  Ala  Ala  Phe  Gly  Gly  Asp  Pro  Asn  Asn  Ile  Thr  Leu  Phe  Gly
          180                      185                      190

Glu  Ser  Ala  Gly  Gly  Ala  Ser  Val  Ser  Leu  Gln  Thr  Leu  Ser  Pro  Tyr
          195                 200                 205

Asn  Lys  Gly  Leu  Ile  Arg  Arg  Ala  Ile  Ser  Gln  Ser  Gly  Val  Ala  Leu
210                      215                      220

Ser  Pro  Trp  Val  Ile  Gln  Lys  Asn  Pro  Leu  Phe  Trp  Ala  Lys  Lys  Val
225                      230                      235                      240

Ala  Glu  Lys  Val  Gly  Cys  Pro  Val  Gly  Asp  Ala  Ala  Arg  Met  Ala  Gln
                    245                 250                      255

Cys  Leu  Lys  Val  Thr  Asp  Pro  Arg  Ala  Leu  Thr  Leu  Ala  Tyr  Lys  Val
               260                 265                      270

Pro  Leu  Ala  Gly  Leu  Glu  Tyr  Pro  Met  Leu  His  Tyr  Val  Gly  Phe  Val
          275                 280                      285

Pro  Val  Ile  Asp  Gly  Asp  Phe  Ile  Pro  Ala  Asp  Pro  Ile  Asn  Leu  Tyr
     290                 295                 300

Ala  Asn  Ala  Ala  Asp  Ile  Asp  Tyr  Ile  Ala  Gly  Thr  Asn  Asn  Met  Asp
305                 310                      315                           320

Gly  His  Ile  Phe  Ala  Ser  Ile  Asp  Met  Pro  Ala  Ile  Asn  Lys  Gly  Asn
               325                      330                           335

Lys  Lys  Val  Thr  Glu  Glu  Asp  Phe  Tyr  Lys  Leu  Val  Ser  Glu  Phe  Thr
               340                 345                      350

Ile  Thr  Lys  Gly  Leu  Arg  Gly  Ala  Lys  Thr  Thr  Phe  Asp  Val  Tyr  Thr
          355                 360                 365

Glu  Ser  Trp  Ala  Gln  Asp  Pro  Ser  Gln  Glu  Asn  Lys  Lys  Lys  Thr  Val
     370                 375                      380

Val  Asp  Phe  Glu  Thr  Asp  Val  Leu  Phe  Leu  Val  Pro  Thr  Glu  Ile  Ala
385                 390                 395                           400

Leu  Ala  Gln  His  Arg  Ala  Asn  Ala  Lys  Ser  Ala  Lys  Thr  Tyr  Ala  Tyr
               405                 410                      415

Leu  Phe  Ser  His  Pro  Ser  Arg  Met  Pro  Val  Tyr  Pro  Lys  Trp  Val  Gly
               420                 425                 430

Ala  Asp  His  Ala  Asp  Asp  Ile  Gln  Tyr  Val  Phe  Gly  Lys  Pro  Phe  Ala
          435                 440                      445

Thr  Pro  Thr  Gly  Tyr  Arg  Pro  Gln  Asp  Arg  Thr  Val  Ser  Lys  Ala  Met
     450                 455                      460

Ile  Ala  Tyr  Trp  Thr  Asn  Phe  Ala  Lys  Thr  Gly  Asp  Pro  Asn  Met  Gly
465                      470                 475                           480
```

| | | | | | | | | | | | | | | | |
|---|---|---|---|---|---|---|---|---|---|---|---|---|---|---|---|
|Asp|Ser|Ala|Val|Pro<br>485|Thr|His|Trp|Glu|Pro<br>490|Tyr|Thr|Thr|Glu|Asn|Ser<br>495|
|Gly|Tyr|Leu|Glu<br>500|Ile|Thr|Lys|Lys|Met<br>505|Gly|Ser|Ser|Ser|Met<br>510|Lys|Arg|
|Ser|Leu|Arg<br>515|Thr|Asn|Phe|Leu|Arg<br>520|Tyr|Trp|Thr|Leu|Thr<br>525|Tyr|Leu|Ala|
|Leu|Pro<br>530|Thr|Val|Thr|Asp|Gln<br>535|Gly|Ala|Pro|Pro|Val<br>540|Pro|Pro|Thr|Gly|
|Asp<br>545|Ser|Gly|Ala|Pro|Pro<br>550|Val|Pro|Pro|Thr|Gly<br>555|Asp|Ser|Lys|Glu|Ala<br>560|
|Gln|Met|Pro|Ala|Val<br>565|Ile|Arg|Phe| | | | | | | | |

( 2 ) INFORMATION FOR SEQ ID NO:7:

( i ) SEQUENCE CHARACTERISTICS:
        ( A ) LENGTH: 722 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Homo sapiens
        ( F ) TISSUE TYPE: Mammary gland ( i x ) FEATURE:
        ( A ) NAME/KEY: Peptide
        ( B ) LOCATION: 1..722
        ( D ) OTHER INFORMATION: /label= Variant_N ( x i ) SEQUENCE DESCRIPTION: SEQ ID NO:7:

| | | | | | | | | | | | | | | | |
|---|---|---|---|---|---|---|---|---|---|---|---|---|---|---|---|
|Ala<br>1|Lys|Leu|Gly|Ala<br>5|Val|Tyr|Thr|Glu|Gly<br>10|Gly|Phe|Val|Glu|Gly<br>15|Val|
|Asn|Lys|Lys|Leu<br>20|Gly|Leu|Leu|Gly|Asp<br>25|Ser|Val|Asp|Ile|Phe<br>30|Lys|Gly|
|Ile|Pro|Phe<br>35|Ala|Ala|Pro|Thr|Lys<br>40|Ala|Leu|Glu|Asn|Pro<br>45|Gln|Pro|His|
|Pro|Gly<br>50|Trp|Gln|Gly|Thr|Leu<br>55|Lys|Ala|Lys|Asn|Phe<br>60|Lys|Lys|Arg|Cys|
|Leu<br>65|Gln|Ala|Thr|Ile|Thr<br>70|Gln|Asp|Ser|Thr|Tyr<br>75|Gly|Asp|Glu|Asp|Cys<br>80|
|Leu|Tyr|Leu|Asn|Ile<br>85|Trp|Val|Pro|Gln|Gly<br>90|Arg|Lys|Gln|Val|Ser<br>95|Arg|
|Asp|Leu|Pro|Val<br>100|Met|Ile|Trp|Ile|Tyr<br>105|Gly|Gly|Ala|Phe|Leu<br>110|Met|Gly|
|Ser|Gly|His<br>115|Gly|Ala|Asn|Phe|Leu<br>120|Asn|Asn|Tyr|Leu|Tyr<br>125|Asp|Gly|Glu|
|Glu|Ile<br>130|Ala|Thr|Arg|Gly|Asn<br>135|Val|Ile|Val|Val|Thr<br>140|Phe|Asn|Tyr|Arg|
|Val<br>145|Gly|Pro|Leu|Gly|Phe<br>150|Leu|Ser|Thr|Gly|Asp<br>155|Ala|Asn|Leu|Pro|Gly<br>160|
|Asn|Tyr|Gly|Leu|Arg<br>165|Asp|Gln|His|Met|Ala<br>170|Ile|Ala|Trp|Val|Lys<br>175|Arg|
|Asn|Ile|Ala|Ala<br>180|Phe|Gly|Gly|Asp|Pro<br>185|Asn|Gln|Ile|Thr|Leu<br>190|Phe|Gly|
|Glu|Ser|Ala<br>195|Gly|Gly|Ala|Ser|Val<br>200|Ser|Leu|Gln|Thr|Leu<br>205|Ser|Pro|Tyr|

```
Asn Lys Gly Leu Ile Arg Arg Ala Ile Ser Gln Ser Gly Val Ala Leu
    210             215                 220
Ser Pro Trp Val Ile Gln Lys Asn Pro Leu Phe Trp Ala Lys Lys Val
225             230              235                 240
Ala Glu Lys Val Gly Cys Pro Val Gly Asp Ala Ala Arg Met Ala Gln
                245             250                 255
Cys Leu Lys Val Thr Asp Pro Arg Ala Leu Thr Leu Ala Tyr Lys Val
                260             265                 270
Pro Leu Ala Gly Leu Glu Tyr Pro Met Leu His Tyr Val Gly Phe Val
        275             280                 285
Pro Val Ile Asp Gly Asp Phe Ile Pro Ala Asp Pro Ile Asn Leu Tyr
    290             295                 300
Ala Asn Ala Ala Asp Ile Asp Tyr Ile Ala Gly Thr Asn Asn Met Asp
305             310             315                     320
Gly His Ile Phe Ala Ser Ile Asp Met Pro Ala Ile Asn Lys Gly Asn
                325             330             335
Lys Lys Val Thr Glu Glu Asp Phe Tyr Lys Leu Val Ser Glu Phe Thr
            340             345                 350
Ile Thr Lys Gly Leu Arg Gly Ala Lys Thr Thr Phe Asp Val Tyr Thr
            355             360             365
Glu Ser Trp Ala Gln Asp Pro Ser Gln Glu Asn Lys Lys Thr Val
    370             375             380
Val Asp Phe Glu Thr Asp Val Leu Phe Leu Val Pro Thr Glu Ile Ala
385             390             395                     400
Leu Ala Gln His Arg Ala Asn Ala Lys Ser Ala Lys Thr Tyr Ala Tyr
            405             410                 415
Leu Phe Ser His Pro Ser Arg Met Pro Val Tyr Pro Lys Trp Val Gly
            420             425                 430
Ala Asp His Ala Asp Asp Ile Gln Tyr Val Phe Gly Lys Pro Phe Ala
        435             440             445
Thr Pro Thr Gly Tyr Arg Pro Gln Asp Arg Thr Val Ser Lys Ala Met
450             455                 460
Ile Ala Tyr Trp Thr Asn Phe Ala Lys Thr Gly Asp Pro Asn Met Gly
465             470                 475                 480
Asp Ser Ala Val Pro Thr His Trp Glu Pro Tyr Thr Thr Glu Asn Ser
                485             490                 495
Gly Tyr Leu Glu Ile Thr Lys Lys Met Gly Ser Ser Ser Met Lys Arg
            500             505                 510
Ser Leu Arg Thr Asn Phe Leu Arg Tyr Trp Thr Leu Thr Tyr Leu Ala
    515             520                 525
Leu Pro Thr Val Thr Asp Gln Glu Ala Thr Pro Val Pro Pro Thr Gly
530             535                 540
Asp Ser Glu Ala Thr Pro Val Pro Pro Thr Gly Asp Ser Glu Thr Ala
545             550             555                     560
Pro Val Pro Pro Thr Gly Asp Ser Gly Ala Pro Pro Val Pro Pro Thr
                565             570                 575
Gly Asp Ser Gly Ala Pro Pro Val Pro Thr Gly Asp Ser Gly Ala
            580             585                 590
Pro Pro Val Pro Pro Thr Gly Asp Ser Gly Ala Pro Pro Val Pro Pro
            595             600             605
Thr Gly Asp Ser Gly Ala Pro Pro Val Pro Pro Thr Gly Asp Ser Gly
610             615                 620
Ala Pro Pro Val Pro Pro Thr Gly Asp Ser Gly Ala Pro Pro Val Pro
```

|   625 |     |     |     |     | 630 |     |     |     |     | 635 |     |     |     |     | 640 |
|-------|-----|-----|-----|-----|-----|-----|-----|-----|-----|-----|-----|-----|-----|-----|-----|
| Pro   | Thr | Gly | Asp | Ala | Gly | Pro | Pro | Pro | Val | Pro | Pro | Thr | Gly | Asp | Ser |
|       |     |     |     | 645 |     |     |     | 650 |     |     |     |     |     | 655 |     |
| Gly   | Ala | Pro | Pro | Val | Pro | Pro | Thr | Gly | Asp | Ser | Gly | Ala | Pro | Pro | Val |
|       |     |     | 660 |     |     |     | 665 |     |     |     |     |     | 670 |     |     |
| Thr   | Pro | Thr | Gly | Asp | Ser | Glu | Thr | Ala | Pro | Val | Pro | Pro | Thr | Gly | Asp |
|       |     | 675 |     |     |     |     | 680 |     |     |     |     | 685 |     |     |     |
| Ser   | Gly | Ala | Pro | Pro | Val | Pro | Pro | Thr | Gly | Asp | Ser | Glu | Ala | Ala | Pro |
|       | 690 |     |     |     |     | 695 |     |     |     |     | 700 |     |     |     |     |
| Val   | Pro | Pro | Thr | Asp | Asp | Ser | Lys | Glu | Ala | Gln | Met | Pro | Ala | Val | Ile |
| 705   |     |     |     |     | 710 |     |     |     |     | 715 |     |     |     |     | 720 |
| Arg   | Phe |     |     |     |     |     |     |     |     |     |     |     |     |     |     |

( 2 ) INFORMATION FOR SEQ ID NO:8:

( i ) SEQUENCE CHARACTERISTICS:
        ( A ) LENGTH: 2184 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens
        ( F ) TISSUE TYPE: mammary gland ( i x ) FEATURE:
        ( A ) NAME/KEY: CDS
        ( B ) LOCATION: 82..2088
        ( D ) OTHER INFORMATION: /label= Variant_T ( i x ) FEATURE:
        ( A ) NAME/KEY: mat_peptide
        ( B ) LOCATION: 151..2085

( i x ) FEATURE:
        ( A ) NAME/KEY: repeat_region
        ( B ) LOCATION: 1756..2052

( i x ) FEATURE:
        ( A ) NAME/KEY: repeat_unit
        ( B ) LOCATION: 1756..1788

( i x ) FEATURE:
        ( A ) NAME/KEY: repeat_unit
        ( B ) LOCATION: 1789..1821

( i x ) FEATURE:
        ( A ) NAME/KEY: repeat_unit
        ( B ) LOCATION: 1822..1854

( i x ) FEATURE:
        ( A ) NAME/KEY: repeat_unit
        ( B ) LOCATION: 1855..1887

( i x ) FEATURE:
        ( A ) NAME/KEY: repeat_unit
        ( B ) LOCATION: 1888..1920

( i x ) FEATURE:
        ( A ) NAME/KEY: repeat_unit
        ( B ) LOCATION: 1921..1953

( i x ) FEATURE:
        ( A ) NAME/KEY: repeat_unit
        ( B ) LOCATION: 1954..1986

( i x ) FEATURE:

(A) NAME/KEY: repeat_unit
(B) LOCATION: 1987..2019

(ix) FEATURE:
(A) NAME/KEY: repeat_unit
(B) LOCATION: 2020..2052

(xi) SEQUENCE DESCRIPTION: SEQ ID NO:8:

```
ACCTTCTGTA TCAGTTAAGT GTCAAGATGG AAGGAACAGC AGTCTCAAGA TAATGCAAAG        60

AGTTTATTCA TCCAGAGGCT G ATG CTC ACC ATG GGG CGC CTG CAA CTG GTT        111
                        Met Leu Thr Met Gly Arg Leu Gln Leu Val
                        -23         -20                     -15

GTG TTG GGC CTC ACC TGC TGC TGG GCA GTG GCG AGT GCC GCG AAG CTG        159
Val Leu Gly Leu Thr Cys Cys Trp Ala Val Ala Ser Ala Ala Lys Leu
            -10                 -5                       1

GGC GCC GTG TAC ACA GAA GGT GGG TTC GTG GAA GGC GTC AAT AAG AAG        207
Gly Ala Val Tyr Thr Glu Gly Gly Phe Val Glu Gly Val Asn Lys Lys
        5                   10                  15

CTC GGC CTC CTG GGT GAC TCT GTG GAC ATC TTC AAG GGC ATC CCC TTC        255
Leu Gly Leu Leu Gly Asp Ser Val Asp Ile Phe Lys Gly Ile Pro Phe
20                  25                  30                  35

GCA GCT CCC ACC AAG GCC CTG GAA AAT CCT CAG CCA CAT CCT GGC TGG        303
Ala Ala Pro Thr Lys Ala Leu Glu Asn Pro Gln Pro His Pro Gly Trp
                40                  45                  50

CAA GGG ACC CTG AAG GCC AAG AAC TTC AAG AAG AGA TGC CTG CAG GCC        351
Gln Gly Thr Leu Lys Ala Lys Asn Phe Lys Lys Arg Cys Leu Gln Ala
            55                  60                  65

ACC ATC ACC CAG GAC AGC ACC TAC GGG GAT GAA GAC TGC CTG TAC CTC        399
Thr Ile Thr Gln Asp Ser Thr Tyr Gly Asp Glu Asp Cys Leu Tyr Leu
        70                  75                  80

AAC ATT TGG GTG CCC CAG GGC AGG AAG CAA GTC TCC CGG GAC CTG CCC        447
Asn Ile Trp Val Pro Gln Gly Arg Lys Gln Val Ser Arg Asp Leu Pro
85                  90                  95

GTT ATG ATC TGG ATC TAT GGA GGC GCC TTC CTC ATG GGG TCC GGC CAT        495
Val Met Ile Trp Ile Tyr Gly Gly Ala Phe Leu Met Gly Ser Gly His
100                 105                 110                 115

GGG GCC AAC TTC CTC AAC AAC TAC CTG TAT GAC GGC GAG GAG ATC GCC        543
Gly Ala Asn Phe Leu Asn Asn Tyr Leu Tyr Asp Gly Glu Glu Ile Ala
                120                 125                 130

ACA CGC GGA AAC GTC ATC GTG GTC ACC TTC AAC TAC CGT GTC GGC CCC        591
Thr Arg Gly Asn Val Ile Val Val Thr Phe Asn Tyr Arg Val Gly Pro
            135                 140                 145

CTT GGG TTC CTC AGC ACT GGG GAC GCC AAT CTG CCA GGT AAC TAT GGC        639
Leu Gly Phe Leu Ser Thr Gly Asp Ala Asn Leu Pro Gly Asn Tyr Gly
        150                 155                 160

CTT CGG GAT CAG CAC ATG GCC ATT GCT TGG GTG AAG AGG AAT ATC GCG        687
Leu Arg Asp Gln His Met Ala Ile Ala Trp Val Lys Arg Asn Ile Ala
165                 170                 175

GCC TTC GGG GGG GAC CCC AAC AAC ATC ACG CTC TTC GGG GAG TCT GCT        735
Ala Phe Gly Gly Asp Pro Asn Asn Ile Thr Leu Phe Gly Glu Ser Ala
180                 185                 190                 195

GGA GGT GCC AGC GTC TCT CTG CAG ACC CTC TCC CCC TAC AAC AAG GGC        783
Gly Gly Ala Ser Val Ser Leu Gln Thr Leu Ser Pro Tyr Asn Lys Gly
                200                 205                 210

CTC ATC CGG CGA GCC ATC AGC CAG AGC GGC GTG GCC CTG AGT CCC TGG        831
Leu Ile Arg Arg Ala Ile Ser Gln Ser Gly Val Ala Leu Ser Pro Trp
            215                 220                 225

GTC ATC CAG AAA AAC CCA CTC TTC TGG GCC AAA AAG GTG GCT GAG AAG        879
Val Ile Gln Lys Asn Pro Leu Phe Trp Ala Lys Lys Val Ala Glu Lys
        230                 235                 240

GTG GGT TGC CCT GTG GGT GAT GCC GCC AGG ATG GCC CAG TGT CTG AAG        927
```

-continued

| | | | | | | | | | | | | | | | |
|---|---|---|---|---|---|---|---|---|---|---|---|---|---|---|---|
| Val | Gly | Cys | Pro | Val | Gly | Asp | Ala | Ala | Arg | Met | Ala | Gln | Cys | Leu | Lys |
| 245 | | | | | 250 | | | | | 255 | | | | | |

| GTT | ACT | GAT | CCC | CGA | GCC | CTG | ACG | CTG | GCC | TAT | AAG | GTG | CCG | CTG | GCA | 975 |
|---|---|---|---|---|---|---|---|---|---|---|---|---|---|---|---|---|
| Val | Thr | Asp | Pro | Arg | Ala | Leu | Thr | Leu | Ala | Tyr | Lys | Val | Pro | Leu | Ala | |
| 260 | | | | | 265 | | | | | 270 | | | | | 275 | |

| GGC | CTG | GAG | TAC | CCC | ATG | CTG | CAC | TAT | GTG | GGC | TTC | GTC | CCT | GTC | ATT | 1023 |
|---|---|---|---|---|---|---|---|---|---|---|---|---|---|---|---|---|
| Gly | Leu | Glu | Tyr | Pro | Met | Leu | His | Tyr | Val | Gly | Phe | Val | Pro | Val | Ile | |
| | | | | 280 | | | | | 285 | | | | | 290 | | |

| GAT | GGA | GAC | TTC | ATC | CCC | GCT | GAC | CCG | ATC | AAC | CTG | TAC | GCC | AAC | GCC | 1071 |
|---|---|---|---|---|---|---|---|---|---|---|---|---|---|---|---|---|
| Asp | Gly | Asp | Phe | Ile | Pro | Ala | Asp | Pro | Ile | Asn | Leu | Tyr | Ala | Asn | Ala | |
| | | | 295 | | | | | 300 | | | | | 305 | | | |

| GCC | GAC | ATC | GAC | TAT | ATA | GCA | GGC | ACC | AAC | AAC | ATG | GAC | GGC | CAC | ATC | 1119 |
|---|---|---|---|---|---|---|---|---|---|---|---|---|---|---|---|---|
| Ala | Asp | Ile | Asp | Tyr | Ile | Ala | Gly | Thr | Asn | Asn | Met | Asp | Gly | His | Ile | |
| | | 310 | | | | | 315 | | | | | 320 | | | | |

| TTC | GCC | AGC | ATC | GAC | ATG | CCT | GCC | ATC | AAC | AAG | GGC | AAC | AAG | AAA | GTC | 1167 |
|---|---|---|---|---|---|---|---|---|---|---|---|---|---|---|---|---|
| Phe | Ala | Ser | Ile | Asp | Met | Pro | Ala | Ile | Asn | Lys | Gly | Asn | Lys | Lys | Val | |
| 325 | | | | | 330 | | | | | 335 | | | | | | |

| ACG | GAG | GAG | GAC | TTC | TAC | AAG | CTG | GTC | AGT | GAG | TTC | ACA | ATC | ACC | AAG | 1215 |
|---|---|---|---|---|---|---|---|---|---|---|---|---|---|---|---|---|
| Thr | Glu | Glu | Asp | Phe | Tyr | Lys | Leu | Val | Ser | Glu | Phe | Thr | Ile | Thr | Lys | |
| 340 | | | | | 345 | | | | | 350 | | | | | 355 | |

| GGG | CTC | AGA | GGC | GCC | AAG | ACG | ACC | TTT | GAT | GTC | TAC | ACC | GAG | TCC | TGG | 1263 |
|---|---|---|---|---|---|---|---|---|---|---|---|---|---|---|---|---|
| Gly | Leu | Arg | Gly | Ala | Lys | Thr | Thr | Phe | Asp | Val | Tyr | Thr | Glu | Ser | Trp | |
| | | | | 360 | | | | | 365 | | | | | 370 | | |

| GCC | CAG | GAC | CCA | TCC | CAG | GAG | AAT | AAG | AAG | AAG | ACT | GTG | GTG | GAC | TTT | 1311 |
|---|---|---|---|---|---|---|---|---|---|---|---|---|---|---|---|---|
| Ala | Gln | Asp | Pro | Ser | Gln | Glu | Asn | Lys | Lys | Lys | Thr | Val | Val | Asp | Phe | |
| | | | 375 | | | | | 380 | | | | | 385 | | | |

| GAG | ACC | GAT | GTC | CTC | TTC | CTG | GTG | CCC | ACC | GAG | ATT | GCC | CTA | GCC | CAG | 1359 |
|---|---|---|---|---|---|---|---|---|---|---|---|---|---|---|---|---|
| Glu | Thr | Asp | Val | Leu | Phe | Leu | Val | Pro | Thr | Glu | Ile | Ala | Leu | Ala | Gln | |
| | | 390 | | | | | 395 | | | | | 400 | | | | |

| CAC | AGA | GCC | AAT | GCC | AAG | AGT | GCC | AAG | ACC | TAC | GCC | TAC | CTG | TTT | TCC | 1407 |
|---|---|---|---|---|---|---|---|---|---|---|---|---|---|---|---|---|
| His | Arg | Ala | Asn | Ala | Lys | Ser | Ala | Lys | Thr | Tyr | Ala | Tyr | Leu | Phe | Ser | |
| 405 | | | | | 410 | | | | | 415 | | | | | | |

| CAT | CCC | TCT | CGG | ATG | CCC | GTC | TAC | CCC | AAA | TGG | GTG | GGG | GCC | GAC | CAT | 1455 |
|---|---|---|---|---|---|---|---|---|---|---|---|---|---|---|---|---|
| His | Pro | Ser | Arg | Met | Pro | Val | Tyr | Pro | Lys | Trp | Val | Gly | Ala | Asp | His | |
| 420 | | | | | 425 | | | | | 430 | | | | | 435 | |

| GCA | GAT | GAC | ATT | CAG | TAC | GTT | TTC | GGG | AAG | CCC | TTC | GCC | ACC | CCC | ACG | 1503 |
|---|---|---|---|---|---|---|---|---|---|---|---|---|---|---|---|---|
| Ala | Asp | Asp | Ile | Gln | Tyr | Val | Phe | Gly | Lys | Pro | Phe | Ala | Thr | Pro | Thr | |
| | | | 440 | | | | | 445 | | | | | 450 | | | |

| GGC | TAC | CGG | CCC | CAA | GAC | AGG | ACA | GTC | TCT | AAG | GCC | ATG | ATC | GCC | TAC | 1551 |
|---|---|---|---|---|---|---|---|---|---|---|---|---|---|---|---|---|
| Gly | Tyr | Arg | Pro | Gln | Asp | Arg | Thr | Val | Ser | Lys | Ala | Met | Ile | Ala | Tyr | |
| | | | 455 | | | | | 460 | | | | | 465 | | | |

| TGG | ACC | AAC | TTT | GCC | AAA | ACA | GGG | GAC | CCC | AAC | ATG | GGC | GAC | TCG | GCT | 1599 |
|---|---|---|---|---|---|---|---|---|---|---|---|---|---|---|---|---|
| Trp | Thr | Asn | Phe | Ala | Lys | Thr | Gly | Asp | Pro | Asn | Met | Gly | Asp | Ser | Ala | |
| | | 470 | | | | | 475 | | | | | 480 | | | | |

| GTG | CCC | ACA | CAC | TGG | GAA | CCC | TAC | ACT | ACG | GAA | AAC | AGC | GGC | TAC | CTG | 1647 |
|---|---|---|---|---|---|---|---|---|---|---|---|---|---|---|---|---|
| Val | Pro | Thr | His | Trp | Glu | Pro | Tyr | Thr | Thr | Glu | Asn | Ser | Gly | Tyr | Leu | |
| 485 | | | | | 490 | | | | | 495 | | | | | | |

| GAG | ATC | ACC | AAG | AAG | ATG | GGC | AGC | AGC | TCC | ATG | AAG | CGG | AGC | CTG | AGA | 1695 |
|---|---|---|---|---|---|---|---|---|---|---|---|---|---|---|---|---|
| Glu | Ile | Thr | Lys | Lys | Met | Gly | Ser | Ser | Ser | Met | Lys | Arg | Ser | Leu | Arg | |
| 500 | | | | | 505 | | | | | 510 | | | | | 515 | |

| ACC | AAC | TTC | CTG | CGC | TAC | TGG | ACC | CTC | ACC | TAT | CTG | GCG | CTG | CCC | ACA | 1743 |
|---|---|---|---|---|---|---|---|---|---|---|---|---|---|---|---|---|
| Thr | Asn | Phe | Leu | Arg | Tyr | Trp | Thr | Leu | Thr | Tyr | Leu | Ala | Leu | Pro | Thr | |
| | | | | 520 | | | | | 525 | | | | | 530 | | |

| GTG | ACC | GAC | CAG | GAG | GCC | ACC | CCT | GTG | CCC | CCC | ACA | GGG | GAC | TCC | GAG | 1791 |
|---|---|---|---|---|---|---|---|---|---|---|---|---|---|---|---|---|
| Val | Thr | Asp | Gln | Glu | Ala | Thr | Pro | Val | Pro | Pro | Thr | Gly | Asp | Ser | Glu | |
| | | | 535 | | | | | 540 | | | | | 545 | | | |

| GCC | ACT | CCC | GTG | CCC | CCC | ACG | GGT | GAC | TCC | GAG | ACC | GCC | CCC | GTG | CCG | 1839 |
|---|---|---|---|---|---|---|---|---|---|---|---|---|---|---|---|---|
| Ala | Thr | Pro | Val | Pro | Pro | Thr | Gly | Asp | Ser | Glu | Thr | Ala | Pro | Val | Pro | |
| | | 550 | | | | | 555 | | | | | 560 | | | | |

| CCC | ACG | GGT | GAC | TCC | GGG | GCC | CCC | CCC | GTG | CCG | CCC | ACG | GGT | GAC | TCC | 1887 |

```
Pro Thr Gly Asp Ser Gly Ala Pro Pro Val Pro Pro Thr Gly Asp Ser
    565                 570                 575

GGG GCC CCC CCC GTG CCG CCC ACG GGT GAC TCC GGG GCC CCC CCC GTG      1935
Gly Ala Pro Pro Val Pro Pro Thr Gly Asp Ser Gly Ala Pro Pro Val
580                 585                 590                 595

CCG CCC ACG GGT GAC TCC GGG GCC CCC CCC GTG CCG CCC ACG GGT GAC      1983
Pro Pro Thr Gly Asp Ser Gly Ala Pro Pro Val Pro Pro Thr Gly Asp
            600                 605                 610

TCC GGG GCC CCC CCC GTG CCG CCC ACG GGT GAC TCC GGG GCC CCC CCT      2031
Ser Gly Ala Pro Pro Val Pro Pro Thr Gly Asp Ser Gly Ala Pro Pro
        615                 620                 625

GTG CCC CCC ACA GAT GAC TCC AAG GAA GCT CAG ATG CCT GCA GTC ATT      2079
Val Pro Pro Thr Asp Asp Ser Lys Glu Ala Gln Met Pro Ala Val Ile
            630                 635                 640

AGG TTT TAGCGTCCCA TGAGCCTTGG TATCAAGAGG CCACAAGAGT GGGACCCCAG       2135
Arg Phe
    645

GGGCTCCCCT CCCATCTTGA GCTCTTCCTG AATAAAGCCT CATACCCCT                2184
```

(2) INFORMATION FOR SEQ ID NO:9:

(i) SEQUENCE CHARACTERISTICS:
      (A) LENGTH: 668 amino acids
      (B) TYPE: amino acid
      (D) TOPOLOGY: linear (ii) MOLECULE TYPE: protein (xi) SEQUENCE DESCRIPTION: SEQ ID NO:9:

```
Met Leu Thr Met Gly Arg Leu Gln Leu Val Val Leu Gly Leu Thr Cys
-23         -20                 -15                 -10

Cys Trp Ala Val Ala Ser Ala Ala Lys Leu Gly Ala Val Tyr Thr Glu
         -5                   1                   5

Gly Gly Phe Val Glu Gly Val Asn Lys Lys Leu Gly Leu Leu Gly Asp
 10              15                  20                  25

Ser Val Asp Ile Phe Lys Gly Ile Pro Phe Ala Ala Pro Thr Lys Ala
            30                  35                  40

Leu Glu Asn Pro Gln Pro His Pro Gly Trp Gln Gly Thr Leu Lys Ala
            45                  50                  55

Lys Asn Phe Lys Lys Arg Cys Leu Gln Ala Thr Ile Thr Gln Asp Ser
        60                  65                  70

Thr Tyr Gly Asp Glu Asp Cys Leu Tyr Leu Asn Ile Trp Val Pro Gln
    75                  80                  85

Gly Arg Lys Gln Val Ser Arg Asp Leu Pro Val Met Ile Trp Ile Tyr
 90              95                 100                 105

Gly Gly Ala Phe Leu Met Gly Ser Gly His Gly Ala Asn Phe Leu Asn
            110                 115                 120

Asn Tyr Leu Tyr Asp Gly Glu Glu Ile Ala Thr Arg Gly Asn Val Ile
            125                 130                 135

Val Val Thr Phe Asn Tyr Arg Val Gly Pro Leu Gly Phe Leu Ser Thr
        140                 145                 150

Gly Asp Ala Asn Leu Pro Gly Asn Tyr Gly Leu Arg Asp Gln His Met
    155                 160                 165

Ala Ile Ala Trp Val Lys Arg Asn Ile Ala Ala Phe Gly Gly Asp Pro
170                 175                 180                 185

Asn Asn Ile Thr Leu Phe Gly Glu Ser Ala Gly Gly Ala Ser Val Ser
            190                 195                 200

Leu Gln Thr Leu Ser Pro Tyr Asn Lys Gly Leu Ile Arg Arg Ala Ile
```

```
                         205                       210                       215
Ser  Gln  Ser  Gly  Val  Ala  Leu  Ser  Pro  Trp  Val  Ile  Gln  Lys  Asn  Pro
              220                       225                       230
Leu  Phe  Trp  Ala  Lys  Lys  Val  Ala  Glu  Lys  Val  Gly  Cys  Pro  Val  Gly
         235                       240                       245
Asp  Ala  Ala  Arg  Met  Ala  Gln  Cys  Leu  Lys  Val  Thr  Asp  Pro  Arg  Ala
250                       255                       260                       265
Leu  Thr  Leu  Ala  Tyr  Lys  Val  Pro  Leu  Ala  Gly  Leu  Glu  Tyr  Pro  Met
                   270                       275                       280
Leu  His  Tyr  Val  Gly  Phe  Val  Pro  Val  Ile  Asp  Gly  Asp  Phe  Ile  Pro
              285                       290                       295
Ala  Asp  Pro  Ile  Asn  Leu  Tyr  Ala  Asn  Ala  Ala  Asp  Ile  Asp  Tyr  Ile
         300                       305                       310
Ala  Gly  Thr  Asn  Asn  Met  Asp  Gly  His  Ile  Phe  Ala  Ser  Ile  Asp  Met
         315                       320                       325
Pro  Ala  Ile  Asn  Lys  Gly  Asn  Lys  Lys  Val  Thr  Glu  Glu  Asp  Phe  Tyr
330                       335                       340                       345
Lys  Leu  Val  Ser  Glu  Phe  Thr  Ile  Thr  Lys  Gly  Leu  Arg  Gly  Ala  Lys
                   350                       355                       360
Thr  Thr  Phe  Asp  Val  Tyr  Thr  Glu  Ser  Trp  Ala  Gln  Asp  Pro  Ser  Gln
              365                       370                       375
Glu  Asn  Lys  Lys  Thr  Val  Val  Asp  Phe  Glu  Thr  Asp  Val  Leu  Phe
         380                       385                       390
Leu  Val  Pro  Thr  Glu  Ile  Ala  Leu  Ala  Gln  His  Arg  Ala  Asn  Ala  Lys
         395                       400                       405
Ser  Ala  Lys  Thr  Tyr  Ala  Tyr  Leu  Phe  Ser  His  Pro  Ser  Arg  Met  Pro
410                       415                       420                       425
Val  Tyr  Pro  Lys  Trp  Val  Gly  Ala  Asp  His  Ala  Asp  Asp  Ile  Gln  Tyr
                   430                       435                       440
Val  Phe  Gly  Lys  Pro  Phe  Ala  Thr  Pro  Thr  Gly  Tyr  Arg  Pro  Gln  Asp
                   445                       450                       455
Arg  Thr  Val  Ser  Lys  Ala  Met  Ile  Ala  Tyr  Trp  Thr  Asn  Phe  Ala  Lys
         460                       465                       470
Thr  Gly  Asp  Pro  Asn  Met  Gly  Asp  Ser  Ala  Val  Pro  Thr  His  Trp  Glu
    475                       480                       485
Pro  Tyr  Thr  Thr  Glu  Asn  Ser  Gly  Tyr  Leu  Glu  Ile  Thr  Lys  Lys  Met
490                       495                       500                       505
Gly  Ser  Ser  Ser  Met  Lys  Arg  Ser  Leu  Arg  Thr  Asn  Phe  Leu  Arg  Tyr
                   510                       515                       520
Trp  Thr  Leu  Thr  Tyr  Leu  Ala  Leu  Pro  Thr  Val  Thr  Asp  Gln  Glu  Ala
              525                       530                       535
Thr  Pro  Val  Pro  Pro  Thr  Gly  Asp  Ser  Glu  Ala  Thr  Pro  Val  Pro  Pro
         540                       545                       550
Thr  Gly  Asp  Ser  Glu  Thr  Ala  Pro  Val  Pro  Pro  Thr  Gly  Asp  Ser  Gly
         555                       560                       565
Ala  Pro  Pro  Val  Pro  Pro  Thr  Gly  Asp  Ser  Gly  Ala  Pro  Pro  Val  Pro
570                       575                       580                       585
Pro  Thr  Gly  Asp  Ser  Gly  Ala  Pro  Pro  Val  Pro  Pro  Thr  Gly  Asp  Ser
              590                       595                       600
Gly  Ala  Pro  Pro  Val  Pro  Pro  Thr  Gly  Asp  Ser  Gly  Ala  Pro  Pro  Val
         605                       610                       615
Pro  Pro  Thr  Gly  Asp  Ser  Gly  Ala  Pro  Pro  Val  Pro  Pro  Thr  Asp  Asp
         620                       625                       630
```

Ser Lys Glu Ala Gln Met Pro Ala Val Ile Arg Phe
635                 640                 645

( 2 ) INFORMATION FOR SEQ ID NO:10:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

CGGGATCCGA AGCCCTTCGC CACCCCACG        30

( 2 ) INFORMATION FOR SEQ ID NO:11:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

CGAAGCTTGT CGACTTACTA CTGATCAGTC ACTGTGGGCA GCGCCAG        47

( 2 ) INFORMATION FOR SEQ ID NO:12:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

GGGAATTCTG GCCATTGCTT GGGTGAAGAG GAATATCGCG GCCTTCGGGG GGGACCCCAA        60

CCAGATCACG CTCTTCGGGG AGTCT        85

( 2 ) INFORMATION FOR SEQ ID NO:13:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

CGGGATCCCA CATAGTGCAG CATGGGGTAC TCCAGGCC        38

( 2 ) INFORMATION FOR SEQ ID NO:14:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

GATCAGGGGG CCCCCCCCGT GCCGCCACG GGTGACTCCG GG        42

( 2 ) INFORMATION FOR SEQ ID NO:15:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

GCCCCCCCG TGCCGCCCAC GGGTGACTCC AAGGAAGCTC AGA    43

( 2 ) INFORMATION FOR SEQ ID NO:16:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

TGCCTGCAGT CATTAGGTTT TAGTAAGTCG ACA    33

( 2 ) INFORMATION FOR SEQ ID NO:17:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

AGCTTGTCGA CTTACTAAAA CCTAATGACT G    31

( 2 ) INFORMATION FOR SEQ ID NO:18:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

CAGGCATCTG AGCTTCCTTG GAGTCACCCG TGGGCGGCAC GGGGGGGGCC CCGGA    55

( 2 ) INFORMATION FOR SEQ ID NO:19:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

GTCACCCGTG GGCGGCACGG GGGGGCCCC CT    32

( 2 ) INFORMATION FOR SEQ ID NO:20:

( i ) SEQUENCE CHARACTERISTICS:
        ( A ) LENGTH: 19 base pairs

-continued

```
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:20:

GATCAGAAGG AAGCTCAGA                                                              19

( 2 ) INFORMATION FOR SEQ ID NO:21:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

CAGGCATCTG AGCTTCCTTC T                                                           21
```

TRANSGENIC NON-HUMAN MAMMALS PRODUCING BSSL VARIANTS

This application is a divisional of application Ser. No. 08/204,691, filed on Mar. 1, 1994.

TECHNICAL FIELD

The present invention relates to novel polypeptides which are variants of Bile Salt-Stimulated Lipase (BSSL; EC 3.1.1.1). It also relates to DNA molecules encoding the said polypeptides, and to subproducts comprising the said DNA molecules. The invention further relates to processes for producing the said BSSL variants and for producing transgenic non-human mammals capable of expressing the BSSL variants. Furthermore the invention relates to such transgenic animals as well as to infant formulas comprising milk from such transgenic animals. The invention also relates to pharmaceutical compositions comprising the said polypeptides; and the use of the said polypeptides and DNA molecules for the manufacture of medicaments.

BACKGROUND ART

Hydrolysis of Dietary Lipids

Dietary lipids are an important source of energy. The energy-rich triacylglycerols constitute more than 95% of these lipids. Some of the lipids, e.g. certain fatty acids and the fat-soluble vitamins, are essential dietary constituents. Before gastrointestinal absorption the triacylglycerols as well as the minor components, i.e. esterified fat-soluble vitamins and cholesterol, and diacylphosphatidylglycerols, require hydrolysis of the ester bonds to give rise to less hydrophobic, absorbable products. These reactions are catalyzed by a specific group of enzymes called lipases.

In the human, the essential lipases involved are considered to be Gastric Lipase, Pancreatic Colipase-Dependent Lipase (hydrolysis of tri- and diacylglycerols), Pancreatic Phospholipase A2 (hydrolysis of diacylphosphatidylglycerols) and Carboxylic Ester Hydrolase (CEH) (hydrolysis of cholesteryl- and fat soluble vitamin esters, but also tri-, di-, and monoacylglycerols). In the breast-fed newborn, Bile Salt-Stimulated Lipase (BSSL) plays an essential part in the hydrolysis of several of the above mentioned lipids. Together with bile salts the products of lipid digestion form mixed micelles or unilamellar vesicles (Hernell et al., 1990) from which absorption occurs.

Bile Salt-Stimulated Lipase

Bile Salt-Stimulated Lipase (BSSL) is a constituent of milk in a limited number of species, e.g. humans, gorillas, cats and dogs (Hernell et al., 1989, Hamosh et al., 1986). When mixed with bile in upper small intestinal contents, BSSL is specifically activated by primary bile salts (Hernell, 1975). BSSL, which accounts for approximately 1% of total milk protein (Bläckberg & Hernell, 1981), is not degraded during passage with the milk through the stomach, and in duodenal contents it is protected by bile salts from inactivation by pancreatic proteases such as trypsin and chymotrypsin.

Heat treatment of human milk (pasteurization at 62.5° C., 30 min), which inactivates BSSL completely (Björksten et al., 1980), reduces the coefficient of fat absorption by approximately ⅓ in preterm infants (Williamson et al., 1978, Atkinson et al., 1981). Hence, the superior utilization of fresh human milk triacylglycerol compared to that of infant formulas of similar fat composition is due to BSSL (Hernell et al., 1991, Chapell et al., 1986).

BSSL is a non-specific lipase (EC 3.1.1.1) in as much as it hydrolyses not only triacylglycerol but also di- and monoacylglycerol, cholesteryl esters and fat-soluble vitamin esters (Bläckberg & Hernell, 1983). Thus, after activation, BSSL has the potential to hydrolyze most human milk lipids by itself, albeit the most efficient utilization of human milk triacylglycerol requires the synergistic action of gastric lipase (EC 3.1.1.3), colipase-dependent pancreatic lipase (EC 3.1.1.3), and BSSL (Bernbäck et al, 1990)

Recent studies suggest that the milk enzyme is of particular importance for the utilization of long-chain polyunsaturated fatty acids by the newborn infant (Hernell et al. 1993). These fatty acids are important precursors of eicosanoids and for the neuro-development. Newborn infants, particularly if born before term, have a limited capacity for synthesis of these fatty acids from their precursors. Hence, they are considered essential for an as yet not defined period of time after birth.

In recent studies from several laboratories the cDNA structures from both the milk lipase and the pancreas Carboxylic Ester Hydrolase (CEH) (E.C. 3.1.1.1) have been characterized (Baba et al., 1991; Hui et al., 1991; Nilsson et al., 1990; Reue et al., 1991) and the conclusion is that the milk enzyme and the pancreas enzyme are products of the same gene. The cDNA sequence and deduced amino acid sequence of the BSSL/CEH gene (SEQ ID NO:1) are disclosed also in WO 91/15234 (Oklahoma Medical Research Foundation) and in WO 91/18923 (Aktiebolaget Astra).

BSSL is a single-chain glycoprotein. The deduced protein (SEQ ID NO:3) contains 722 amino acid residues and is highly glycosylated (Abouakil et al., 1989). The N-termninal half of the protein shows a striking homology to acetyl cholinesterase and some other esterases (Nilsson et al., 1990).

A tentative active site serine residue is located at serine-194; the sequence around this serine accords with the consensus active-site sequence of serine hydrolases. The single tentative N-glycosylation site is positioned only seven residues N-terminal of the active site serine (Nilsson et al., 1990).

The BSSL sequence contains in its C-terminal part 16 proline-rich repeats of 11 anmino acid residues each. A variation in number of repeats seems to be a major explanation for differences in molecular size and amino acid composition between corresponding enzymes from different species (Han et al., 1987, Fontaine et al., 1991, Kyger et al., 1989). These repeats carry most of the 15-20% carbohydrate of the protein (Baba et al., 1991, Abouakil et al., 1989).

The unique structural difference between BSSL and typical esterases resides in the C-terminal part of the polypeptide chain, i.e. the 16 proline-rich repeats of 11 amino acid residues. The corresponding pancreatic enzymes from cow and rat have only 3 and 4 repeats, respectively (Han et al., 1987, Kyger et al., 1989). A likely hypothesis has therefore been that the C-terminal part, or at least part of it, is indispensable for lipase activity, i.e. activity against emulsified long-chain triacylglycerol.

Lipid Malabsorption

Common causes of lipid malabsorption, and hence malnutrition, are reduced intraluminal levels of Pancreatic Colipase-Dependent Lipase and/or bile salts. Typical examples of such lipase deficiency are patients suffering from cystic fibrosis, a common genetic disorder resulting in a life-long deficiency in 80% of the patients, and chronic pancreatitis, often due to chronic alcoholism.

The present treatment of patients suffering from a deficiency of pancreatic lipase is the oral administration of very large doses of a crude preparation of porcine pancreatic enzymes. However, Colipase-Dependent Pancreatic Lipase is inactivated by the low pH prevalent in the stomach. This effect cannot be completely overcome by the use of large doses of enzyme. Thus the large doses administered are inadequate for most patients, and moreover the preparations are impure and unpalatable.

Certain tablets have been formulated which pass through the acid regions of the stomach and discharge the enzyme only in the relatively alkaline environment of the jejunum. However, many patients suffering from pancreatic disorders have an abnormally acid jejunum and in those cases the tablets may fail to discharge the enzyme.

Moreover, since the preparations presently on the market are of a non-human source there is a risk of immunoreactions that may cause harmful effects to the patients or result in reduced therapy efficiency. A further drawback with the present preparations is that their content of other lipolytic activities than Colipase-Dependent Lipase are not stated. In fact, most of them contain very low levels of BSSL/CEH activity. This may be one reason why many patients, suffering from cystic fibrosis in spite of supplementation therapy, suffer from deficiencies of fat soluble vitamins and essential fatty acids.

Thus, there is a great need for products with properties and structure derived from human lipases and with a broad substrate specificity, which products may be orally administered to patients suffering from deficiency of one or several of the pancreatic lipolytic enzymes. Products that can be derived from the use of the present invention fulfil this need by themselves, or in combination with preparations containing other lipases.

SHORT DESCRIPTION OF THE INVENTIVE CONCEPT

Recombinant BSSL variants according to the invention, have maintained catalytic activity, but contain less glycosylation sites than full-length BSSL, and are thus produced with a potentially reduced degree of carbohydrate heterogeneity. This reduced complexity facilitates purification and characterization of the recombinant protein, which will result in a more cost-effective production of polypeptides having BSSL activity.

In another aspect, the reduced degree of glycosylation is less demanding for the host and allows higher production in several host cells. In yet another aspect, the reduced number of glycosylation sites in a BSSL variant allows efficient production in lower eukaryotes and restricts the potential risk of abberrant glycosylation, which may raise immunological reactions. The reduced size and less complex glycosylation also implies that the host range is broader than for a protein having very complex and heavy carbohydrate moieties.

Therapeutic use of a BSSL variant which is smaller in size but is equally active, means that the weight of the substance needed for supplementation is reduced. A further possible advantage with a recombinant BSSL variant lacking most or all of the O-glycosylated repeats is a reduced risk for an immunological response in the recipient individual. This is due to the fact that the O-linked sugar may be very heterogenous depending on the cell in which it is produced.

There are indications in the scientific literature that native BSSL binds to, and is taken up by, the intestinal mucosa. A BSSL variant which is selected for having a reduced uptake, will be active on the dietary lipid substrates for a longer period of time, leading to a more efficient intraluminal digestion. Examples of such variants are molecules with reduced glycosylation.

As mentioned above, BSSL has been suggested to be of particular importance for the utilization of long-chain polyunsaturated fatty acids (Hernell et al., 1993), which are of great importance for neuro-development of the newborn infant, and of vitamin A. A BSSL variant according to the invention, which is more effective in these respects, can be selected by known methods. A truncated, or shortened, enzyme is likely to be different with regard to conformation which may affect the specificity against different lipid substrates.

DISCLOSURE OF THE INVENTION

In one aspect, the invention relates to a nucleic acid molecule encoding a polypeptide which is a BSSL variant shorter than 722 amino acids, said BSSL variant comprising part of the amino acid sequence shown as residues 536–722 in SEQ ID NO: 3.

The term "part of the amino acid sequence" is to be understood as comprising one single amino acid as well as a sequence of several amino acids or several such sequences combined.

The term "BSSL variant" is to be understood as a polypeptide having BSSL activity and comprising a part of the amino acid sequence of human BSSL shown as SEQ ID NO: 3 in the Sequence Listing.

The term "polypeptide having BSSL activity" is to be understood as a polypeptide comprising at least the properties (a) suitable for oral administration;
(b) activated by specific bile salts;
(c) acting as a non-specific lipase in the contents of the small intestines, i.e. being able to hydrolyze lipids relatively independent of their chemical structure and physical state (emulsified, micellar, soluble);

and optionally one or more of the properties (d) ability to hydrolyze triacylglycerols with fatty acids of different chain-length and different degree of unsaturation;
(e) ability to hydrolyze also diacylglycerol, monoacylglycerol, cholesteryl esters, lysophospatidylacylglycerol, and retinyl and other fat soluble vitamin-esters;
(f) ability to hydrolyze not only the sn-1(3) ester bonds in a triacylglycerol but also the sn-2 ester bond;
(g) ability to interact with not only primary but also secondary bile salts;
(h) dependent on bile salts for optimal activity;
(i) stable in the sence that gastric contents will not affect the catalytical efficiency to any substantial degree;
(j) stable against inactivation by pancreatic proteases, e.g. trypsin, provided bile salts are present;
(k) ability to bind to heparin and heparin derivatives, e.g. heparan sulphate;
(l) ability to bind to lipid-water interphases;
(m) stable enough to permit lyophilization;
(n) stable when mixed with food constituents such as in human milk, or milk formula.

In further aspects, the invention relates to a nucleic acid molecule according to above, wherein the said BSSL variant has a phenylalanine residue in its C-terminal position, or comprises the sequence Gln-Met-Pro in its C-terminal part, alternatively comprises the amino acid sequence shown as residues 712-722 in SEQ ID NO: 3 in its C-terminal part.

In the present context, the term "C-terminal position" designates the position of the final C-terminal residue, while the term "C-terminal part" is to be understood as the approximately 50 amino acid residues which constitute the C-terminal end of the BSSL variant.

The invention further relates to a nucleic acid molecule according to above, wherein the said BSSL variant comprises less than 16 repeat units. In the present context the term "repeat unit" designates one of the repeated units of 33 nucleotides each which are indicated in SEQ ID NO: 1 in the Sequence Listing.

In further aspects, the invention relates to a nucleic acid molecule according to above which encodes a polypeptide, the amino acid sequence of which is at least 90% homologous with the amino acid sequence shown as SEQ ID NO: 5, 6 or 9 in the Sequence Listing, as well as a nucleic acid molecule which encodes a polypeptide, the amino acid sequence of which is at least 90% homologous with the amino acid sequence shown as SEQ ID NO: 7 in the Sequence Listing, with the exception for those nucleic acid molecules which encode polypeptides which have an asparagine residue at position 187.

The invention also relates to a polypeptide shown as SEQ ID NO: 5, 6, 7 or 9 in the Sequence Listing, as well as a polypeptide encoded by a nucleic acid sequence according to above.

The invention further relates to a hybrid gene comprising a nucleic acid molecule according to above, a replicable expression vector comprising such a hybrid gene, and a cell harbouring such a hybrid gene. This cell may be a prokaryotic cell, a unicellular eukaryotic organism or a cell derived from a multicellular organism, e.g. a mammal.

In the present context the term "hybrid gene" denotes a nucleic acid sequence comprising on the one hand a nucleic acid sequence encoding a BSSL variant as defined above and on the other hand a nucleic acid sequence of the gene which is capable of mediating the expression of the hybrid gene product. The term "gene" denotes an entire gene as well as a subsequence thereof capable of mediating and targeting the expression of the hybrid gene to the tissue of interest. Normally, said subsequence is one which at least harbours one or more of a promoter region, a transcriptional start site, 3' and 5' non-coding regions and structural sequences.

The hybrid gene is preferably formed by inserting in vitro the nucleic acid sequence encoding the BSSL variant into the gene capable of mediating expression by use of techniques known in the art. Alternatively, the nucleic acid sequence encoding the BSSL variant can be inserted in vivo by homologous recombinantion.

In the present context, the term "replicable" means that the vector is able to replicate in a given type of host cell into which it has been introduced. Immediately upstream of the nucleic acid sequence there may be provided a sequence coding for a signal peptide, the presence of which ensures secretion of the BSSL variant expressed by host cells harbouring the vector. The signal sequence may be the one naturally associated with the nucleic acid sequence or of another origin.

The vector may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication; examples of such a vector are a plasmid, phage, cosmid, mini-chromosome or virus. Alternatively, the vector may be one which, when introduced in a host cell, is integrated in the host cell genome and replicated together with the chromosome(s) into which it has been integrated. Examples of suitable vectors are a bacterial expression vector and a yeast expression vector. The vector of the invention may carry any of the nucleic acid sequences of the invention as defined above.

In another aspect, the invention relates to a process for the production of a recombinant polypeptide, said process comprising (i) inserting a nucleic acid molecule according to above in a hybrid gene which is able to replicate in a specific host cell or organism; (ii) introducing the resulting recombinant hybrid gene into a host cell or organism; (iii) growing the resulting cell in or on a culture medium, or identifying and reproducing an organism, for expression of the polypeptide; and (iv) recovering the polypeptide.

The medium used to grow the cells may be any conventional medium suitable for the purpose. A suitable vector may be any of the vectors described above, and an appropriate host cell may be any of the cell types listed above. The methods employed to construct the vector and effect introduction thereof into the host cell may be any methods known for such purposes within the field of recombinant DNA. The recombinant human BSSL variant expressed by the cells may be secreted, i.e. exported through the cell membrane, dependent on the type of cell and the composition of the vector.

If the BSSL variant is produced intracellularly by the recombinant host, that is, is not secreted by the cell, it may be recovered by standard procedures comprising cell disrupture by mechanical means, e.g. sonication or homogenization, or by enzymatic or chemical means followed by purification.

In order to be secreted, the DNA sequence encoding the BSSL variant should be preceded by a sequence coding for a signal peptide, the presence of which ensures secretion of the BSSL variant from the cells so that at least a significant proportion of the BSSL variant expressed is secreted into the culture medium and recovered.

The invention also relates to an expression system, comprising a hybrid gene which is expressible in a host cell or organism harbouring said hybrid gene, so that a recombinant polypeptide is produced when the hybrid gene is expressed, said hybrid gene being produced by inserting a nucleic acid sequence according above into a gene capable of mediating expression of the said hybrid gene.

A possible process for producing a recombinant BSSL variant of the invention is by use of transgenic non-human mammals capable of excreting the BSSL variant into their lk. The use of transgenic non-human mammals has the advantage that large yields of the recombinant BSSL variant are obtainable at reasonable costs and, especially when the non-human mammal is a cow, that the recombinant BSSL variant is produced in milk which is the normal constituent of, e.g., infant formulae so that no extensive purification is needed when the recombinant BSSL variant is to be used as a nutrient supplement in milk-based products.

Furthermore, production in a higher organism such as a non-human mammal normally leads to the correct processing of the mammalian protein, e.g. with respect to post-translational processing as discussed above and proper folding. Also large quantities of a substantially pure BSSL variant may be obtained.

Accordingly, the expression system referred to above may be a mammalian expression system comprising a DNA sequence encoding a BSSL variant inserted into a gene encoding a milk protein of a non-human mammal, so as to form a hybrid gene which is expressible in the mammary gland of an adult female of a mammal harbouring said hybrid gene.

The mammary gland as a tissue of expression and genes encoding milk proteins are generally considered to be particularly suitable for use in the production of heterologous proteins in transgenic non-human mammals, as milk proteins are naturally produced at high expression levels in the mammary gland. Also, milk is readily collected and available in large quantities. In the present connection, the use of milk protein genes in the production of a recombinant BSSL variant has the further advantage that it is produced under conditions similar to the its natural production conditions in terms of regulation of expression and production location (the mammary gland).

When used in a transgenic mammal, the hybrid gene referred to above preferably comprises a sequence encoding a signal peptide so as to enable the hybrid gene product to be secreted correctly into the mammary gland. The signal peptide will typically be the one normally found in the milk protein gene in question or one associated with the DNA sequence encoding the BSSL variant. However, also other signal sequences capable of mediating the secretion of the hybrid gene product to the mammary gland are relevant. Of course, the various elements of the hybrid gene should be fused in such a manner as to allow for correct expression and processing of the gene product. Thus, normally the DNA sequence encoding the signal peptide of choice should be precisely fused to the N-terminal part of the DNA sequence encoding the BSSL variant. In the hybrid gene, the DNA sequence encoding the BSSL variant will normally comprise its stop codon, but not its own message cleavance and polyadenylation site. Downstream of the DNA sequence encoding the BSSL variant, the mRNA processing sequences of the milk protein gene will normally be retained.

A number of factors are contemplated to be responsible for the actual expression level of a particular hybrid gene. The capability of the promoter as well of other regulatory sequences as mentioned above, the integration site of the expression system in the genome of the mammal, the integration site of the DNA sequence encoding the BSSL variant in the milk protein encoding gene, elements conferring post-transcriptional regulation and other similar factors may be of vital importance for the expression level obtained. On the basis of the knowledge of the various factors influencing the expression level of the hybrid gene, the person skilled in the art would know how to design an expression system useful for the present purpose.

The milk protein gene to be used may be derived from the same species as the one in which the expression system is to be inserted, or it may be derived from another species. In this connection it has been shown that the regulatory elements that target gene expression to the mammary gland are functional across species boundaries, which may be due to a possible common ancestor (Hennighausen et al., 1990).

Examples of suitable genes encoding a milk protein or effective subsequences thereof to be used in the construction of an expression system of the invention, are normally found among whey proteins of various mammalian origins, e.g. a whey acidic protein (WAP) gene, preferably of murine origin, and a β-lactoglobulin gene, preferably of ovine origin. Also casein genes of various origins may be found to be suitable for the transgenic production of a BSSL variant, e.g. bovine αS1-casein and rabbit β-casein. The presently preferred gene is a murine WAP gene as this has been found to be capable of providing a high level of expression of a number of foreign human proteins in milk of different transgenic animals (Hennighausen et al, 1990).

Another sequence preferably associated with the expression system of the invention is a so-called expression stabilizing sequence capable of mediating high-level expression. Strong indications exist that such stabilizing sequences are found in the vicinity of and upstreams of milk protein genes.

Included in the invention is also a process of producing a transgenic non-human mammal capable of expressing a BSSL variant, comprising (a) introducing an expression system according to above into a fertilized egg or a cell of an embryo of a non-human mammal so as to incorporate the expression system into the germine of the mammal and (b) developing the resulting introduced fertilized egg or embryo into an adult female non-human mammal.

The incorporation of the expression system into the germline of the mammal may be performed using any suitable technique, e.g. as described in "Manipulating the Mouse Embryo"; A Laboratory Manual, Cold Spring Harbor Laboratory Press, 1986. For instance, a few hundred molecules of the expression system may be directly injected into a fertilized egg, e.g. a fertilized one cell egg or a pro-nucleus thereof, or an embryo of the mammal of choice, and the microinjected eggs may then be transferred into the oviducts of pseudopregnant foster mothers and allowed to develop.

The process of producing a transgellic non-human mammal capable of expressing a BSSL variant, can also comprise a process wherein the said mammal is substantially incapable of expressing BSSL from the mammal itself. Such a process comprises (a) destroying the BSSL expressing capability of the mammal so that substantially no mammalian BSSL is expressed and inserting an expression system according to above into the germline of the mammal in such a maimer that a BSSL variant is expressed in the mammal; and/or (b) replacing the mammalian BSSL gene or part thereof with an expression system as defined above.

The mammalian BSSL expressing capability can conveniently be destroyed by introduction of mutations in the DNA sequence responsible for the expression of BSSL. Such mutations may comprise mutations which make the DNA sequence out of frame, introduction of a stop codon, or a deletion of one or more nucleotides of the DNA sequence.

The mammalian BSSL gene or a part thereof may be replaced with an expression system as defined above or with a DNA sequence encoding the BSSL variant by use of the well known principles of homologous recombination.

In a further important aspect, the invention relates to a transgenic non-human mammal harbouring in its genome a DNA sequence according to above. The said DNA sequence can preferably be present in the germline of the mammal, and in a milk protein gene of the mammal. The transgenic non-human mammal can preferably be selected from the group consisting of mice, rats, rabbits, sheep, pigs and cattle.

Included in the invention are also progeny of a transgenic non-human mammal according to above as well as milk obtained from such a transgenic non-human mammal.

The invention further relates to an infant formula comprising milk according to above, and an infant formula comprising a BSSL variant as defined above. The infant formula may be prepared using conventional procedures and contain any necessary additives such as minerals, vitamins etc.

In further aspects, the invention relates to a pharmaceutical composition comprising a BSSL variant as defined above, as well as such a BSSL variant for use in therapy.

In yet further aspects, the invention relates to the use of a BSSL variant as defined above for the manufacture of a medicament for the treatment of a pathological condition related to exocrine pancreatic insufficiency; cystic fibrosis; chronic pancreatitis; fat malabsorption; malabsorption of fat soluble vitamins; fat malabsorption due to physiological reasons. The invention also relates to the use of a BSSL variant for the manufacture of a medicament for the improvement of the utilization of dietary lipids, particularly in preterm born infants.

EXAMPLES

1. EXPRESSION OF RECOMBINANT BSSL IN EUKARYOTIC AND PROKARYOTIC CELLS

1.1. EXPERIMENTAL PROCEDURES

1.1.1. Recombinant Plasmids

The plasmid pS146 containing the 2.3 kb human BSSL cDNA (Nilsson et al., 1990) cloned into pUC19 was digested with HindIII and SalI and the BSSL cDNA was introduced into a bovine papilloma virus (BPV) expression vector, pS147 (FIG. 1). This vector contains the human BSSL cDNA under control of the murine metallothioneine 1 (mMT-1) enhancer and promoter element (Pavlakis & Hamer, 1983). The mRNA processing signals are provided by a genomic fragment containing part of exon II, intron II, exon III and downstream elements of the rabbit β-globin gene. This transcriptional unit was cloned into a vector containing the entire BPV genome. Transcription was unidirectional for BPV and the BSSL transcriptional unit. For propagation of the vector in $E. coli$ the vector also contains pML2d, a pBR322 derivative (Sarver et al., 1982).

The expression vector pS147 was co-transfected with a vector encoding the neomycin resistance gene driven by the Harvey Sarcoma virus 5'-Long terminal repeat and Simian virus 40 polyadenylation signals (Lusky & Botchan, 1984).

For expression of BSSL in $E. coli$, the BSSL cDNA was subcloned as a NdeI-BamHI fragment from plasmid pT7-7 (Ausubel et al., 1992) into plasmid pGEMEX-1 (Promega, Madison, Wis., U.S.A.) (Studier & Moffat, 1986). By this cloning procedure the T7 gene 10 encoding sequence was replaced by the BSSL gene coding for the mature protein preceded by a start codon. The final expression vector, pGEMEX/BSSL, was verified by DNA sequencing using specific BSSL internal primers.

1.1.2. Mutagenesis

Nucleotide number 1 was assigned to the A in the initiation codon ATG. For amino acid numbering the first methionine in the signal peptide is −23 and the first amino acid residue of the mature protein, an alanine, is assigned number 1.

For the construction of the deletion variant A (SEQ ID NO: 4), two PCR primers were synthesized, PCR-1 and PCR-2 (Table 1). The HindIII, SalI and BamHI sites were created for cloning into different plasmids. The BclI site was generated in the BSSL sequence without altering the amino acid sequence. This was done to facilitate addition of synthetic DNA to obtain the other variants. The primer PCR-2 contains two synthetic stop codons. The resulting PCR fragments were digested with BamHI and HindIII and cloned into pUC18 for sequence analysis. This plasmid was designated pS157. The correct PCR fragment was inserted into the BPV expression vector by fusion to the BSSL sequence at the unique Asp700 site (position 1405 in the BSSL cDNA) and the SalI site in front of the β-globin gene fragment, resulting in pS257.

The B-variant construction (SEQ ID NO: 5) was done using oligonucleotides number 3,4,7 and 8 (Table 1). The annealed oligonucleotides encodes the very C-terminal amino acid sequence, representing lysine 712 to phenylalanine 722 in the full-length protein. This fragment was fused to glutamine 535. A translational stop was inserted directly after the last phenylalanine. This fragment contains a BclI site in the 5'-end and a SalI site in the 3'-end, allowing introduction into pS157. The resulting plasmid was digested with Asp700 and SalI and the 313 bp fragment was introduced into the expression vector as described above. The resulting plasmid was designated pS258.

TABLE 1

Synthetic oligonucleotides used for construction of the BSSL variants. Nucleotides of restriction sites are underlined. Translational stop signals are indicated by bold letters. The altered codon in variant N is indicated in PCR-3 by bold letters and an asterisk.

| Oligo-nucleotide | Sequence (5'-3') |
|---|---|
| PCR-1 (SEQ ID NO: 10) | CGGGATCCGAAGCCCTTCGCCACCCCCACG |
| PCR-2 (SEQ ID NO: 11) | CGAAGCTTGTCGACTTACTACTGATCAGTCACTGTGGGCAGCGCCAG |
| PCR-3 (SEQ ID NO: 12) | GGGAATTCTGGCCATTGCTTGGGTGAAGAGGAATATCGCGGCCTTCGGGGGGGACCCCAACCAGATCACGCTCTTCGGGGAGTCT* |
| PCR-4 (SEQ ID NO: 13) | CGGGATCCCACATAGTGCAGCATGGGGTACTCCAGGCC |
| 1 (SEQ ID NO: 14) | GATCAGGGGGCCCCCCCCGTGCCGCCCACGGGTGACTCCGGG |
| 2 (SEQ ID NO: 15) | GCCCCCCCCGTGCCGCCCACGGGTGACTCCAAGGAAGCTCAGA |
| 3 (SEQ ID NO: 16) | TGCCTGCAGTCATTAGGTTTTAGTAAGTCGACA |
| 4 (SEQ ID NO: 17) | AGCTTGTCGACTTACTAAAACCTAATGACTG |
| 5 (SEQ ID NO: 18) | CAGGCATCTGAGCTTCCTTGGAGTCACCCGTGGGCGGCACGGGGGGGGCCCCGGA |
| 6 (SEQ ID NO: 19) | GTCACCCGTGGGCGGCACGGGGGGGGCCCCCT |
| 7 (SEQ ID NO: 20) | GATCAGAAGGAAGCTCAGA |
| 8 (SEQ IQ NO: 21) | CAGGCATCTGAGCTTCCTTCT |

In order to construct the gene encoding the C-variant (SEQ ID NO: 6), oligonucleotides 1 to 6 (Table 1) were used. The annealed DNA fragment contains two repetitions, encoding eleven amino acids, identical to consensus (Nilsson et al., 1990), inserted between glutamine 535 and the lysine 712 to phenylalanine 722 sequence. This fragment also contains a BclI site in the 5'-end and a SalI site in the 3'-end, allowing the same cloning strategy as above. The resulting plasmid was designated pS259.

For the construction of variant N (non-N-glycosylated variant, SEQ ID NO: 7), two PCR primers (PCR-3 and PCR-4 in Table 1), were synthesized. The EcoRI and BamHI sites were created for cloning of the 360 bp PCR product into pUC19 for sequence analysis. The potential N-linked glycosylation site at asparagine 187, was changed to a glutamine. The modified sequence was isolated as a BalI-HindIII fragment and cloned into SacI and HindIII digested pUC19 together with a SacI and BalI fragment containing the mMT-1 promoter and 5'-end of BSSL cDNA. An approximately 1.2 kb SacI-DraIII fragment was isolated from this plasmid and inserted in the mMT-1 element and BSSL cDNA sequence, respectively, within the expression vector. The resulting plasmid was designated pS299.

1.1.3. Mammalian Cell Culture and Transfections

The vectors were co-transfected into the murine cell line C127 (ATCC CRL 1616) according to the calcium-phosphate precipitation method (Graham & Van der Eb, 1973).

The C127 cells were cultured in Ham's F12-Dulbecco's Modified Eagle's medium (DMEM) (1:1) supplemented with 10% fetal calf serum. Neomycin resistant cell clones were selected with 1.5 mg×ml$^{-1}$ of G418 and after 10–15 days resistant cell clones were isolated from the master plates and passaged for analysis.

1.1.4. Bacterial Strains and Culture Conditions

For expression experiments the vector pGEMEX/BSSL was transformed into E. coli strains JM109(DE3) and BL21 (DE3)pLysS. The expression experiments were carried out as described by Studier et al. (1986). After harvesting of bacteria, the cells were pelleted by centrifugation (5,000×g for 10 min at 4° C.). For preparation of periplasm- and cytoplasm fractions, the pellet was resuspended in 4 ml 20 mM Tris-Cl/20% sucrose, pH 8.0, 200 µl 0.1M EDTA and 40 µl lysozyme (15 mg/ml in water) per gram of pellet. The suspension was incubated on ice for 40 minutes. 160 µl 0.5M MgCl$_2$ per gram of pellet was added, whereafter the suspension was centrifuged for 20 min at 12,000×g. The resulting supernatant contains periplasmic proteins and the pellet represents the cytoplasmic fraction. Alternatively, for preparation of soluble proteins, the cells were suspended in 40 mM Tris-Cl, 0.1 mM EDTA, 0.5 mM phenylmethylsulphonylfluoride, pH 8.2, freeze-thawed and sonicated several times to lyse. The cell lysate was centrifuged (30,000×g for 30 min at 25° C.).

1.1.5. Nucleic Acid Analysis

RNA and DNA were prepared from isolated mammalian cell lines or E. coli cells (Ausubel et al., 1992). The RNA or DNA were fractionated on agarose gels and blotted onto GeneScreen Plus (New England Nuclear) and hybridized according to the supplier's instructions.

1.1.6. Preparation of Native Enzyme

Bile salt-stimulated lipase was purified from human milk as previously described (Blackberg & Hernell, 1981). The purified preparation was homogenous as judged by SDS-PAGE and had a specific activity of 100 µmol fatty acid released×min$^{-1}$ and mg$^{-1}$ when assayed with long-chain triacylglycerol as substrate.

1.1.7. Enzyme Assay

The enzyme assay was as described (Blackberg & Hernell, 1981) using triolein emulsified with gum arabic as substrate. The incubations were carried out with 10 mM sodium cholate as activating bile salt. When the bile salt dependency was tested bile salts (sodium cholate or sodium deoxycholate, Sigma Chem. Co.) were added to the concentrations given in FIG. 3.

1.1.8. Western Blotting

In order to obtain significant reactions in the blotting experiments the conditioned media were concentrated by chromatography on Blue Sepharose (Pharmacia LKB Biotechnology). The respective media were mixed with Blue Sepharose (approx 10 ml of medium per ml of gel). The gel was washed with (10 ml per ml of gel) with 0.5M Tris-Cl buffer, pH 7.4, containing 0.1M KCl. The enzyme activity was eluted with 1.5M KCl in the same buffer. By this procedure a 25–30-fold concentration was obtained as well as a 3–5-fold purification. SDS-PAGE was performed on 10% polyacrylamide gels essentially according to Laemmli (1970). After transfer to nitrocellulose membranes and incubation with a polyclonal rabbit antiserum to purified BSSL detection was made using goat anti-rabbit IgG conjugated with alkaline phosphatase and a developing kit from Bio-Rad.

1.1.9. Treatment with N-Glycosidase F

To 10 µl of variant B, containing a BSSL activity of 2.5 µmol fatty acid released×min$^{-1}$, 1 µl of 1M β-mercaptoethanol and 0.5 µl of 10% (w/v) SDS was added. After boiling for 5 min, 10 µl 0.1M Na-phosphate buffer, pH 8.0, 6 µl 0.1M EDTA, 4 µl 7.5% (w/v) Nonidet P 40 and 5 µl (1U) N-glycosidase F (Boehringer Mannheim) were added. As a control the same amount of variant B was treated identically except that no glycosidase was added. After an overnight incubation at 37° C., the samples were run on SDS-PAGE and blotted using the polyclonal rabbit BSSL antiserum.

1.2. RESULTS

1.2.1. Construction of the BSSL Variants

The modifications of the BSSL variants in relation to the full-length BSSL are summarized in Table 2 and FIG. 1. The strategies used for generation of these variants are described in Section 1.1. For variant A (SEQ ID NO: 4), a stop codon was introduced after glutamine at position 535 thereby removing the last 187 amino acids of the full-length protein. For variant B (SEQ ID NO: 5) the domain encoding the 11 very C-terminal amino acids and the original translational stop was fused to glutamine-535. Hence, this variant lacks all the repeats. For variant C (SEQ ID NO: 6) a fragment containing two repeats having a sequence identical to consensus (Nilsson et al., 1990) were inserted between glutamine-535 and the lysine-712 to phenylalanine-722 sequence.

To analyze the importance of the only tentative N-linked carbohydrate structure, positioned close to the active site serine-194, a variant was constructed. Variant N (SEQ ID NO: 7) was obtained by altering the potential N-glycosylation site at asparagine-187 to a glutamine.

TABLE 2

The amino acid sequence of the BSSL variants in relation to that of human BSSL.

| Variant | Deleted residues | Changed residues |
|---|---|---|
| A (SEQ ID NO: 4) | 536–722 | |
| B (SEQ ID NO: 5) | 536–711 | |
| C (SEQ ID NO: 6) | 536–568, 591–711 | |
| N (SEQ ID NO: 7) | | Asn 187→Gln |

1.2.2. Characterization of Recombinant DNA in the Mammalian Cell Lines

DNA samples were prepared from the cell lines transfected with the expression vectors encoding the different BSSL variants. The prepared DNA was digested with BamHI, fractionated on agarose gels and transferred to membranes for hybridization. The probe used was $^{32}$P-labelled BSSL cDNA. The hybridization results confirmed the presence of the recombinant genes and also that the vector copy number was approximately equal in the different cell lines (FIG. 2). The positions of the hybridizing fragments reflected the different lengths of the various BSSL sequences and were in agreement with the expected sizes. The positions were also similar to the bacteria derived DNA used in the transfection experiment, indicating that no major rearrangement of vector DNA had occurred in the cell lines (FIG. 2). The upper hybridization signals in the DNA sample representing variant A were probably due to partial digestion.

1.2.3. Expression of mRNA for Full-Length and Mutated BSSL in Mammalian Cells To analyze the expression of the different recombinant BSSL genes RNA was prepared from the isolated cell lines. Northern blot experiment and hybridization with $^{32}$P-labelled BSSL cDNA showed that recombinant mRNA was detectable in all cell lines harboring a BSSL vector (FIG. 3). No hybridization was found in the control sample derived from a cell line containing an identical vector except for BSSL cDNA (FIG.3).

The different lengths of the hybridizing mRNAs were in accordance with the modificaitons of the cDNAs. The steady state levels of recombinant BSSL mRNA is not known, but it was observed with two populations of cell lines as well as with isolated clones. The presence of equal amounts of RNA in the different samples was confirmed by hybridization to a murine β-actin probe (FIG. 3, lower panel).

1.2.4. Production of Full-Length and Variants of BSSL in Mammalian Cells

Media from individual clones of the C127-cells, transfected with full-length BSSL and the different mutated forms, were collected and assayed for BSSL activity (FIG. 4). For the full-length molecule and variants N, B and C the activities in the clones with the highest expression ranged from 0.7 to 2.3 μmol fatty acid released×min$^{-1}$×medium$^{-1}$. With a specific activity comparable to that of the native milk BSSL this would correspond to expression levels of 7–23 μg×ml medium$^{-1}$. For variant A all the analyzed clones had activities below 0.05 μmol fatty acid released×min$^{-1}$ and ml of medium$^{-1}$. Concentration on Blue-Sepharose and lyophilization of the clone showing the highest activity revealed that an active enzyme indeed was expressed, albeit at very low levels. The possibility that the low activity obtained with variant A in part could be explained by a considerably lower specific activity could not be ruled out.

Western blots from clones of the different transfection experiments are shown in FIG. 5A. The apparent $M_r$ of the BSSL variants were as expected. It should be noted, however, that for full-length BSSL as well as for variants B and C a double band was obtained. Because all three have the single N-glycosylation site intact whereas variant N, which showed no double band, lacks that site, a likely explanation was that the double band resulted from differences in N-glycosylation. Therefore variant B was subjected to digestion with N-glycosidase F. As shown in FIG. 5B, only trace amounts of the upper band remained while the lower band increased in strength indicating that only part of the expressed variant was N-glycosylated.

One of the characteristics of BSSL is its specific activation by primary bile salts, e.g. cholate (Hernell, 1975). All the different recombinant forms of BSSL showed the same concentration dependency for cholate activation (FIG. 6). A maximal activity was obtained at about 10 mM in the assay system used. When cholate was exchanged for deoxycholate (a secondary bile salt) no such activation occurred. Thus, the recombinant full-length as well as the different variants showed the same specificity regarding bile salt activation.

1.2.5. Expression and Biochemical Characterization of Full-Length BSSL in E. coli Two E. coli strains JM109(DE3) and BL21(DE3)pLysS (Studier et al., 1986) were transformed with the expression vector pGEMEX/BSSL containing the human BSSL cDNA under control of the T7 promoter. Transformants from both strains were identified, cultured and induced with IPTG for about 90 min (Studier et al., 1986). Analysis of total mRNA by Northern blot using the BSSL cDNA as a $^{32}$P-labeled probe demonstrated that expression was efficiently induced in both strains and that the transcription was tightly regulated (FIG. 7A). The apparent size of the recombinant BSSL mRNA, appoximately 2.4 kb, is in agreement with the expected length. SDS-PAGE separation of protein samples and immunodetection with anti-BSSL antibodies showed that full-length BSSL was efficiently produced in E. coli (FIG. 7B). More of the protein was secreted to the periplasm in the BL21(DE3)pLysS strain than in JM109(DE3) (FIG. 7B).

IPTG-induced E. coli cultures contained active soluble BSSL corresponding to 0.5–4 μg of BSSL protein/ml culture. Western blotting showed that between 20 and 60% of the reactive material was in the insoluble pellet. Uninduced bacteria did not contain any significant BSSL activity.

The lipase activity from cultured bacteria showed the same bile salt dependence as native milk BSSL.

2. PURIFICATION AND CHARACTERIZATION OF RECOMBINANT FULL-LENGTH AND MUTATED FORMS OF BILE SALT-STIMULATED LIPASE

2.1. EXPERIMENTAL PROCEDURES

2.1.1. Enzymes and Enzyme Variants

Recombinant full-length BSSL and BSSL variants B, C and N were constructed and expressed as previously described. Compared to the native enzyme Variant B (SEQ ID NO: 5) lacks all 16 unique, O-glycosylated, proline-rich, C-terminal repeats (aa 536–711) but with the most C-terminal fragment (aa 712–722) fused to glutamine-535. Variant C (SEQ ID NO: 6) contains the same C-terminal fragment and two repeats of 11 residues between glutamine-535 and lysine-712. In variant N (non-N-glycosylated variant, SEQ ID NO: 7) the asparagine-187 responsible for the only N-linked sugar was exchanged for a glutamine residue. Native BSSL was purified from human milk as described (Blackberg & Hernell, 1981).

2.1.2. Enzyme Assay

Lipase activity was assayed as described (Blackberg & Hernell, 1981) using triolein emulsified in gum arabic as substrate. Sodium cholate (10 mM) was used as activating bile salt. Different modifications of the assay are given in legends to figures.

2.1.3. Preparation of Immunosorbent

Purified milk BSSL (5 mg) was coupled to Sepharose using CNBr as described by the manufacturer. 40 ml of a polyclonal antiserum raised in rabbit against purified milk BSSL was passed over the column. Specific antibodies were eluted with 0.1M glycine-HCl, pH 2.5. The pH was immediately adjusted to approx 8 with solid Tris. After desalting and lyophilization 6 mg of the affinity purified antibodies was coupled to Sepharose as described above.

2.1.4. Purification Procedure

Conditioned culture media containing 5–25 µg of recombinant expressed BSSL or BSSL variant was mixed Blue Sepharose (Pharmacia, Sweden) 10 ml media per ml of settled gel. After end-to-end mixing for 30 min the gel was rinsed with 0.05M Tris-Cl, pH 7.0, 0.05M KCl and the lipase activity eluted with 0.05M Tris-Cl, pH 7.0, 1.5M KCl. The activity peak was pooled and dialyzed against 5 mM sodium veronal, pH 7.4, 0.05M NaCl. The dialyzate was applied to a heparin-Sepharose column. The column was eluted with a gradient 0.05 to 1.0M NaCl in 5 mM sodium veronal buffer, pH 7.4. Fractions containing lipase activity were pooled and applied to an immunosorbent column. After rinsing with 0.05M Tris-Cl, pH 7.5, 0.15M NaCl lipase bound was eluted with 0.1M glycin-HCl, pH 2.5. The pH of the fractions was immediately adjusted to approx 8 with solid Tris.

2.1.5. Electrophoresis

Sodium dodecyl sulphate polyacrylamide gel electrophoresis (SDS-PAGE) was performed essentially according to Laemmli (1970). Proteins were stained with Commassie Brilliant Blue.

2.1.6. N-terminal sequence analysis

Amino acid sequence analysis were performed on an Applied Biosystems Inc. 477A pulsed liquid-phase sequencer and an on-line phenylthiohydantoin 120A analyzer with regular cycle programs and chemicals from the manufacturer. Calculated from a sequenced standard protein (β-lactoglobulin) initial and repetitive yields were 47% and 97%, respectively.

2.2. RESULTS

2.2.1. Purification of Recombinant BSSL and BSSL Variants.

Chromatography on Blue Sepharose of conditioned media was primarily used to as a concentrating step. The subsequent chromatography on heparin-Sepharose gave an initial purification mainly by removing most of the albumin present in the culture medium. This step also showed that the recombinant BSSL molecules all retained the heparin binding. After the immunosorbent all BSSL variants appeared more than 90% pure, as judged by SDS-PAGE (FIG. 8). The full-length enzyme as well as variant B and C migrated as a doublet. The apparent $M_r$ of the different variants are shown in Table 3. N-terminal sequence analysis gave a single sequence for all variants for 8 cycles: Ala-Lys-LeuGly-Ala-Val-Tyr-Thr-.

2.2.2. Lipase Activity

In Table 3 the apparent molecular weight of the different preparations is shown. The specific activities of the preparations ranged from 75 to 120 µmol free fatty acid released per min and mg protein. Consequently no significant difference in activity between full-length BSSL and the BSSL variants could be observed.

The preparations all showed an absolute requirement for primary bile salt (sodium cholate) for activity against emulsified long-chain triacylglycerol (FIG. 9A). Sodium deoxocholate did render any of the variants active (data not shown). However, when combining the different bile salts deoxycholate had two effects (FIG. 9B and C). Firstly, it lowered the concentration of cholate needed for activation, and secondly it inhibited enzyme activity at higher bile salt concentration.

TABLE 3

Apparent $M_r$ of recombinant full-length BSSL and BSSL variants.

| Enzyme | $M_r$ (kDa) Determined by SDS-PAGE |
|---|---|
| Full-length | 105, 107 |
| Variant B | 63, 65 |
| Variant C | 60, 62 |
| Variant N | 95 |

2.2.3. Stability of Recombinant BSSL and BSSL Variants

Recombinant BSSL as well as the BSSL variants showed the same pH-stability as native milk BSSL (FIG. 10). An inactivation occured in all cases at a pH around 2.5–3. Above pH 3 all variants were completely stable provided the protein concentration was high enough. This was acomplished by adding bovine serum albumin or ovalbumin (data not shown). Diluted samples were less stable at all tested pH but the threshold remained the same (data not shown). FIG. 11 shows the heat stability of the recombinant enzymes compared to the native milk enzyme. At a temperature of 37°–40° C. the activity starts to decrease. The variants (B, C, N) appears to be somewhat less stable than the full-length recombinant enzyme and the milk enzyme. However, if the protein concentration was raised by adding bovine serum albumin all variants was stable also at 40° C. (FIG. 11).

Native milk BSSL and all the recombinant variants were all sensitive to trypsin. A time dependent inactivation was obtained (FIG. 12). If, however, bile salts, i.e. cholate, was included in the buffer the lipase variants were protected and lipase activity retained (FIG. 12).

Thus, with regard to a number of in vitro characteristics, i.e. bile salt activation, heparin binding, pH- and temperature stability and bile salt protection against inactivation by proteases, no significant differences were observed when comparing the different BSSL variants with native milk BSSL.

3. EXPRESSION IN TRANSGENIC ANIMALS

3.1. CONSTRUCTION OF EXPRESSION VECTORS

To construct an expression vector for production of recombinant human BSSL variant in milk from transgenic animals, the following strategy was employed (FIG. 13).

Three plasmids containing different parts of the human BSSL gene (pS309, pS310 and pS311) were obtained using the methods described in Lidberg et al. (1992). The plasmid pS309 contains a SphI fragment covering the BSSL gene from the 5' untranscribed region to part of the fourth intron. The plasmid pS310 contains a SacI fragment covering a BSSL variant gene sequence from part of the first intron to a part of the sixth intron. The plasmid pS311, finally, contains a BamHI fragment covering the BSSL gene from a major part of the fifth intron and the rest of the intron/exon structure with deletions in exon 11. The deleted sequences are 231 bp which results in a sequence encoding a BSSL variant which has exactly 77 amino acids or seven repeats less than the full-length BSSL. The nucleotide 20 sequence of the resulting BSSL variant ("Variant T") is shown in the Sequence Listing as SEQ ID NO: 8. The amino acid sequence of variant T is shown in the Sequence Listing as SEQ ID NO: 9.

Due to the highly repetitive sequence in exon 11 of the human BSSL gene, relatively high frequencies of rearrangements can be anticipated when this sequence is cloned into a plasmid and propagated in bacteria. Based on this assumption, one desired BSSL variant which contains a truncated exon 11, was identified, isolated and subjected to sequence analysis.

Another plasmid, pS283, containing a part of the human BSSL cDNA cloned into the plasmid pUC19 at the HindIII and SacI sites was used for fusion of the genomic sequences. Plasmid pS283 was also used to get a proper restriction enzyme site, KpnI, located in the 5' untranslated leader sequence of BSSL.

Plasmid pS283 was digested with NcoI and SacI and a fragment of about 2.7 kb was isolated by electrophoresis. Plasmid pS309 was digested with NcoI and BspEI and a fragment of about 2.3 kb containing the 5'-part of the BSSL gene was isolated. Plasmid pS310 was digested with BspEI and SacI and a fragment of about 2.7 kb containing a part of the middle region of the BSSL gene was isolated. These three fragments were ligated and transformed into competent E. coli, strain TG2, and transformants were isolated by ampicillin selection.

Plasmids were prepared from a number of transformants, and one plasmid, called pS312 (FIG. 14), containing the desired construct was used for further experiments.

To obtain a modification of pS311 in which the BamHI site located downstream of the stop codon was converted to a SalI site to facilitate further cloning, the following method was used: Plasmid pS311 was linearized by partial BamHI digestion. The linearized fragment was isolated and a synthetic DNA linker that converts BamHI to a SalI site (5'-GATCGTCGAC-3'), thereby destroying the BamHI site, was inserted. Since there were two potential positions for integration of the synthetic linker the resulting plasmids were analyzed by restriction enzyme cleavage. A plasmid with the linker inserted at the desired position downstream of exon 11 was isolated and designated pS313.

To obtain the final expression vector construct harbouring the human BSSL variant genomic sequences an existing expression vector, pS314, designed to mediate stage and tissue specific expression in the mammary gland cells under lactation periods was used. Plasmid pS314 contains a genomic fragment from the murine whey acidic protein (WAP) gene (Campbell et al., 1984) cloned as a NotI fragment. The genomic fragment has approximately 4.5 kb upstream regulatory sequences (URS) all the four murine WAP exons and all intron sequences and about 3 kb of sequence downstream of the last exon. A unique KpnI site is located in the first exon 24 bp upstream of the natural WAP translation initiation codon. Another unique restriction enzyme site is the SalI site located in exon 3.

The human BSSL variant genomic sequence was inserted between these sites, KpnI and SalI, by the following strategy: First, pS314 was digested with KpnI and SalI and a fragment representing the cleaved plasmid was electrophoretically isolated. Second, pS312 was digested with KpnI and BamHI and a approximately 4.7 kb fragment representing the 5'-part of the human BSSL gene was isolated. Third, pS313 was digested with BamHI and SalI and the 3'-part of the human BSSL gene was isolated. These three fragments were ligated, transformed into competent E. coli bacteria and transformants were isolated after ampicillin selection.

Plasmids were prepared from several transformants and carefully analyzed by restriction enzyme mapping and sequence analysis. One plasmid representing the desired expression vector was defined and designated pS317 (FIG. 15).

In order to remove the prokaryotic plasmid sequences, pS317 was digested with NotI. The recombinant vector element consisting of murine WAP sequence flanking the human BSSL variant genomic fragment was then isolated by agarose electrophoresis. The isolated fragment was further purified using electroelution, before it was injected into mouse embryos.

The recombinant gene for expression of human BSSL variant in milk from transgenic mice is shown in FIG. 16.

3.2. GENERATION OF TRANSGENIC ANIMALS

A NotI fragment was isolated from the plasmid pS317 according to section 3.1. This DNA fragment contained the murine WAP promoter linked to a genomic sequence encoding human BSSL variant. The isolated fragment, at a concentration of 3 ng/µl, was injected into the pronucleus of 350 C57B1/6J×CBA/2J-f$_2$ embryos obtained from donor mice primed with 5 IU pregnant mare's serum gonadotropin for superovulation. The C57B1/6J×CBA/2J-f$_1$ animals were obtained from Bomholtgård Breeding and Research Centre LTD, Ry, Denmark. After collection of the embryos from the oviductsm, they were separated from the cumulus cells by treatment with hyaluronidase in the medium M2 (Hogan et al., 1986). After washing the embryos were transferred to the medium M16 (Hogan et al., 1986) and kept in an incubator with 5% $CO_2$-atmosphere. The injections were performed in a microdrop of M2 under light paraffin oil using Narishigi hydraulic micromanipulators and a Nikon inverted microscope equipped with Nomarski optics. After injection, 267 healthy looking embryos were implanted into 12 pseudopregnant C57B1/6J×CBA/2J-f$_1$ recipients given 0.37 ml of 2.5% Avertin intraperitoneally. Mice that had integrated the transgene were identified with PCR analysis of DNA from tail biopsy specimens obtained three weeks after birth of the animals. Positive results were confirmed with Southern blot analysis.

For milk collection, female lactating animals were injected with 2 IU oxytocin intraperitoneally and 10 minutes later anaesthetized with 0.40 ml of 2.5% Avertin intraperitoneally. A milk collecting device was attached to the nipple via a siliconized tubing and milk was collected into a 1.5 ml Eppendorf tube by gentle massage of the mammary gland. The amount of milk varied, dependent on the day of lactation, between 0.1 and 0.5 ml per mouse and collection.

3.3. EXPRESSION OF BSSL VARIANT IN TRANSGENIC MICE

Transgenic mice were identified by analysis of DNA which has been prepared from excised tail samples. The tissue samples were incubated with proteinase K and phenol/chloroform extracted. The isolated DNA was used in polymerase chain reactions with primers which amplify specific fragments if the heterologous introduced DNA representing the expression vector fragment is present. The animals were also analyzed by DNA hybridization experiments to confirm PCR data and to test for possible rearrangements, structure of the integrated vector elements and to obtain information about the copy number of integrated vector elements.

In one set of experiments, 31 mice were analyzed with the two methods and the results demonstrated that 1 mice was carrying the heterologous DNA vector element derived from pS317. The result from the PCR analysis and the hybridization experiments were identical (FIG. 17). In total, 10 of 65 tested animals were found to be transgenic for pS317.

The mouse identified to carry vector DNA element (founder animal) was then mated and the F1 litter was analyzed for transgene by the same procedures.

RNA isolated from various tissues of pS317 transgenic females during lactation have been separated by agarose formaldehyde gel electrophoresis, blotted to membranes and hybridized with $^{32}$P-labelled BSSL cDNA as a probe. The obtained results show that the expression is restricted to the mammary gland during lactation (FIG. 18).

Milk samples were collected from the anesthetized founder animal treated with oxytocin to induce lactation and analyzed for the presence of recombinant human BSSL variant. This was done by SDS-PAGE, transfer to nitrocellulose membranes and incubation with polyclonal antibodies generated against native human BSSL. The obtained results demonstrated expression of recombinant human BSSL variant in milk from transgenic mice. FIG. 19 demonstrates presence of recombinant human BSSL variant in milk from transgenic mice. SDS-PAGE separation and immuunoblotting of milk samples derived from various pS317 transgenic mice show efficient production of a recombinant BSSL variant with reduced apparent molecular weight in comparison to full-length recombinant BSSL derived from milk of a mouse transgenic for pS314. The plasmid pS314 is similar to pS317, with the exception that pS314 contains full-length human BSSL cDNA instead of the genomic variant. The doublet band which is apparent in all murine milk samples is representing murine BSSL, and thus shows the cross reactivity of the antiserum. This conclusion is further supported by the observation that this doublet band is apparent in lane 9 of FIG. 19, which contains purified murine BSSL.

Stable lines of transgenic animals are generated.

In a similar manner, other transgenic animals such as rabbits, cows or sheep capable of expressing human BSSL variants may be prepared.

DEPOSITS

The following plasmids have been deposited in accordance with the Budapest Treaty at DSM (Deutsche Sammlung von Mikroorganismen und Zellkulturen):

| Plasmid | Deposit No. | Date of deposit |
| --- | --- | --- |
| pS309 | DSM 7101 | 12 June 1992 |
| pS310 | DSM 7102 | 26 February 1993 |
| pS311 | DSM 7103 | 3 March 1993 |
| pS317 | DSM 7104 | |
| pS147 | DSM 7495 | |
| pS257 | DSM 7496 | |
| pS299 | DSM 7497 | |
| pS258 | DSM 7501 | |
| pS259 | DSM 7502 | |

A. Map of the BPV based vector used for expression of the different BSSL variants.

B. A schematic representation of the different BSSL variants analyzed. FL denotes the full-length BSSL. The active site is indicated by a circle and the site for the potential N-linked carbohydrate is indicated by a triangle. The region containing the repeats is indicated as a striped area and the conserved C-terminal as a filled area.

FIG. 2

Southern blot analysis of DNA from cell lines expressing BSSL variants. DNA prepared from cell lines expressing full-length BSSL (FL), variant A (A), variant B (B), variant C (C) and variant N (N) were analyzed. 5 µg of the respective prepared cell derived DNA (left) and 1 ng of purified bacteria derived vector DNA (right), were digested with BamHI. The DNA samples were separated on an agarose gel, transferred to GeneScreen Plus membrane and hybridized with $^{32}$P-labelled human BSSL cDNA.

FIG. 3

Figure 1A:
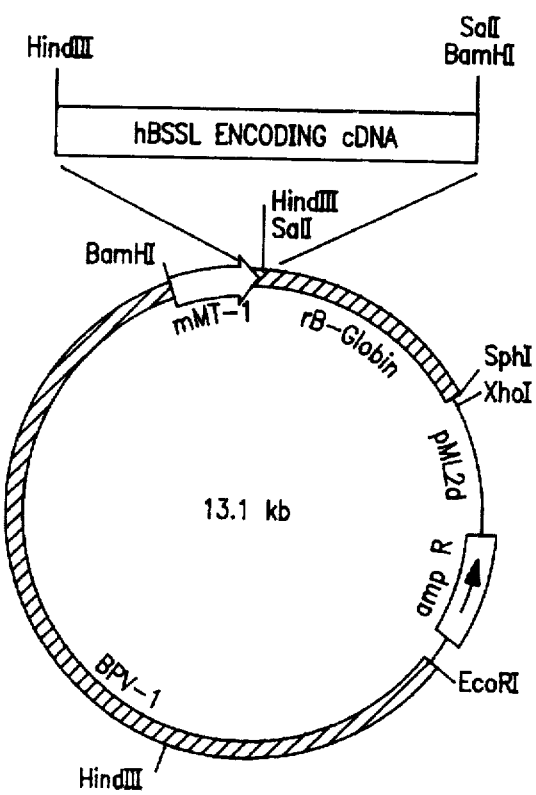
FIG. 1 (A and B)
Figure 1B:
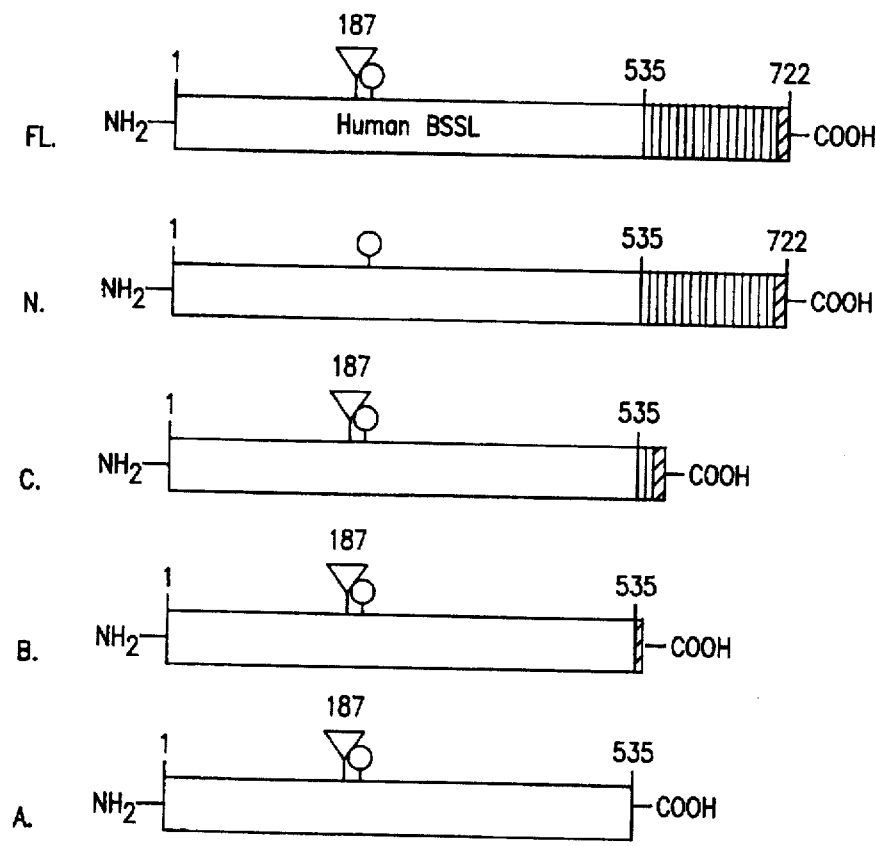

Northern blot analysis of RNA from isolated cell lines expressing recombinant BSSL variants. 10 µg of total RNA prepared from cell lines producing full-length BSSL (FL), variant A (A), variant B (B), variant C (C), variant N (N) were analyzed. RNA from a C127 cell line harboring a BPV-vector identical to the vector in FIG. 1, except for that it encodes a protein unrelated to BSSL, was used as negative control (−) (upper panel). Filters were hybridized with $^{32}$P-labelled BSSL cDNA. The filter was then rehybridized with a murine β-actin cDNA probe. The β-actin MRNA signals (lower panels) were used as an internal control for the amounts of RNA loaded onto each lane.

FIG. 4

Expression of BSSL activity in C127 cells transfected with full-length and mutated forms of human BSSL. C127 cells were transfected with different BSSL-constructs: full-length BSSL (FL), variant N (N), variant C (C), variant B (B), variant A (A). After the initial growth period individual clones were selected and allowed to grow until confluency. The number of selected clones (n) are indicated in the figure. Lipase activity was determined on the conditioned media. Values are expressed as µmol free fatty acid released×min$^{-1}$×ml of conditioned medium$^{-1}$.

FIG. 5 (A and B)

A. Western blotting of full-length and mutated recombinant BSSL. The amounts of lipase activity, expressed as µmol fatty acid released×min$^{-1}$, applied to the gel was: Full-length 0.2 (lane 1), variant N 0.16 (lane 2), variant C 0.6 (lane 3), variant B 0.8 (lane 4) and native BSSL 0.1 (lane 5). The antiserum used was raised in rabbit against BSSL purified from human milk. The position of size markers (Prestained SDS-PAGE Standards, Low Range, BioRad) are indicated to the left.

B. Western blot of N-glycosidase F treated variant B. Variant B was digested with N-glycosidase F as described in Experimental procedures. Lane 1 shows untreated and lane 2 treated variant B.

FIG. 6

Bile salt-dependency of full-length and mutated BSSL. Lipase activity was determined in the presence of varying concentrations of sodium cholate (solid lines) or sodium deoxycholate (broken lines) on conditioned media from full-length recombinant BSSL (*), variant A (□), variant B (▲), variant C (■), variant N (●) and purified human milk BSSL (o). For the A variant conditioned medium was concentrated on Blue Sepharose as described under Experimental procedures. The amount of the respective enzyme source was chosen to obtain the same level of maximal activity except for variant A which had a maximal activity of only one-tenth of the others. Control experiments showed that the growth media did not influence the level of activity or the bile salt dependency of native BSSL (data not shown).

FIG. 7(A and B)

A. Northern blot of BSSL produced by different strains of *E. coli* using pGEMEX. The bacteria were induced by IPTG as described in experimental procedures.

Figure 2:
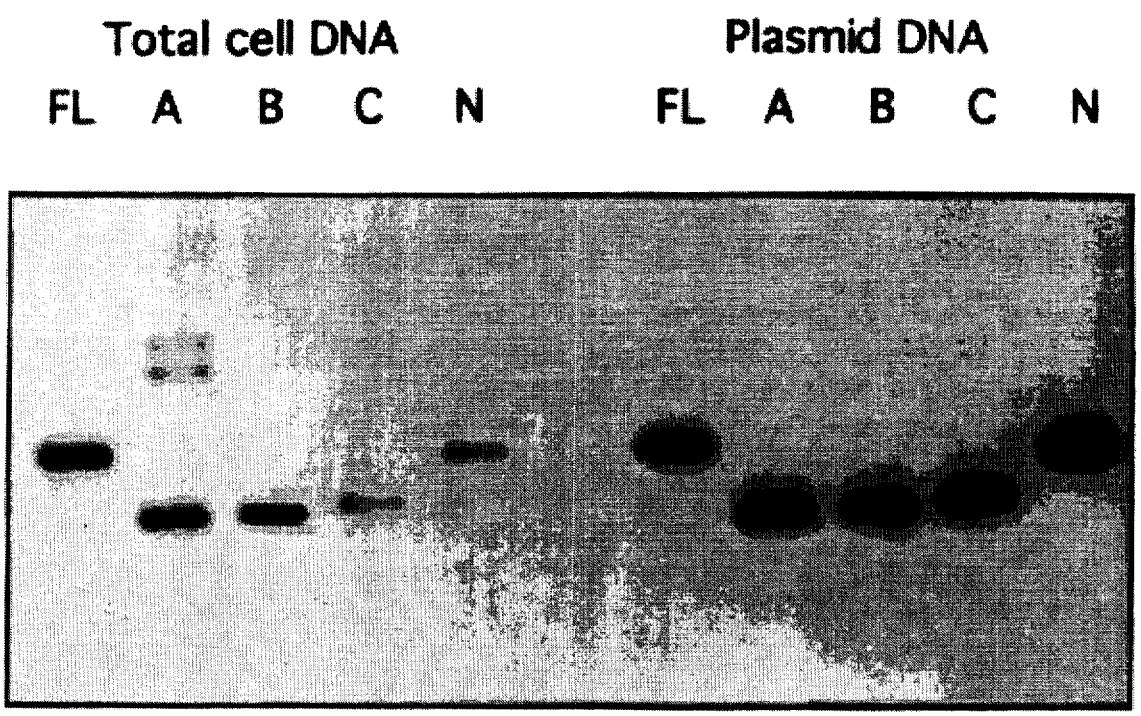
Figure 3:
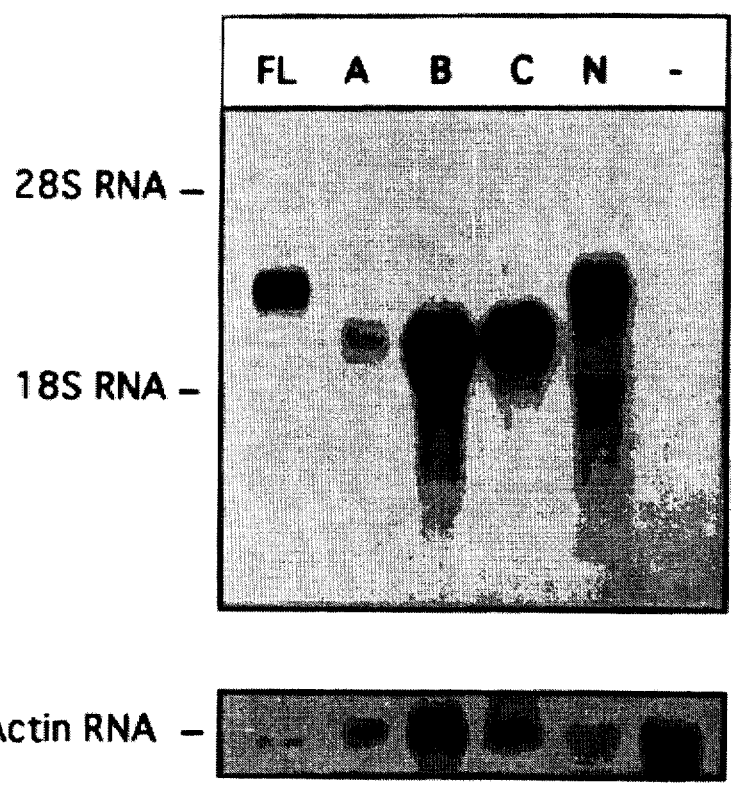
Figure 4A:
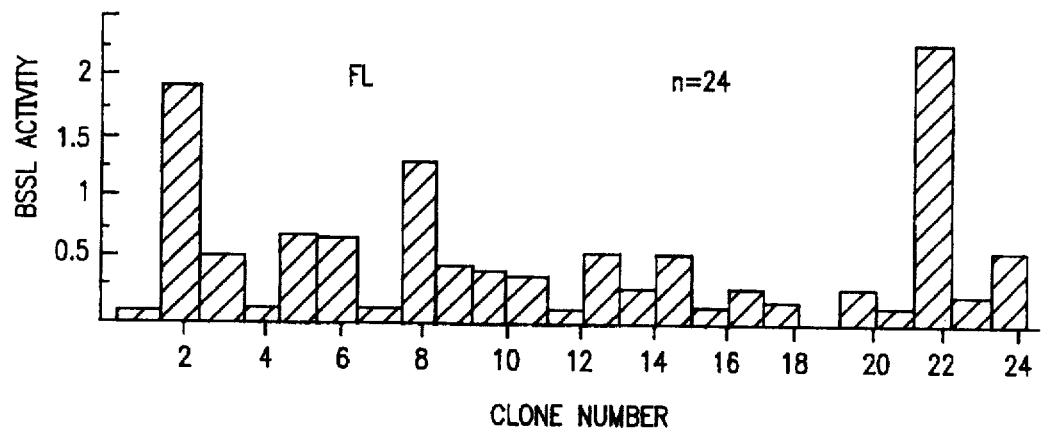
Figure 4B:
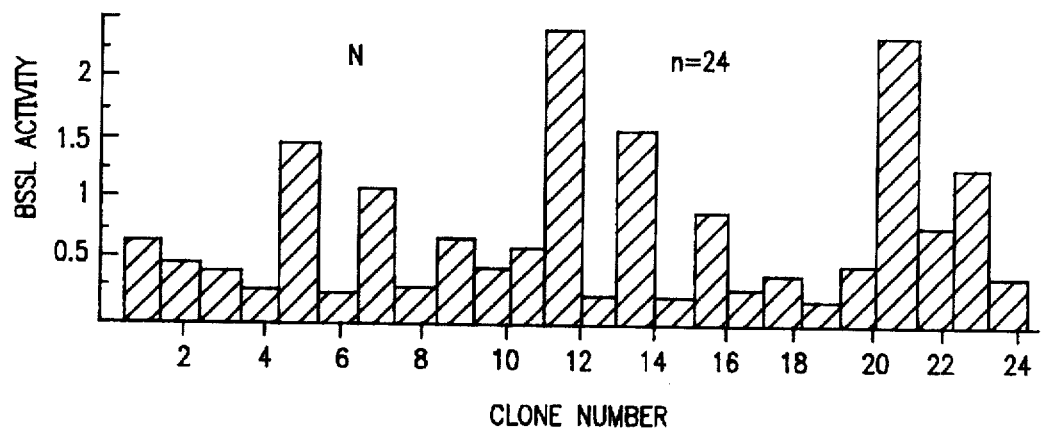
Figure 4C:
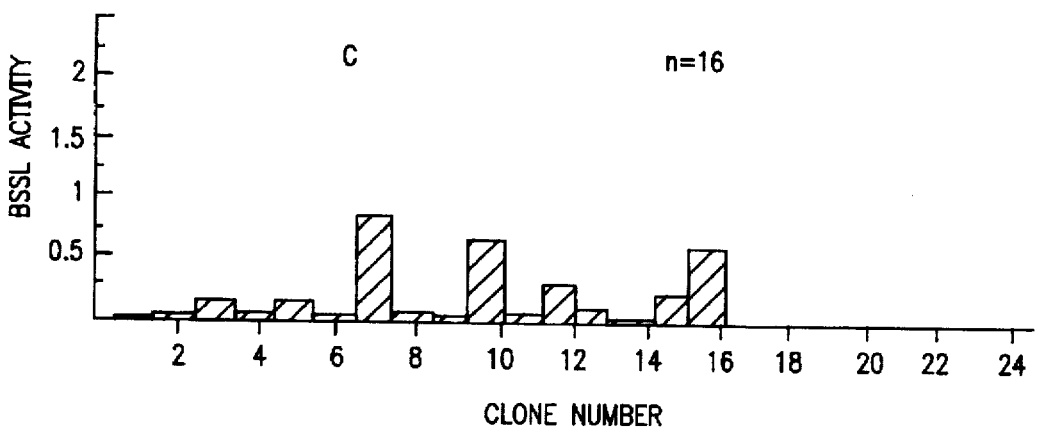
Figure 4D:
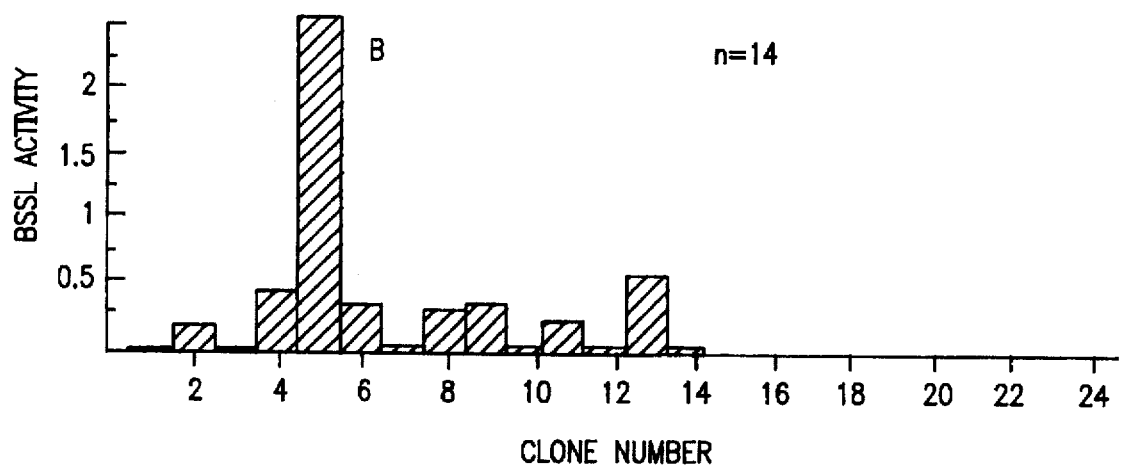
Figure 4E:
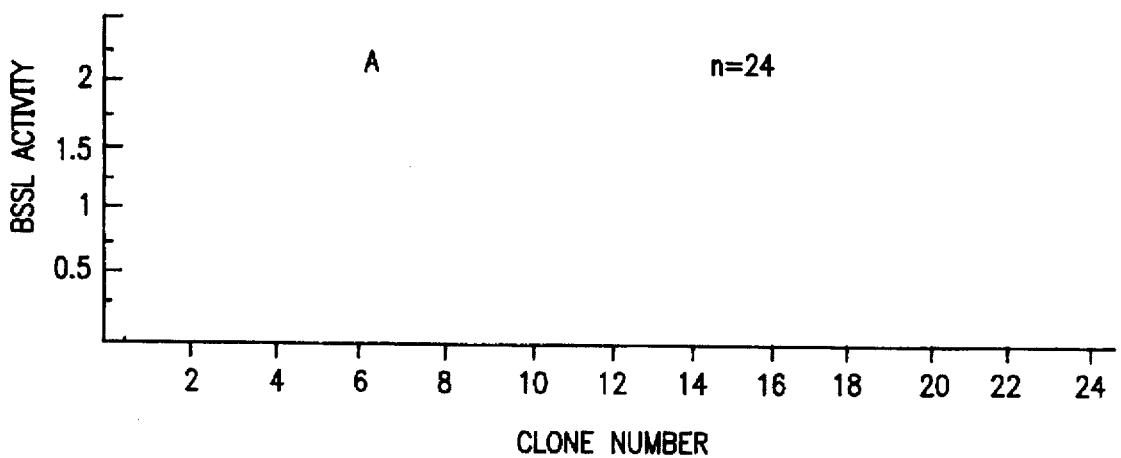
Figure 5A:
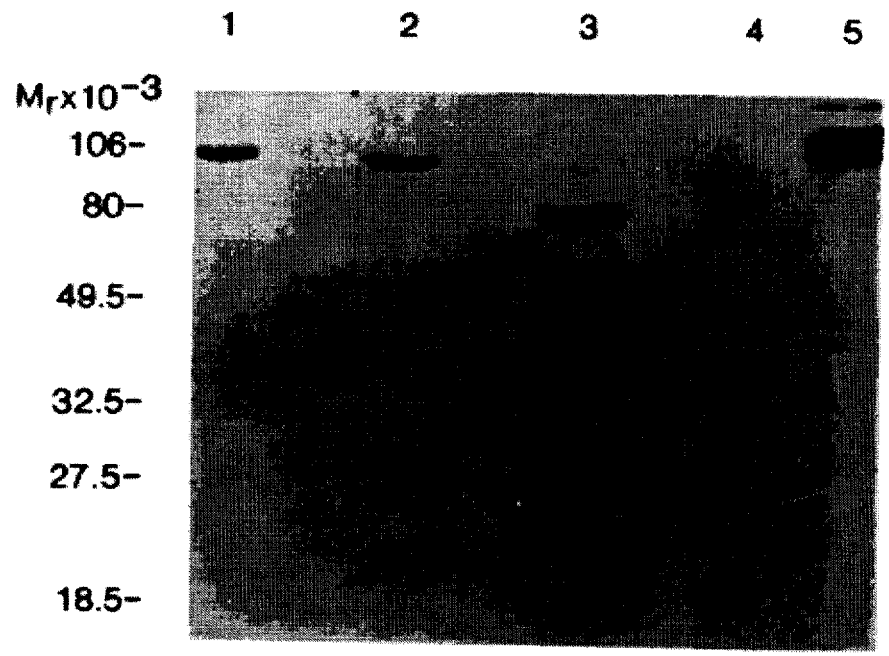
Figure 5B:
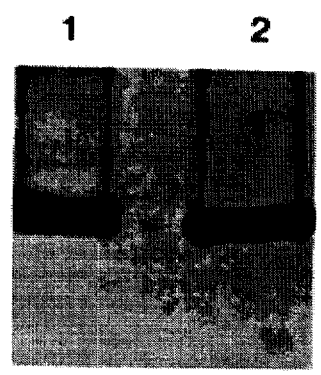
Figure 6:
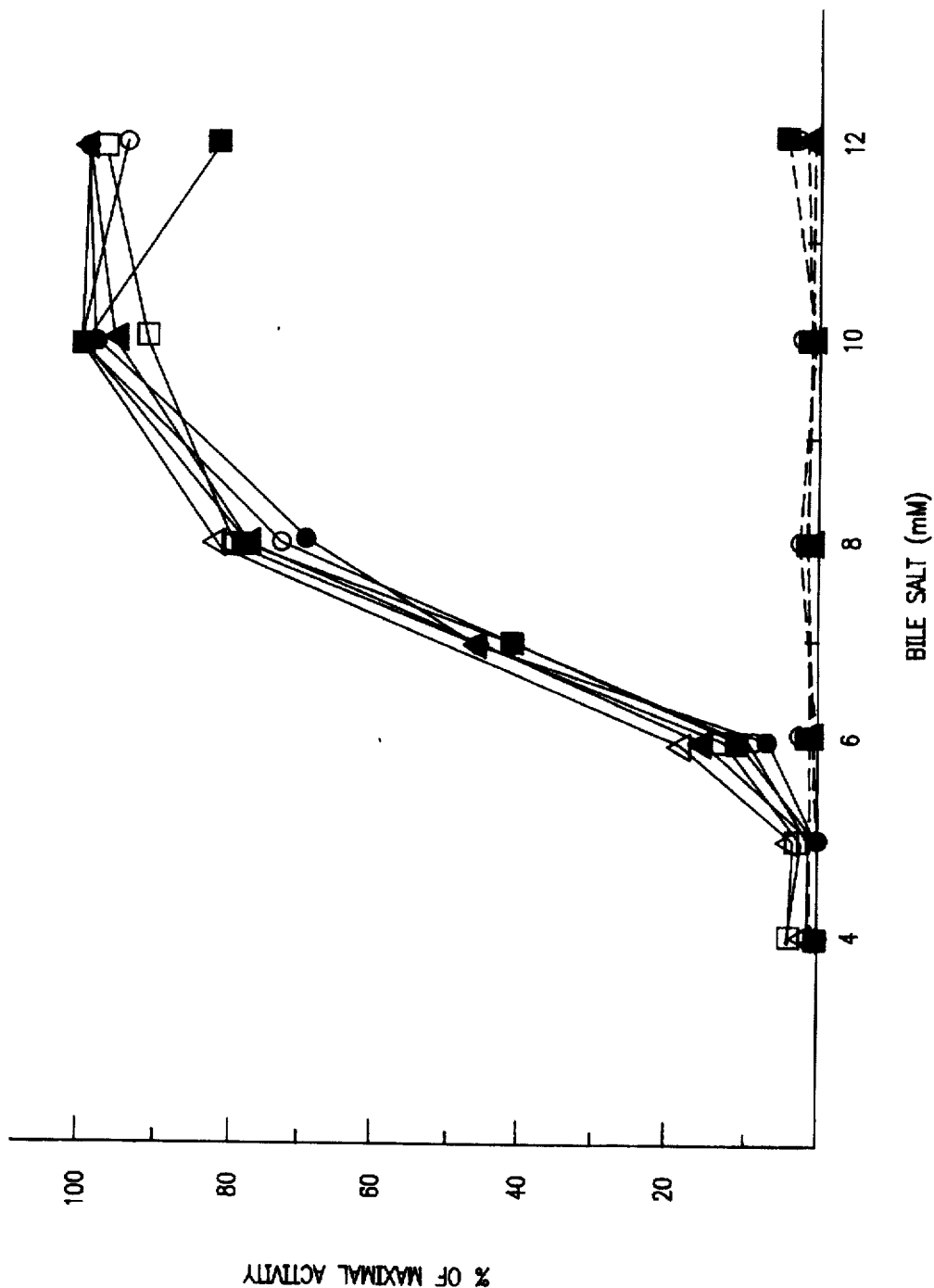
Figure 7A:
Figure 7B:
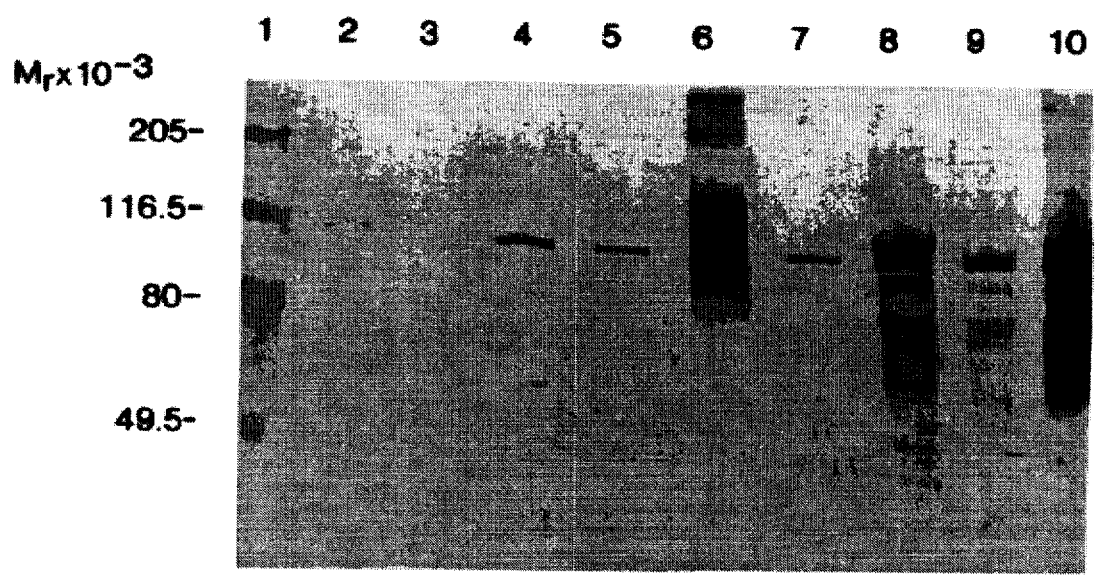
Figure 8:
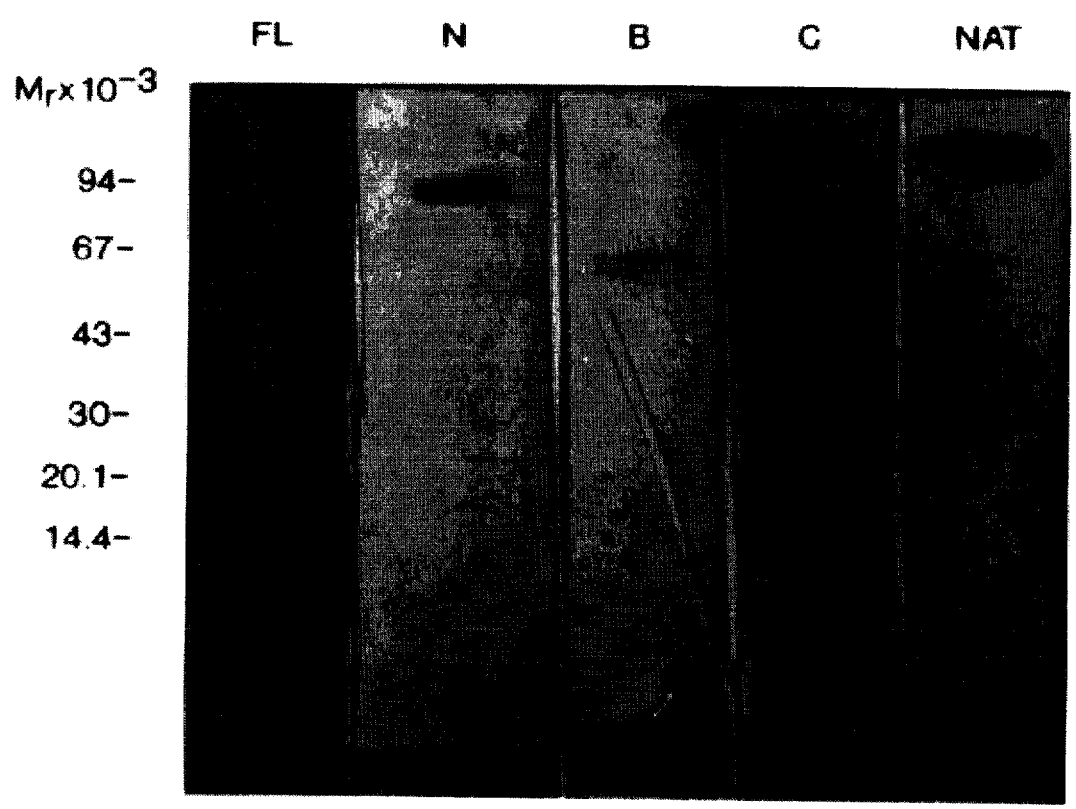

Experimental conditions were as described in the legend to FIG. 2. Lane 1, strain BL21(DE3)pLysS, not induced; Lane 2, strain BL21(DE3)pLysS, induced; Lane 3, strain JM109(DE3), not induced; Lane 4, strain JM109(DE3), induced.

B. Western blot, using antibodies to purified milk BSSL, of an 8-18% SDS-PAGE showing the expression of recombinant BSSL in different strains of *E. coli* using pGEMEX. Bacteria were induced with IPTG, and cytoplasmic and periplasmic proteins prepared from lysate as described in experimental procedures. The amounts of bacterial proteins loaded in lane 2-5 (periplasmic preparations) and 7-10 (cytoplasmic preparations) represent the same culture volume making the stain proportional to the production level. Lane 1, Pharmacia molecular size markers; Lanes 2 and 8, strain JM109(DE3), induced; Lanes 3 and 7, strain JM109 (DE3), not induced; Lanes 4 and 10, strain BL21(DE3) pLysS, induced; Lanes 5 and 9, strain BL21(DE3)pLysS, not induced; Lane 6, 25 ng of purified native milk BSSL.

FIG. 8

SDS-PAGE of purified recombinant BSSL and BSSL variants. Full-length recombinant BSSL (FL) and BSSL variants N, B, and C were purified as described. 3 μg of each was applied, except for variant B, of which 1.5 μg was used. 5 μg of purified native milk BSSL (NAT) was applied. The position of size markers are indicated to the left.

FIG. 9

Effect of sodium deoxycholate on the activation of recombinant BSSL and BSSL variants by sodium cholate. Purified preparations of recombinant full-length BSSL (●), recombinant BSSL variants B (o), C (■) and N (▲), and purified native milk BSSL (□) were assayed for lipase activity with different concentrations of sodium cholate in the absence (left panel) and in the presence of 5 mM (centre panel) or 10 mM (right panel) deoxycholate.

FIG. 10

Figure 9:
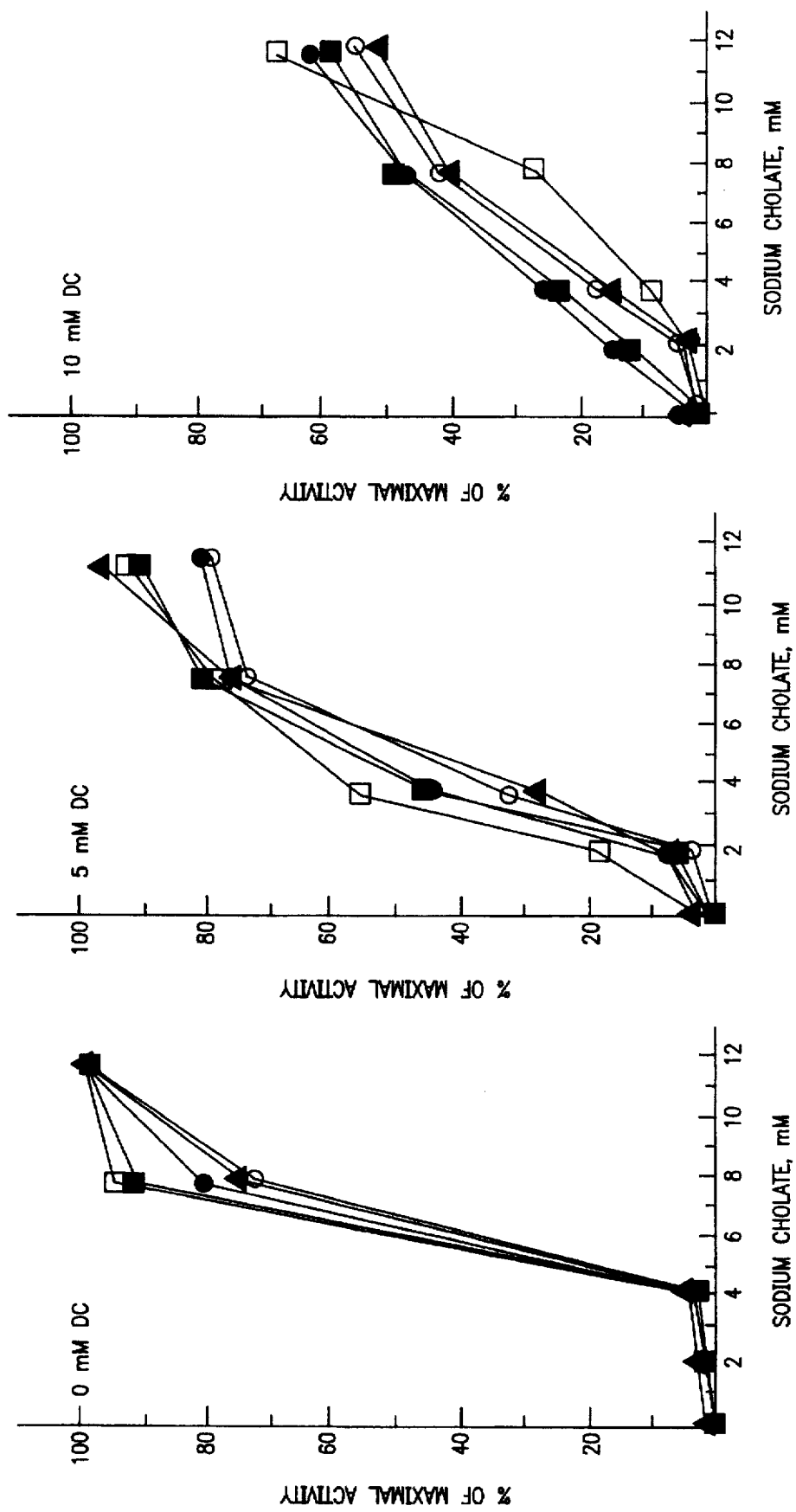
Figure 10:
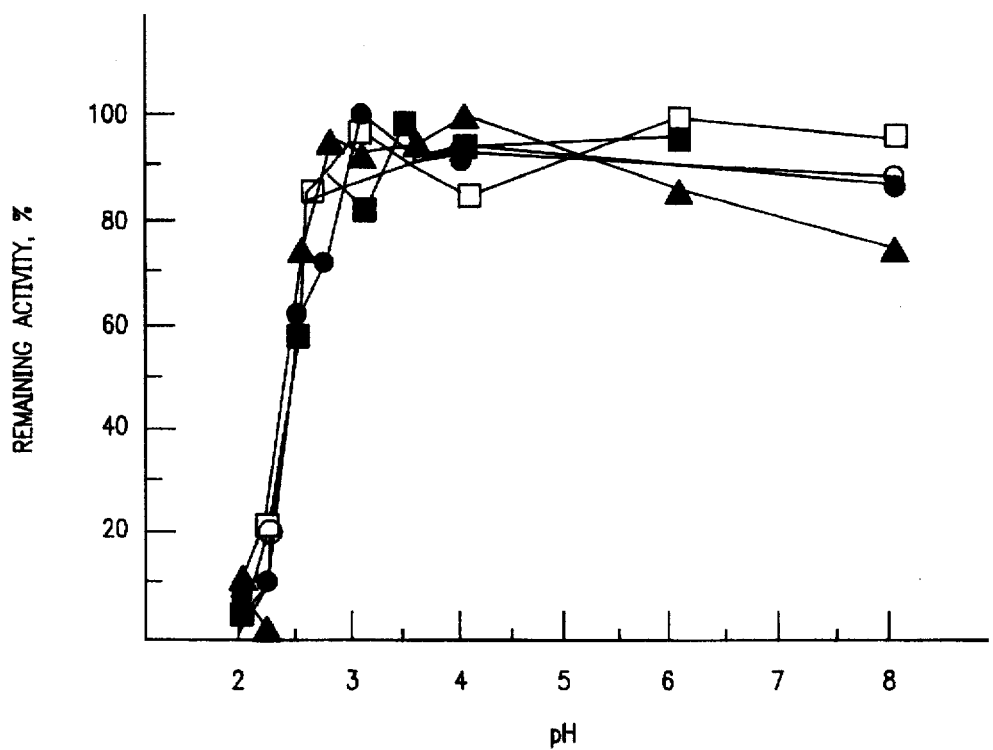
Figure 11:
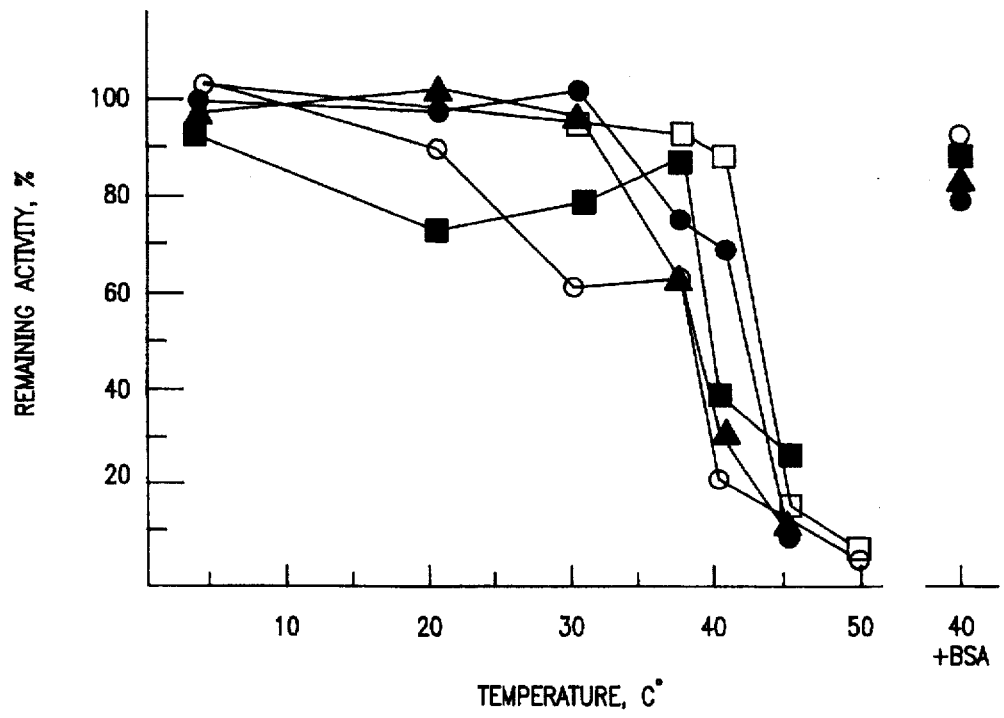
Figure 12:
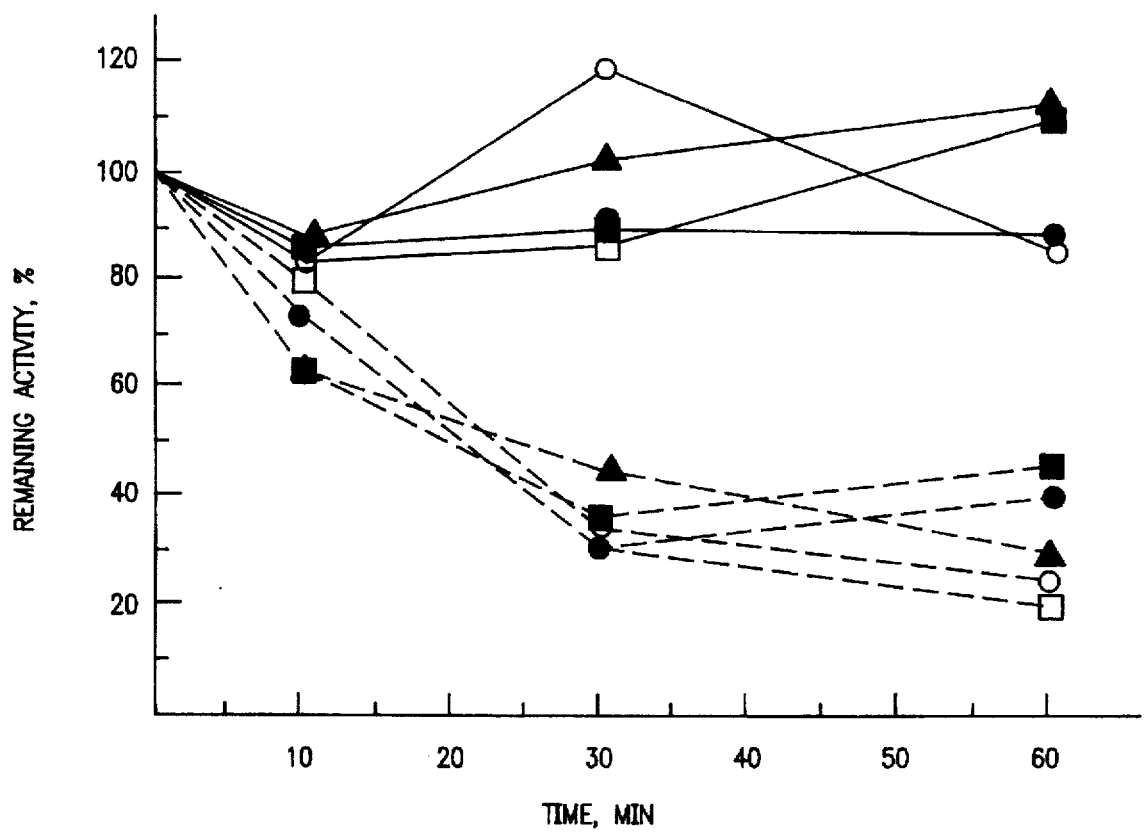
Figure 13:
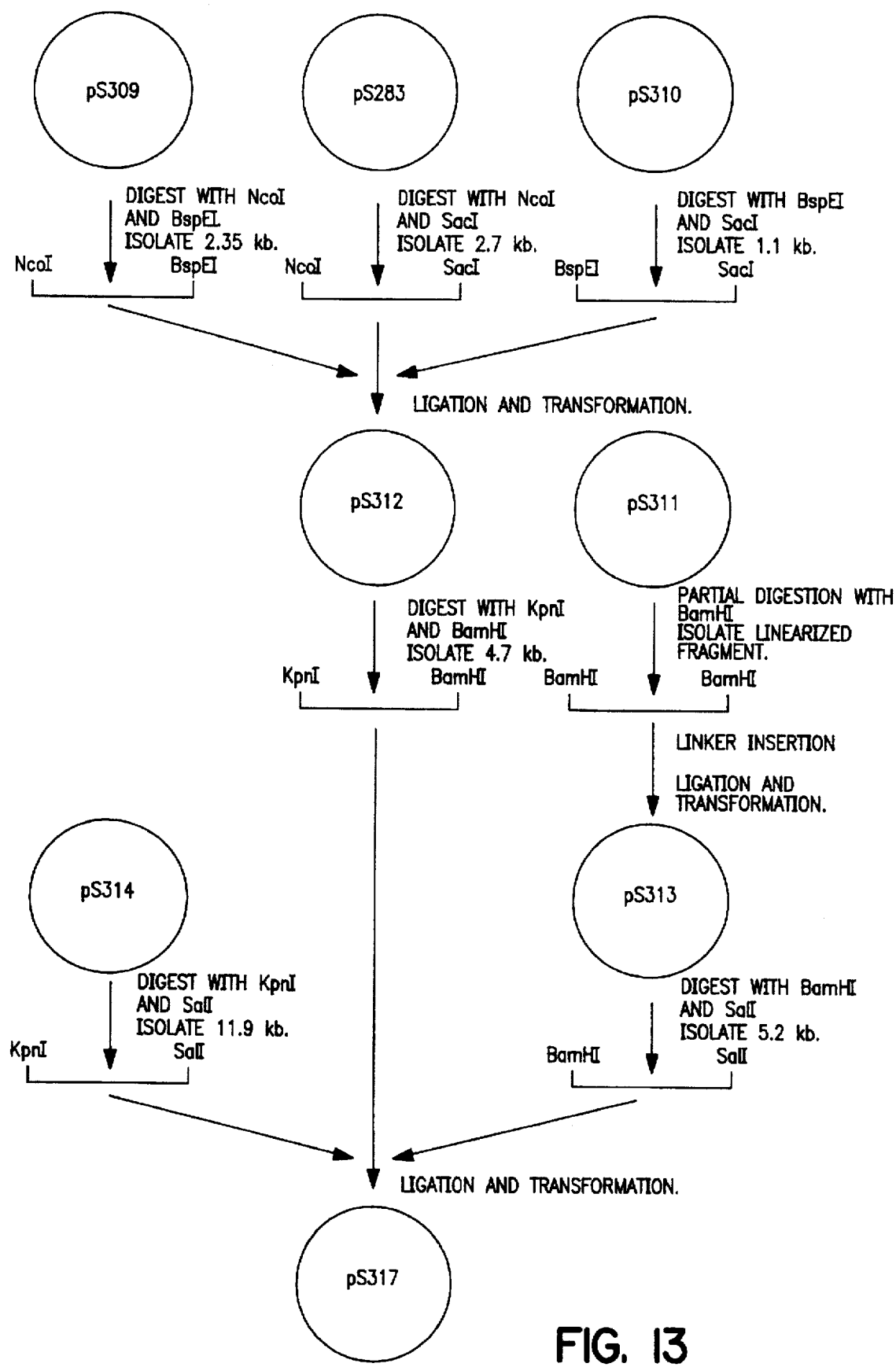
Figure 14:
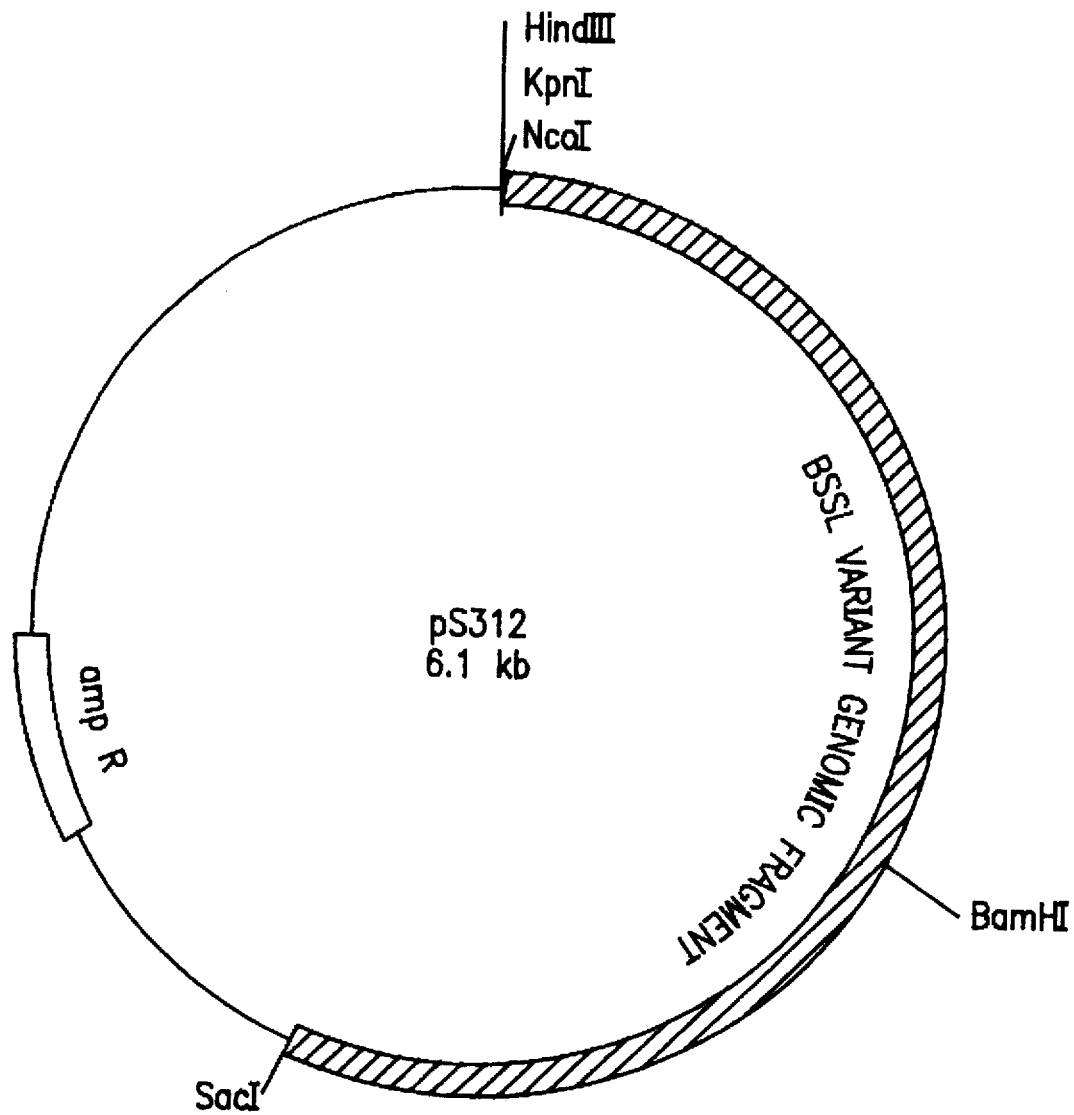
Figure 15:
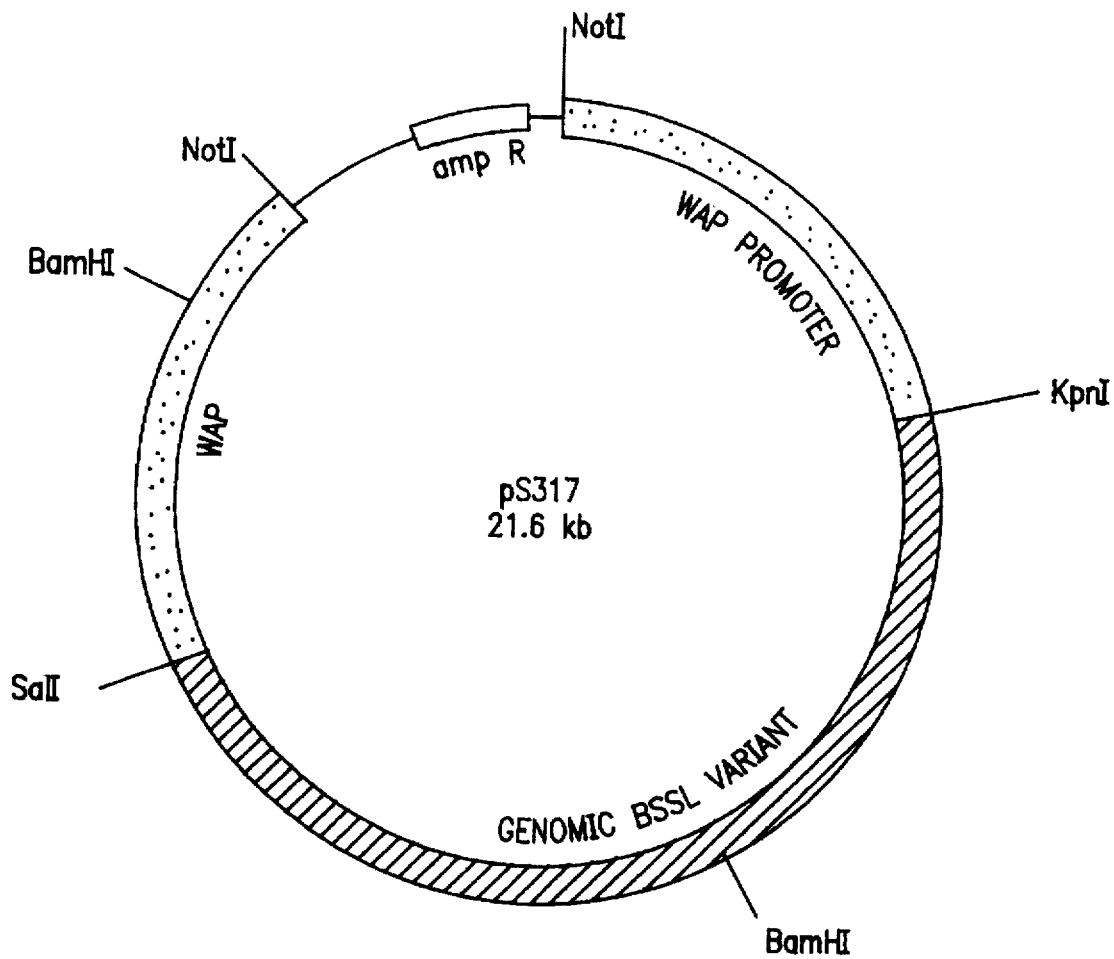
Figure 16:
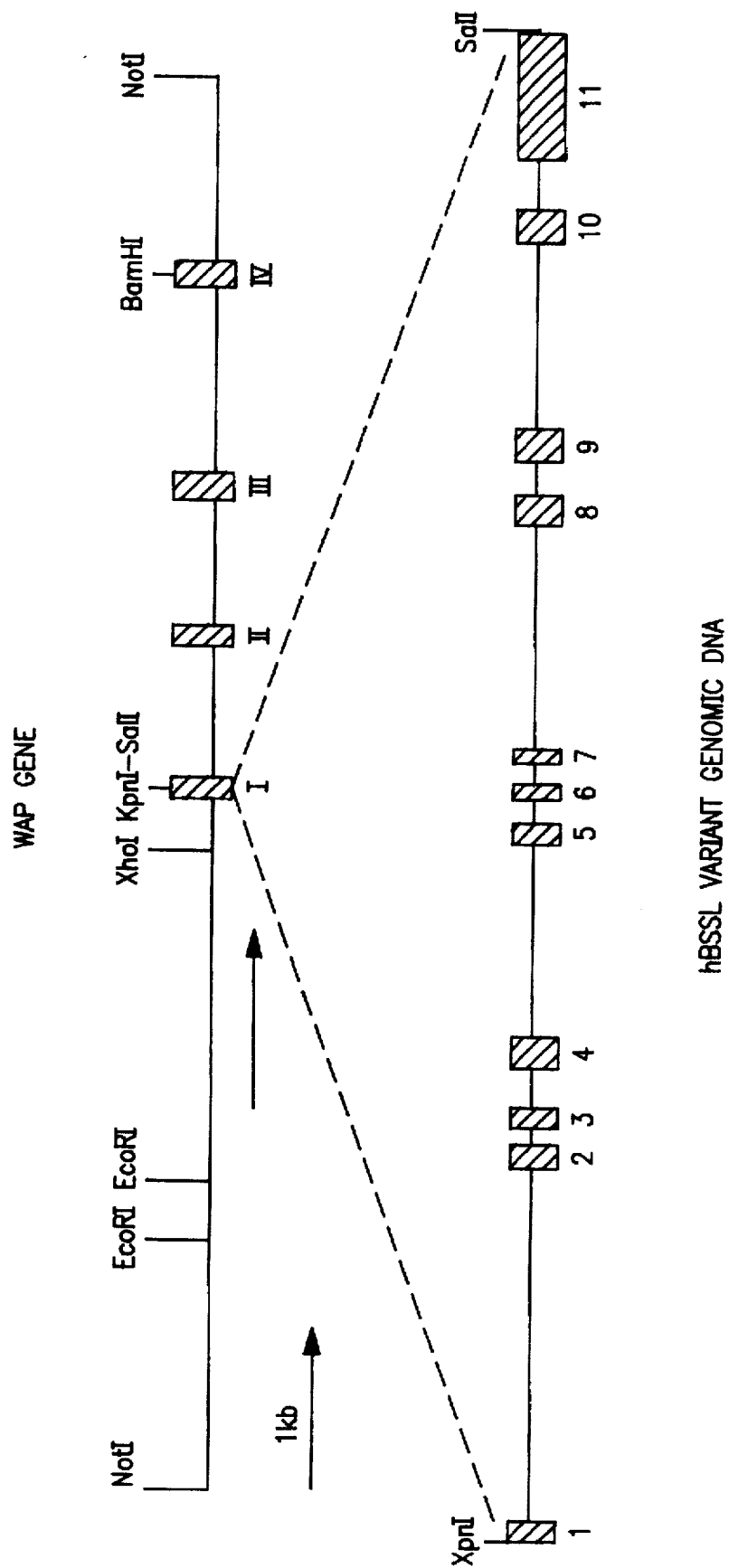
Figures 17A, 17B:
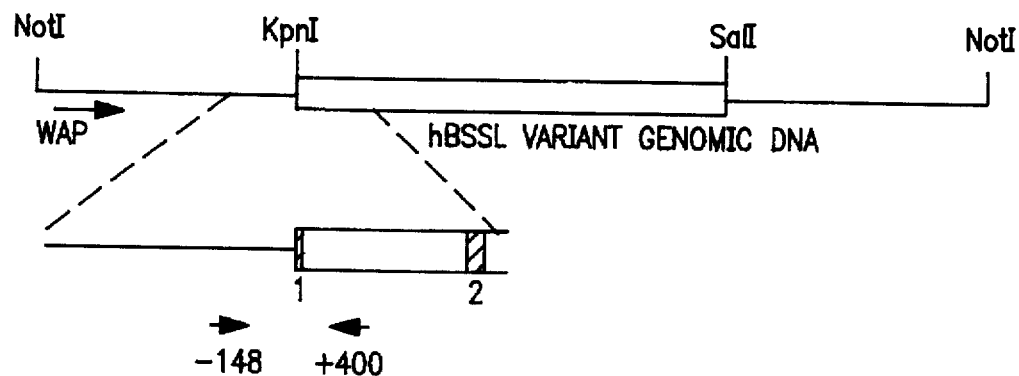
Figure 17C:
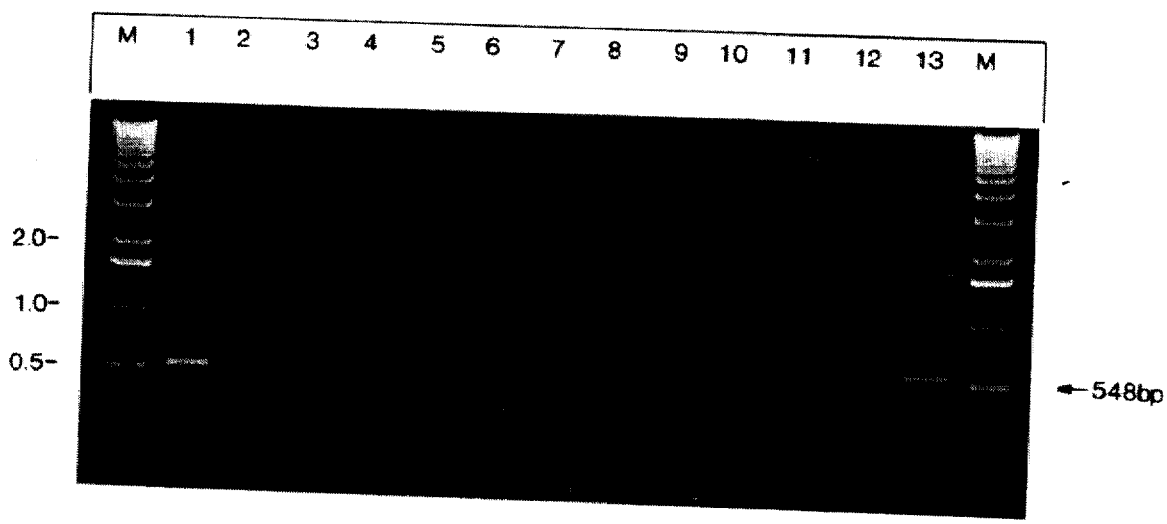
Figure 18:
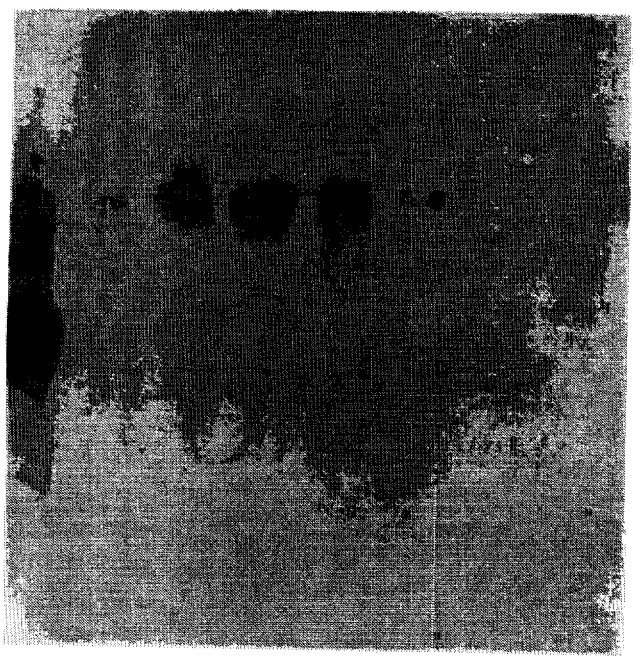
Figure 19:
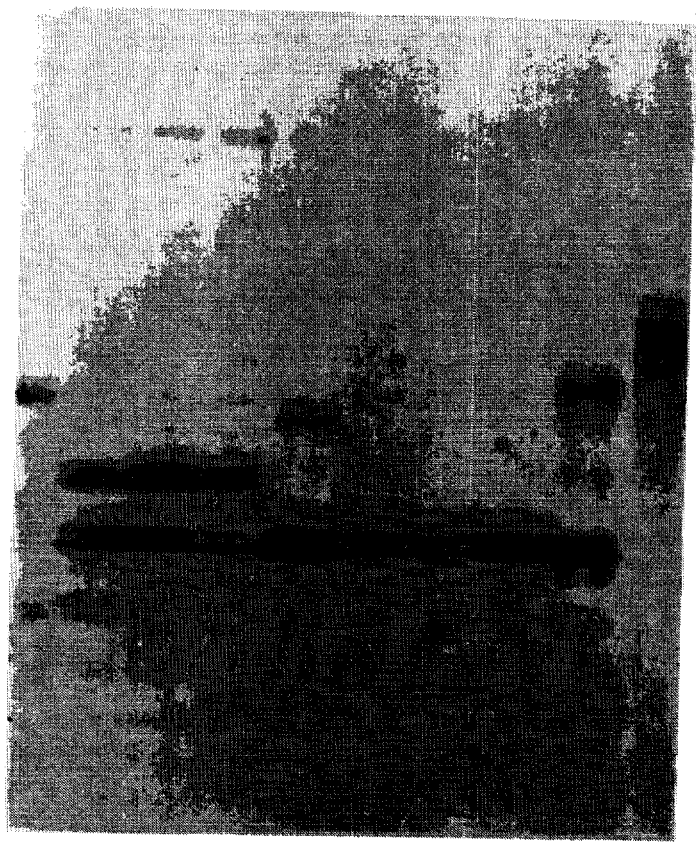

Stability of recombinant BSSL and BSSL variants at different pH. Native BSSL, recombinant full-length BSSL and BSSL variants were incubated at 37° C. in different buffers with pH 2-8. All buffers contained 1 mg/ml of bovine serum albumin. After 30 min aliquotes were withdrawn and assayed for lipase activity. For explanation of symbols, see the legend to FIG. 9.

FIG. 11

Heat stability of recombinant BSSL and BSSL variants. Purified recombinant full-length BSSL, BSSL variants and native milk BSSL were incubated at the temperatures indicated in 50 mM Tris-Cl buffer, pH 7.5. To one set of samples bovine serum albumin (BSA) was added to 1 mg/ml. After 30 min samples were withdrawn and assayed for lipase activity. Activities are expressed as per cent of the activity for each sample at 0 min. For explanation of symbols, see the legend to FIG. 9.

FIG. 12

Effect of bile salts on the inactivation of recombinant BSSL and BSSL variants by trypsin. Purified recombinant full-length BSSL, BSSL variants and native milk BSSL (15 μl containing 1-4 μg) were added to 60 μl of 1.0M Tris-Cl, pH 7.4 with 10 μg of trypsin (TPCK-trypsin, Boehringer-Mannheim) at 25° C. in the absence (broken lines) and in the presence (solid lines) of 10 mM sodium cholate. At the times indicated aliqoutes were withdrawn and assayed for lipase activity. Values are expressed as per cent of values obtained in control incubations in the absence of trypsin. For explanation of symbols, see the legend to FIG. 9.

FIG. 13

Method for production of the plasmid pS317. For further details, see section 3.1.

FIG. 14

Schematic structure of the plasmid pS312.

FIG. 15

Schematic structure of the plasmid pS317.

FIG. 16

Physical map representing the physical introduction of human BSSL variant genomic structure in the first exon of the WAP gene as described in section 3.1.

FIG. 17(A–C)

A. Schematic representation of the localization of PCR-primers used for identification of transgenic animals. The 5'-primer is positioned within the WAP sequence starting at the position –148 bp upstream of the fusion between the WAP and BSSL variant. The 3'-primer is localized in the first BSSL variant intron ending 400 bp downstream of the fusion point.

B. The sequences of the PCR primers used.

C. Agarose gel showing a typical analysis of the PCR analysis of the potential founder animals. M: molecular weight markers. Lane 1: control PCR-product generated from the plasmid pS317. Lanes 2-13: PCR reactions done with DNA preparations from potential founder animals.

FIG. 18

Northern blot analysis of RNA prepared from various tissues isolated from a female mouse transgenic for pS317. The tissues were isolated at day four of lactation. 10 μg of total RNA from each tissue was analyzed by agarose-formaldehyde separation, transferred to membranes and hybridized with $^{32}$P-labelled human BSSL cDNA. The lanes contain Mg: mammary gland; Li: liver; Ki: kidney; Sp: spleen; He: heart; Lu: lung; Sg: salivary gland; Br: brain. RNA sizes in nucleotides are indicated to the left.

FIG. 19

Western blotting of milk obtained from pS317 transgenic mice, and mice transgenic for a full-length cDNA vector pS314 and control animals. The samples were separated by SDS-PAGE and transferred to Immobilon filters and immunoblotted with antiserum raised against native human BSSL. Lane 1: molecular weight markers; Lanes 2,3 and 4: 2 milk from three F1 daughters (F1 30, 31, and 33) of pS317 founder FO #91; Lane 5: 2 μl milk from pS314 founder #90. Lanes 6, 7 and 8: 2 μl milk from three non-BSSL transgenic animals; Lane 9: purified murine BSSL; Lane 10: purified human native BSSL.

REFERENCES

Abouakil, N., Rogalska, E., and Lombardo, D. (1989): Biochim. Biophys. Acta 1002, 225–230

Atkinson, S. A., Bryan, M. H., and Andersson, G. H. (1981): J. Pediatr. 99, 617–624

Ausubel, F. M., Brent, R., Kingston, R. E., Moore, D. D., Seidman, J. G., Smith, J. A., Struhl, K. (eds.) in: Current Protocols in Molecular Biology (John Wiley & Sons, New York; edition of 1992)

Baba, T., Downs, D., Jackson, K. W, Tang, J. and Wang, C. S. (1991): Biochemistry 30, 500–510.

Bembäck, S., Blackberg, L., and Hernell, O. (1990): J. Clin. Invest. 85, 1221–1226

Björksten, B., Burman, L. G., deChateau, P., Fredrikzon, B., Gothefors, L. & Hernell, O. (1980): Br. Med. J. 201, 267-272.

Bläckberg, L. & Hernell, O. (1981): Eur. J. Biochem 116, 221-225.

Bläckberg, L. and Hernell, O. (1983): FEBS Lett. 157, 337-341

Campbell, S. M., Rosen, J. M., Hennighausen, L. G., Strech-Jurk, U. and Sippel, A. E. (1984): Nucleic Acid Res. 12, 8685-8697.

Chappell, J. E., Clandinin, M. T., Kearney-Volpe, C., Reichman, B., and Swyer, P. W. (1986): J. Pediatr. 108, 439-447

Fontaine, R., Carter, C., and Hui, D. (1991): Biochemistry 30, 7008-1014

Graham, F. L., and Van der Eb, A. J. (1973): Virology 52, 456-467

Hamosh, M., Freed, L. M., York, C. M., Sturman, J. A., and Hamosh, P. (1986): Fed. Proc. 45, 1452

Han, J. H., Stratowa, C., and Rutter, W. J. (1987): Biochemistry 26, 1617-1625

Hennighausen, L., Ruiz, L. & Wall, R. (1990): Current Opinion in Biotechnology 1, 74-78.

Hernell, O. (1975): Eur. J. Clin. Invest. 5, 267-272

Hernell, O., Bläckberg, L., and Lindberg, T. in: Textbook of gastroenterology and nutrition in infancy (Lebenthal, E. ed) pp. 209-217 (Raven Press, New York 1989)

Hernell, O., Staggers, J. E. and Carey, M. C. (1990): Biochemistry 29, 2041-2056

Hernell, O. and Bläckberg, L. in: Encyclopedia of human biology (Dulbecco, R. ed.) Vol. 3, pp. 47-56 (Academic Press, San Diego 1991)

Hernell, O., Bläckberg, L., Chen, Q., Sternby, B. and Nilsson, Å. (1993): J. Pediatr. Gastroenterol. Nutr. (In press)

Hogan, B., Constantini, F. and Lacy, E. (1986): Manipulating the mouse embryo. A Laboratory Manual. Cold Spring Harbor Laboratory Press.

Hui, D. and Kissel, J. A. (1990): Febs Lett. 276, 131-134.

Kyger, E. M., Wiegand, R. C., and Lange, L. G. (1989): Biochem. Biophys. Res. Commun. 164, 1302-1309

Laemmli, U. K. (1970): Nature (London) 227, 680-685

Lidberg, U., Nilsson, J., Strömberg, K., Stenman, G., Sahlin, P., Enerbäck, S. G. and Bjursell, G. (1992): Genomics 13, 630-640

Lusky, M., and Botchan, M. R. (1984): Cell 36, 391-401

Nilsson, J., Bläckberg, L., Carlsson, P., Enerbäck, S., Hernell, O. and Bjursell, G. (1990): Eur. J. Biochem. 192, 543-550.

Pavlakis, G. N., and Hamer, D. H. (1983): Proc. Natl. Acad. Sci. U.S.A. 80, 397-401

Reue, K., Zambaux, J., Wong, H., Lee, G., Leete, T. H., Ronk, M., Shively, J. E., Sternby, B., Borgstrom, B., Ameis, D. and Schotz, M. C. (1991): J. Lipid. Res. 32, 267-276.

Sarver, N., Byrne, J. C., and Howell, P. M. (1982): Proc. Natl. Acad. Sci. U.S.A. 79, 7147-7151

Studier, F. W. and Moffat, B. A. (1986): J. Mol. Biol. 189, 113-130

Williamson, S., Finucane, E., Ellis, H., and Gamsu, H. R. (1978): Arch. Dis. Childhood 53, 555-563

---

We claim:

1. A process of producing a transgenic non-human female mammal that produces in mammary recoverable amounts of a human BSSL variant that retains BSSL activity, comprising
   (a) introducing an expression system into a fertilized egg of a non-human mammal, wherein
      (i) said expression system comprises a hybrid gene that is expressed in the mammary gland of an adult female mammal harboring said hybrid gene in its genome,
      (ii) said hybrid gene comprises a DNA molecule encoding a human BSSL variant that retains BSSL activity and operatively linked to a promoter of a gene that is expressed in the mammary gland of a mammal, and wherein the DNA molecule encodes a BSSL variant in which one or more but not all of the amino acids in the region corresponding to amino acids 536–722, inclusive, of SEQ ID NO:3 have been deleted;
   (b) introducing the fertilized egg containing the expression system into a host non-human mammal of the same species as the fertilized egg;
   (c) allowing the host non-human mammal to produce progeny; and
   (d) selecting a female progeny non-human mammal that produces recoverable amounts of the BSSL variant in its milk.

2. A process of producing a transgenic female mouse that produces in mammary tissue recoverable amounts of a human BSSL variant that retains BSSL activity and is substantially incapable of expressing a BSSL gene of the mouse itself, comprising
   (a) destroying the native BSSL gene-expressing capability of the mouse by mutation of mouse DNA sequences responsible for the expression of the native BSSL genes so that substantially no murine BSSL is produced, and injecting an expression system according to claim 1 or 6 into a fertilized egg or embryo cell of said mouse, or
   (b) destroying the native BSSL gene-expressing capability of the mouse by replacing all or part of the BSSL genes of cells of the mouse by homologous recombination with an expression system according to claim 11 or 6, and introducing the genetically modified cells into a developing embryo,
   and then transferring the genetically modified egg or embryo produced by (a) or (b) above into a pseudopregnant female mouse to develop into a transgenic female mouse having the BSSL expression system in its germline and producing in its mammary tissue recoverable amounts of a human BSSL variant that retains BSSL activity.

3. A transgenic non-human female mammal produced by the process of claim 1 or 6, wherein said mammal produces in mammary tissue recoverable amounts of a human BSSL variant that retains BSSL activity.

4. A transgenic non-human female mammal according to claim 3, wherein said mammal produces in mammary tissue recoverable amounts of a human BSSL variant that retains BSSL activity, which mammal is selected from the group consisting of mice, rats, rabbits, sheep, pigs, and cattle.

5. Progeny of a transgenic non-human mammal according to claim 3, wherein said progeny produce in mammary tissue recoverable amounts of a human BSSL variant that retains BSSL activity.

6. A process of producing a transgenic non-human female mammal that produces in mammary recoverable amounts of a human BSSL variant that retains BSSL activity, comprising
   (a) introducing an expression system into a fertilized egg of a non-human mammal, wherein
      (i) said expression system comprises a hybrid gene that is expressed in the mammary gland of an adult female mammal harbouring said hybrid gene in its genome,
      (ii) said hybrid gene comprises a DNA molecule encoding a human BSSL variant that retains BSSL activity and operatively linked to a promoter of a gene that is expressed in the mammary gland of a mammal and wherein the DNA molecule encodes a BSSL variant whose amino acid sequence is at least 90% identical to the amino acid sequence shown as SEQ ID NO:7 in the Sequence Listing and does not encode for asparagine at position 187 of the variant;
   (b) introducing the fertilized egg containing the expression system into a host non-human mammal of the same species as the fertilized egg;
   (c) allowing the host non-human mammal to produce progeny; and (d) selecting a female progeny non-human mammal that produces recoverable amounts of the BSSL variant in its milk.

7. A transgenic female mouse produced by the method of claim 2 that produces in mammary tissue recoverable amounts of a human BSSL variant that retains BSSL activity, and is substantially incapable of expressing a BSSL gene of the mouse itself.

* * * * *